US009963467B2

(12) United States Patent
Reddy et al.

(10) Patent No.: US 9,963,467 B2
(45) Date of Patent: May 8, 2018

(54) BORONIC ACID DERIVATIVES AND THERAPEUTIC USES THEREOF

(71) Applicant: Rempex Pharmaceuticals, Inc., San Diego, CA (US)

(72) Inventors: Raja Reddy, San Diego, CA (US); Tomasz Glinka, Cupertino, CA (US); Scott Hecker, Del Mar, CA (US); Maxim Totrov, San Diego, CA (US); Olga Rodny, Mill Valley, CA (US)

(73) Assignee: Rempex Pharmaceuticals, Inc., San Diego, CA (US)

( * ) Notice: Subject to any disclaimer, the term of this patent is extended or adjusted under 35 U.S.C. 154(b) by 0 days. days.

(21) Appl. No.: 15/312,173

(22) PCT Filed: May 18, 2015

(86) PCT No.: PCT/US2015/031400
§ 371 (c)(1),
(2) Date: Nov. 17, 2016

(87) PCT Pub. No.: WO2015/179308
PCT Pub. Date: Nov. 26, 2015

(65) Prior Publication Data
US 2017/0088561 A1 Mar. 30, 2017

Related U.S. Application Data

(60) Provisional application No. 62/000,400, filed on May 19, 2014.

(51) Int. Cl.
*A61K 31/69* (2006.01)
*C07F 5/02* (2006.01)
*A61K 31/407* (2006.01)
*A61K 31/43* (2006.01)
*A61K 31/545* (2006.01)
*A61K 31/546* (2006.01)
*A61K 31/4196* (2006.01)
*A61K 31/427* (2006.01)
*A61K 45/06* (2006.01)
*A61K 47/26* (2006.01)

(52) U.S. Cl.
CPC ............ *C07F 5/025* (2013.01); *A61K 31/407* (2013.01); *A61K 31/4196* (2013.01); *A61K 31/427* (2013.01); *A61K 31/43* (2013.01); *A61K 31/545* (2013.01); *A61K 31/546* (2013.01); *A61K 31/69* (2013.01); *A61K 45/06* (2013.01); *A61K 47/26* (2013.01)

(58) Field of Classification Search
CPC ............................... C07F 5/025; A61K 31/407
See application file for complete search history.

(56) References Cited

U.S. PATENT DOCUMENTS

| 4,194,047 A | 3/1980 | Christensen et al. |
| 4,260,543 A | 4/1981 | Miller |
| 4,409,214 A | 10/1983 | Takaya et al. |
| 4,822,786 A | 4/1989 | Zama et al. |
| 5,442,100 A | 8/1995 | Bjorkquiest et al. |
| 5,888,998 A | 3/1999 | Maiti et al. |
| 6,184,363 B1 | 2/2001 | Shoichet et al. |
| 6,586,615 B1 | 7/2003 | Kettner et al. |
| 7,271,186 B1 | 9/2007 | Shoichet et al. |
| 7,439,253 B2 | 10/2008 | Lampilas et al. |
| 7,582,621 B2 | 9/2009 | Baker et al. |
| 7,612,087 B2 | 11/2009 | Aszodi et al. |
| 8,680,136 B2 | 3/2014 | Hirst et al. |
| 9,012,491 B2 | 4/2015 | Reddy et al. |
| 9,101,638 B2 * | 8/2015 | Reddy |
| 9,132,140 B2 * | 9/2015 | Reddy ..................... C07F 5/025 |
| 9,156,858 B2 | 10/2015 | Reddy et al. |
| 9,241,947 B2 * | 1/2016 | Reddy |
| 9,296,763 B2 | 3/2016 | Hirst et al. |
| 9,511,142 B2 | 12/2016 | Burns et al. |
| 9,642,869 B2 * | 5/2017 | Reddy ................. A61K 31/407 |
| 9,687,497 B1 | 6/2017 | Bis et al. |
| 9,694,025 B2 | 7/2017 | Hirst et al. |
| 2004/0019203 A1 | 1/2004 | Micetich et al. |
| 2004/0157826 A1 | 8/2004 | Lampilas et al. |
| 2005/0020572 A1 | 1/2005 | Aszodi et al. |
| 2006/0019116 A1 | 1/2006 | Conley et al. |
| 2006/0178357 A1 | 8/2006 | Buynak et al. |
| 2006/0210883 A1 | 9/2006 | Chen et al. |
| 2010/0056478 A1 | 3/2010 | Desarbre et al. |
| 2010/0120715 A1 | 5/2010 | Burns et al. |
| 2010/0256092 A1 | 10/2010 | Xia et al. |

(Continued)

FOREIGN PATENT DOCUMENTS

| EP | 1550657 A1 | 7/2005 |
| EP | 2508506 A1 | 10/2012 |

(Continued)

OTHER PUBLICATIONS

CAS Registry No. 2005:329437 CAPLUS; "Product subclass 28: Vinylboranes", Vaultier et al., (2004); XP-002764965; 1 page.
Austad et al. "Development of a multi kilogram-scale, tandem cyclopropanation ring-expansion reaction en route to hedgehog antagonist IPI-926", Org Process Res Dev., (2016) 20(4):786-798; Supporting Information, 70 pages.
Banker G.S. et al. [Eds.], Modern Pharmaceutics, 4th Edition; Marcel Dekker, Inc. (2002); Chapters 9 and 10, 98 pages.
Braisted et al., "Discovery of a potent small molecule IL-2 inhibitor through fragment assembly", J Am Chem Soc., (2003) 125(13): 3714-3715; Supporting Information, 42 pages.
Buesking et al., "Asymmetric Synthesis of Protected alpha-Amino Boronic Acid Derivatives with an Air- and Moisture-stable Cu(II) Catalyst", J Org Chem. (Mar. 2014) 79(8):3671-3677.
Chandrasekhar et al., "The first Corey-Chaykovsky epoxidation and cyclopropanation in ionic liquids", Tetrahedron Letts. (2003) 44:3629-3630.
Charette et al., "Palladium-catalyzed Suzuki-type cross-couplings of iodocyclopropanes with boronic acids: Synthesis of trans-1,2-dicyclopropyl alkenes", J Org Chem. (1996) 61(25): 8718-8719; Supporting Information, 52 pages.
Chinchilla et al., "Recent advances in Sonogashira reactions", Chem Soc Rev., (2011) 40: 5084-5121.
Clark et al., "Concise synthesis of the C-1-C-12 fragment of amphidinolides T1-T5", Org Biomol Chem. (2011) 9(13): 4823-4830.

(Continued)

*Primary Examiner* — Golam M Shameem
(74) *Attorney, Agent, or Firm* — Knobbe Martens Olson & Bear LLP

(57) ABSTRACT

Disclosed herein are antimicrobial compounds compositions, pharmaceutical compositions, the use and preparation thereof. Some embodiments relate to boronic acid derivatives and their use as therapeutic agents.

31 Claims, No Drawings

(56) References Cited

U.S. PATENT DOCUMENTS

| | | |
|---|---|---|
| 2011/0288063 A1 | 11/2011 | Maiti et al. |
| 2012/0040932 A1 | 2/2012 | Hirst et al. |
| 2013/0316978 A1 | 11/2013 | Reddy et al. |
| 2013/0331355 A1 | 12/2013 | Griffith et al. |
| 2013/0345172 A1 | 12/2013 | Hirst et al. |
| 2014/0194284 A1 | 7/2014 | Reddy et al. |
| 2014/0194381 A1 | 7/2014 | Reddy et al. |
| 2014/0194382 A1 | 7/2014 | Reddy et al. |
| 2014/0194385 A1 | 7/2014 | Reddy et al. |
| 2014/0194386 A1 | 7/2014 | Burns et al. |
| 2014/0206648 A1 | 7/2014 | Reddy et al. |
| 2015/0119363 A1 | 4/2015 | Dudley et al. |
| 2016/0220591 A1 | 8/2016 | Hirst et al. |
| 2016/0339045 A1 | 11/2016 | Griffith et al. |
| 2017/0057979 A1 | 3/2017 | Hecker et al. |
| 2017/0136047 A1 | 5/2017 | Reddy et al. |
| 2017/0173055 A1 | 6/2017 | Bis et al. |

FOREIGN PATENT DOCUMENTS

| | | |
|---|---|---|
| FR | 2573070 A1 | 5/1986 |
| JP | 2003-229277 | 8/2003 |
| JP | 2004-291253 | 10/2004 |
| WO | WO 1987/05297 | 9/1987 |
| WO | WO 1989/10961 | 11/1989 |
| WO | WO 1998/56392 A1 | 12/1998 |
| WO | WO 2000/035904 A1 | 6/2000 |
| WO | WO 2000/035905 A1 | 6/2000 |
| WO | WO 2001/023374 A1 | 4/2001 |
| WO | WO 2001/030149 | 5/2001 |
| WO | WO 2002/022137 A1 | 3/2002 |
| WO | WO 2002/083884 | 10/2002 |
| WO | WO 2003/070714 | 8/2003 |
| WO | WO 2004/039859 | 5/2004 |
| WO | WO 2004/058679 A2 | 7/2004 |
| WO | WO 2004/064755 A2 | 8/2004 |
| WO | WO 2005/033090 | 4/2005 |
| WO | WO 2005/035532 A1 | 4/2005 |
| WO | WO 2005/087700 | 9/2005 |
| WO | WO 2006/052733 A1 | 5/2006 |
| WO | WO 2006/091771 | 8/2006 |
| WO | WO 2007/058602 A2 | 5/2007 |
| WO | WO 2007/065288 A2 | 6/2007 |
| WO | WO 2007/095638 | 8/2007 |
| WO | WO 2008/039420 A2 | 4/2008 |
| WO | WO 2008/116813 A1 | 10/2008 |
| WO | WO 2009/046098 A1 | 4/2009 |
| WO | WO 2009/064413 A1 | 5/2009 |
| WO | WO 2009/064414 A1 | 5/2009 |
| WO | WO 2009/091856 A1 | 7/2009 |
| WO | WO 2009/117540 A1 | 9/2009 |
| WO | WO 2009/139834 A1 | 11/2009 |
| WO | WO 2009/140309 A2 | 11/2009 |
| WO | WO 2010/056827 A1 | 5/2010 |
| WO | WO 2010/075286 A1 | 7/2010 |
| WO | WO 2010/097675 A1 | 9/2010 |
| WO | WO 2010/130708 A1 | 11/2010 |
| WO | WO 2010/144338 A1 | 12/2010 |
| WO | WO 2011/017125 A1 | 2/2011 |
| WO | WO 2011/103686 A1 | 9/2011 |
| WO | WO 2011/123502 A1 | 10/2011 |
| WO | WO 2011/154953 | 12/2011 |
| WO | WO 2012/021455 A1 | 2/2012 |
| WO | WO 2012/058065 A1 | 5/2012 |
| WO | WO 2012/067664 A1 | 5/2012 |
| WO | WO 2012/106995 A1 | 8/2012 |
| WO | WO 2012/136383 A1 | 10/2012 |
| WO | WO 2013/033461 A1 | 3/2013 |
| WO | WO 2013/053372 A1 | 4/2013 |
| WO | WO 2013/056163 A1 | 4/2013 |
| WO | WO 2013/092979 A1 | 6/2013 |
| WO | WO 2013/104774 A1 | 7/2013 |
| WO | WO 2013/104897 A1 | 7/2013 |
| WO | WO 2013/122888 A2 | 8/2013 |
| WO | WO 2013/184845 A1 | 12/2013 |
| WO | WO 2014/089365 A1 | 6/2014 |
| WO | WO 2014/107535 A1 | 7/2014 |
| WO | WO 2014/107536 A1 | 7/2014 |
| WO | WO 2014/110442 A1 | 7/2014 |
| WO | WO 2014/144380 A1 | 9/2014 |
| WO | WO 2014/151958 A1 | 9/2014 |
| WO | WO 2015/171398 A1 | 11/2015 |
| WO | WO 2015/171430 A1 | 11/2015 |
| WO | WO 2015/191907 A1 | 12/2015 |
| WO | WO 2016/003929 A1 | 1/2016 |
| WO | WO 2016/065282 A1 | 4/2016 |

OTHER PUBLICATIONS

Cunha, "Meropenem in elderly and renally impaired patients", Int'l J Antimicro Agents (1998) 10: 107-117.

Dunetz et al., "Large-scale applications of amide coupling reagents for the synthesis of pharmaceuticals", Org Process Res Develop. (2016) 20(2): 140-177.

Eggen et al., "Total synthesis of cryptophycin-24 (Arenastatin A) amenable to structural modifications in the C16 side chain", J Org Chem. (2000) 65(23): 7792-7799; and Supporting documents, 22 pages.

Gunanathan et al., "Ruthenium catalyzed hydroboration of terminal alkynes to Z vinylboronates", J Am Chem Soc. (2012) 134(35): 14349-14352; Supporting Information, 32 pages.

Hall D.G., [Ed], Boronic Acids [vol. 2]: Preparations and applications in Organic Synthesis, Medicine and Materials, Wiley-VCH, Weinheim, 2nd Edition (2011); TOC.

Hartung et al., "Highly Z-selective and Enantioselective Ring Opening/Cross Metathesis Catalyzed by Resolved Stereogenic-At—Ru Complex", J Am Chem Soc. (Jul. 2013) 135(28): 10183-10185.

He et al., "Ligand-promoted borylation of C(sp3)—H bonds with palladium(II) catalysts", Angew Chem Int Ed., (2016) 55(2): 785-789.

Hoveyda A., "Evolution of catalytic stereoselective olefin metathesis: From ancillary transformation to purveyor of stereochemical identity", J Org Chem. (Jun. 2014) 79(11): 4763-4792.

Hu et al., "Ag(I)-catalyzed C—H borylation of terminal alkynes", Tetrahedron (2014) 70: 5815-5819.

Ishiyama et al., "Palladium(0)-catalyzed cross-coupling reaction of alkoxydiboron with haloarenes: A direct procedure for arylboronic esters", J Org Chem. (1995) 60(23): 7508-7510; Supporting Information, 35 pages.

Jang et al., "Copper-catalyzed trans-hydroboration of terminal aryl alkynes: Stereodivergent synthesis of alkenylboron compounds. Org Letts. (2016) 18(6): 1390-1393; Supporting Information, Supporting Information, 37 pages.

Kuang et al., "Convenient and stereoselctive synthesis of (Z)-1-bromo-1-alkenes by microwave-induced reaction", Tetrahedron Letts. (2001) 42(23): 3893-3896.

Larock R. [Ed.] *Comprehensive Organic Transformations*, VCH Publishers 1989; TOC, 11 pages.

Lebel et al., "Boc-protected amines via a mild and efficient one-pot Curtius rearrangement", Org Letts. (2005) 7(19): 4107-4110.

Lieberman H.A. [Ed] *Pharmaceutical Dosage Forms—Tablets*; Marcel Dekker, Inc. (1989) 2nd Ed; TOC; 7 pages.

Lin et al., "Enantioselective syn and anti homocrotylation of aldehydes: Application to the formal synthesis of spongidepsin", J Am Chem Soc. (2015) 137(40): 13176-13182; Supporting Information, 177 pages.

Luithle et al., "Synthesis of enantiomerically pure cis-cyclopropylboronic esters", Eur J Org Chem. (2000) 14: 2557-2562.

Matteson, "Boronic Esters in Asymmetric Synthesis", J Org Chem. (Oct. 2013) 78(20): 10009-10023.

McOmie J.R.W. [Ed], *Protective Groups in Organic Chemistry*, Plenum Press, London & New York (1973); TOC, 3 pages.

Mkhalid et al., "C—H activation for the construction of C—B bonds", Chem Rev. (2010) 110(2): 890-931.

Molander et al., "Highly stereoselective synthesis of cis-alkenyl pinacolboronates and potassium cis-alkenyltrifluoroborates via a hydroboration/protodeboronation approach", J Org Chem. (2008) 73(17): 6841-6844.

(56) References Cited

OTHER PUBLICATIONS

Mori et al., "Synthesis of 1,3-dienes from alkynes and ethylene: Acetic acid 2-methylene-3-phenethylbut-3-enyl ester", Org Synth. (2005) 81: 1-13.
Munar et al., "Drug Dosing Adjustments in Patients with Chronic Kidney Disease", Am Fam Physician (May 2007) 75(1): 1487-1496.
Noguchi et al., "Boron-masking strategy for the selective synthesis of oligoarenes via iterative Suzuki-Miyaura coupling", J Am Chem Soc. (2007) 129(4): 758-759; Supporting Information, 46 pages.
Overman et al., "Organic Synthesis—Working with Hazardous Chemicals", Org Synth. (1990) 68: 182; 5 pages.
Paquette L.A. [Ed.] *Encyclopedia of Reagents for Organic Synthesis*, vol. 1; J. Wiley & Sons (1995); Cover Only.
Pellissier, H., "Recent developments in asymmetric cyclopropanation", Tetrahedron (2008) 64(30-31): 7041-7095.
Pietruszka et al., "Enantiomerically pure cyclopropylamines from cyclopropylboronic esters", Eur J Org Chem. (2009) 34: 5998-6008.
Roche, E.B. (Ed.)., Bioreversible Carriers in Drug Design: Theory and Application. New York: Pergamon Press (1987); pp. 14-21.
Sawant et al., "Synthesis of the C1-C13 Fragment of Biselyngbyaside", Synlett (2011) 20: 3002-3004.
Scriven et al., "Azides: Their preparation and synthetic uses", Chem Rev. (1988) 88(2): 297-368.
Singer et al., "Catalytic, enantioselective acetate aldol additions to alpha-, beta-ynals: Preparation of optically active propargylic alcohols", Tetrahedron (1998) 54(25): 7025-7032.
Sun et al., "A method for the deprotection of alkylpinacolyl boronate esters", J Org Chem. (2011) 76(9): 3571-3575; Supporting Information, 8 pages.
Voituriez et al., "Preparation of a storable zinc carbenoid species and its application in cyclopropanation, chain extension, and [2,3]-sigmatropic rearrangement reactions", J Org Chem. (2010) 75(4): 1244-1250; Supporting Information, 20 pages.
Wong et al., "A chemoselective Reformatsky-Negishi approach to α-haloaryl esters", Tetrahedron (2014) 70(7): 1508-1515.
Zhu et al., "Design, preparation, x-ray crystal structure, and reactivity of o-alkoxyphenyliodonium bis(methoxycarbonyl)methanide, a highly soluble carbene precursor", Org Lett. (2012) 14(12): 3170-3173; Supporting Information, 76 pages.
International Search Report and Written Opinion dated Aug. 25, 2015 for Application No. PCT/US2015/031400, filed May 18, 2015.
Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.
Adediran et al., "A 'cephalosporin-like' cyclic depsipeptide: Synthesis and reaction with beta-lactam-recognizing enzymes", Bioorg Med Chem Lett. (1999) 9(3):341-346.
Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.
Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.
Allen et al., "Ansel's Pharmaceutical Dosage Forms and Drug Delivery Systems", 8th Edition (2004) TOC only.
American Chemical Society. STN Chemical Database Registry RN: 1226917; Jun. 2010; 2 pages.
Arya et al., "Advances in asymmetric enolate methodology", Tetrahedron (2000) 56:917-947.
Babic et al., "What's new in antibiotic resistance? Focus on beta-lactamases", Drug Res Updates (2006) 9:142-156.
Bassetti et al., "New antibiotics for bad bugs: where are we?", Ann Clin Microbiol Antimicrob. (2013) 12:22-36.
Becker, Daniel E., "Antimicrobial Drugs", Anesth Prog (2013) 60:111-123.
Beenen et al., "Asymmetric copper catalyzed synthesis of alpha-amino boronate esters from N-tert-butanesulfinyl aldimines", J Am Chem Soc. (2008) 130(22):6910-6911.

Biedrzycki et al., "Derivatives of tetrahedral boronic acids", J. Organomet. Chem. (1992) 431:255-270.
Bou et al., "Cloning, nucleotide sequencing, and analysis of the gene encoding an AmpC beta-lactamase in Acinetobacter baumannii", Antimicrob Agents Chemother (2000) 44(2):428-432.
Bou et al., "OXA-24, a novel class D beta-lactamase with carbapenemase activity in an Acinetobacter baumannii clinical strain", Antimicrob Agents Chemother (2000) 44(6):1556-1561 and Erratum: Antimicrob Agents Chemother. (2006) 50(6) 2280.
Brabez et al., "Design,synthesis, and biological studies of efficient multivalent melanotropin ligands: tools toward melanoma diagnosis and treatment", J Med Chem. (2011) 54(20):7375-7384.
Brosz et al., "Resolution of alpha-aminoboronic esters by diastereoselective crystallization with pinanediols. Confirmation by x-ray analysis", Tetrahedron: Asymmetry (1997) 8(9):1435-1440.
Bush et al., "Minireview: Updated Functional Classification of beta-Lactamases," Antimicrob Agents Chemo. (2010) 54(3):969-976.
CAS Registry Nos. 69190-59/60 (2-(bis(phenylthio)methyl)-4,4,5,5-tetramethyl-1,3,2-dioxaborolane) and 69190-60-9 (2-(bis(phenylthio)methyl)-1,3,2-dioxaborinane) Scheme 18 (2015); 2 pages.
CAS Registry No. 105892-95-3 Boronic acid [1-(phenylsulfonyl)heptyl]-, dimethyl ester (2015); 2 pages.
Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.
Chemicalland21.com. "Meglumine", Jun. 7, 2011. Downloaded from </www.chemicalland21.com/lifescience/phar/N-METHYL-D-GLUCAMINE.htm>; 2 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2), 64 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2), 88 pages.
Clinical Trial NCT02168946, "A Phase 3, Multi-Center, Randomized, Open-Label Study of Carbavance (Meropenem/RPX7009) Versus Best Available Therapy in Subjects with Selected Serious Infecations Due to Carbapenem-Resistant Enterobacteriaceae", 6. Oct. 2014; retrieved online from URL:https://clinicaltrials.gov/archive/NCT02168946/20140_10_06.
Conte et al., "Intrapulmonary pharmacokinetics and pharmacodynamics of meropenem", Int J Antimicrob Agents (Dec. 2005) 26(6):449-456.
Coppa et al., "A Facile, Convenient and Selective Homolytic Carbamolylation of Heteroaromatic Bases", Heterocycles (1993) 36(12):2687-2696.
Coutts et al., "Two Efficient Methods for the Cleavage of Pinanediol Boronate Esters Yielding the Free Boronic Acids", Tetrahedron Lett. (1994) 35(29):5109-5112.
Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.
Darses et al., "Potassium Organotrifluoroborates: New Perspectives in organic Synthesis", Chem Rev. (2008) 108:288-325.
Davoli et al., "Enantioselective total synthesis of (−)-microcarpalide", Tetrahedron (2005) 61:4427-4436.
de Meijere A. [Ed], Science of Synthesis—vol. 24; "Three Carbon-Heteroatom Bonds: Ketene Acetals and Yne-X Compounds", TOC 46 pages.
Di Gioia et al., "Optically Pure N-Hydroxy-O-triisopropylsilyl-alpha-L-amino Acid Methyl Esters from AlCl3-Assisted Ring Opening of Chiral Oxaziridines by Nitrogen Containing Nucleophiles", J Org Chem. (2005) 70(25):10494-10501.
Drawz et al., "Three Decades of beta-Lactamase Inhibitors", Clin Microbiol Reviews (Jan. 2010) 23(1):160-201.
Eidam et al., "Design, synthesis, crystal structures and antimicrobial activity of sulfonamide boronic acids as beta-lactamase inhibitors", J Med Chem. (2010) 53(21):7852-7863.

(56) References Cited

OTHER PUBLICATIONS

Eissenstat et al., "Aminoalkylindoles: Structure-Activity Relationships of Novel Cannabinoid Mimetics", J Med Chem. (1995) 38(16):3094-3105.
El Nezhawy et al., "Synthesis and antioxidant activity of some thiazolidin-4-one derivatives", Springer; Chemical Monthly/ Monatshefte für Chemie (2009) 140(5):531-539.
Endo et al., "Chemoselective Suzuki coupling of diborylmethane for facile synthesis of benzylboronates", Org Lett. (2011) 13(13):3368-3371.
Fan, et al. (2009): STN International HCAPLUS database, Columbus (OH), accession No. 2009: 425839; 6 pages.
Farquhar et al., "Intensely potent doxorubicin analogues: structure-activity relationship", J. Med. Chem. (1998) 41(6):965-972.
Ghosh et al., "Enantioselective total synthesis of (+)-largazole, a potent inhibitor of histone deacetylase", Org Lett. (2008) 10(17):3907-3909.
Giroux, A., "Synthesis of benzylic boronates via palladium-catalyzed cross-coupling reaction of bis(pinacolato)diboron with benzylic halides", Tetrahedron Lett. (2003) 44:233-235.
Gorovoy et al., "Boron-Containing Peptidomimetics—A Novel Class of Selective Anti-tubercular Drugs", Chem Biol Drug Des. (Jan. 2013) 81(3):408-413.
Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.
Graham et al., "D is for Drugs", Chemistry & Industry, Mar. 19, 2013, pp. 28-30, Downloaded from http://www.concertpharma.com/wp-content/uploads/2014/12/ChemistryIndustry-0313.pdf; 3 pages.
Greene, et al., "*Greene's Protective Groups in Organic Synthesis*", 4th Edition, (2007); pp. 774, 785 & 787.
Hama et al., "Palladium-Catalyzed alpha-Arylation of Zinc Enolates of Esters: Reaction Conditions Conditions and Substrate Scope", J Org Chem. (2013) 78(17):8250-8266.
Hecker et al., "Discovery of a Cyclic Boronic Acid beta-Lactamase Inhibitor (RPX7009) with Utility vs Class A Serine Carbapenemases", J Med Chem. (Mar. 2015) 58:3682-3692.
Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.
Inglis et al., "Observations on the Deprotection of Pinanediol and Pinacol Boronate Esters via Fluorinated Intermediates", J Org Chem. (2010) 75(2):468-471.
Ishii et al, "In vitro potentiation of carbapenems with ME1071, a Novel metallo-β-lactamase inhibitor, against metallo-β-lactamase producing pseudomonas aeruginosa clinical isolates." Antimicrob. Agents Chemother. doi:10.1128/AAC.01397-09 (2010) 54(9):3625-3629.
Ito et al., "An efficient constructive method for a tricyclic system: an important intermediate for the synthesis of tricycloclavulone", Tetrahedron Lett. (2003) 44:1259-1261.
Jadhav et al., "Direct synthesis of [alpha-[(tert-Butoxycarbonyl)amino]alkyl]-boronates from (alpha-Haloalkyl)boronates", Org Chem. (1996) 61(22):7951-7954.
Jagannathan et al., "Synthesis of Boronic Acid Analogues of alpha-Amino Acids by Introducing Side Chains as Electrophiles", J Org Chem. (2001) 66(19):6375-6380.
Jiang et al., "A Practical Synthesis of Cefcapene Pivoxil", Synthesis (2012) 44:207-214.
Johnson et al., "A drug targeting motif for glycosidase inhibitors: An iminosugar-boronate shows unexpectedly selective beta-galactosidase inhibition", Tetrahed Lttrs. (2002) 43(49):8905-8908.
Kabalka et al., "Synthesis of a series of bomonated unnatural cyclic amino acids as potential boron neutron capture therapy agents", Appl Organomet Chem. (2008) 22(9):516-522.

Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", Chem Letts. (1993) 22(5):845-848.
Kawamorita et al., "Synthesis of Primary and Secondary Alkylboronates through Site-Selective C(sp3)-H Activation with Silica-supported Monophosphine-Ir Catalysts", J Am Chem Soc. (2013) 135(8):2947-2950.
Kikuchi et al., "Comparison of the Pharmacodynamics of Biapenem in Bronchial Epithelial Lining Fluid in Healthy Volunteers Given Half-Hour and Three-Hour Intravenous Infusions", Antimicrob Agents Chemother. (Jul. 2009) 53(7):2799-2803.
Kint et al., "New-found fundamentals of bacterial persistence", Trends Microbiol. (2012) 20(12):577-585.
Kose et al., "Synthesis of photochromic 2,3-bis(5-methyl-2-phenyl-4-thiazonlyl)-1,4-napththoquinone derivatives", J Photochem Photobiol. A: Chemstry. (2011) 219(1):58-61.
Kotha et al., "Recent applications of the suzuki-miyaura cross-coupling reaction in organic synthesis", Tetrahedron (2002) 58:9633-9695.
Kumar et al., "Synthesis of intermediates for the lactone moiety of mevinic acids via tellurium chemistry", J. Org. Chem., (1994) 59(17):4760-4764.
Kumar et al., "Development of Practical Methodologies for the Synthesis of Functionalized Benzoboroxoles", Tetrahedron Lett. (Aug. 25, 2010) 51(34):4482-4485.
Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.
Kuti et al., "Use of Monte Carlo simulation to design an optimized pharmacodynamic dosing strategy for meropenem", J Clin Pharmacol. (Oct. 2003) 43(10:1116-1123.
Laitar et al., "Catalytic diboration of aldehydes via insertion into the copper-boron bond", J Am Chem Soc. (2006) 128(34):11036-11037.
Lapuebla et al., "Activity of Meropenem Combined with RPX7009, a Novel beta-Lactamase Inhibitor, against Gram-Negative Clinical Isolates in New York City", Antimicrob Agents Chemother. (Aug. 2015) 59(8):4856-4860.
Lee et al., "Vicinal Diboronates in High Enantiomeric Purity through Tandem Site-Selective NHC-Cu-Catalyzed Boron-Copper Additions to Terminal Alkynes", J Am Chem Soc. (Dec. 2009) 131(51):18234-18235.
Li et al, "Novel macrocyclic HCV NS3 protease inhibitors derived from α-amino cyclic boronates", Bioorganic Med Chem Lett. (2010) 20:5695-5700.
Li et al., "Synthesis and evaluation of novel alpha-amino cyclic boronates as inhibitors of HCV NS3 protease", Bioorg Med Chem Lett. (2010) 20:3550-3556.
Li et al., "Stereoselective total synthesis of etnangien and etnangien methyl ester", J Org Chem. (2010) 75(8):2429-2444.
Liang et al., "The Efficient Copper(I) (Hexabenzyl)tren Catalyst and Dendritic Analogues for Green "Click" Reactions between Azides and Alkynes in Organic Solvent and in Water: Positive Dendritic Effects and Monometallic Mechanism", Advance Syn Catal. (2011) 1353(18): 3434-3450.
Lima et al., "Bioisosterism: A Useful Strategy for Molecular Modification and Drug Design", Curr Med Chem. (2005) 12:23-49.
Liu et al., "Selective Protein tyrosine phosphatase 1B inhibitors: Targeting the second phosphotyrosine binding site with non-carboxylic acid-containing ligands", J Med Chem. (2003) 46(16):3437-3440.
Liu et al., "Application of Stereoselective Ether Transfer to the Synthesis of Isotactic Polyethers", J Org Chem. (2010) 75(12):3953-3957.
Livermore et al., "Activities of NXL104 combinations with Ceftazidime and Aztreonam against Carbapenemase-producing Enterobacteriaceae", Antimicr Agents Chemother. (2011) 55(1):390-394.
Livermore et al., "Activity of biapenem (RPX2003) combined with the boronate beta-lactamase inhibitor RPX7009 against

(56) References Cited

OTHER PUBLICATIONS carbapenem-resistant Enterobacteriaceae", J Antimicrob Chemother. (Aug. 2013) 68(8):1825-1831.
Lodise et al., "Penetration of meropenem into epithelial lining fluid of patients with ventilator-associated pneumonia", Antimicrob Agents Chemother. (Apr. 2011) 55(4):1606-1610.
Malfertheiner et al., "Current concepts in the management of Helicobacter pylori infection: the Maastricht III Consensus Report", Gut (2007) 56(6):772-781.
Matteson et al., "Iodomethaneboronic Esters and Aminomethaneboronic Esters", J Organomet. Chem. (1979) 170:259-264.
Matteson et al., "A Directed Chiral Synthesis of Amino Acids from Boronic Esters", Tetrahedron Lett. (1987) 28(39):4499-4502.
Matteson, D.S., "Asymmetric Synthesis with Boronic Esters", Acc Chem Res. (1988) 21(8):294-300.
Matteson, "Boronic esters in stereodirected synthesis", Tetrahedron (1989) 45(7):1859-1885.
Matteson et al., "A stereospecific convergent coupling of nucleophilic and electrophilic chiral carbons", J. Am. Chem. Soc. (1989) 111:4399-4402.
Matteson et al., "Synthesis of asymmetrically deuterated glycerol and dibenzylglyceraldehyde via boronic esters", J. Am. Chem. Soc. (1990) 112:3964-3969.
Matteson et al., "Alkoxyalkyl)boronic Ester Intermediates for Asymmetrric Synthesis", Organometallics (1996) 15:152-163.
Matteson, "Alpha-Halo Baronic Esters in Asymmetric Synthesis", Tetrahedron (1998) 54(36):10555-10607.
Matteson et al., "Glass-Catalyzed Conversion of Boronic Esters of Asymmetric Diols to Diol Sulfites and Amine Complexes of Boron Halides", Oranometallics (2001) 20(13):2920-2923 & supporting Information (9 pages).
Matteson et al., "Cesium Alkyltrifluoroborates from Asymmetric Boronic Esters", Synlett (Jul. 2006) 20:3501-3503.
Matteson et al., "Synthesis of a (Beta-acetamido-alpha-acetoxyethyl) boronic ester via azido boronic esters", J Organomet Chem. (2008) 693:2258-2262.
Meanwell, "Synopsis of some recent tactical application of bioisosteres in drug design", J. Med. Chem. (2011) 54:2529-2591.
Mendoza et al., "Bis(phenylthio)methaneboronic Esters as Sources of Carbanions and Ketene Thioacetals", J Org Chem. (1979) 44(8):1352-1354.
Micalizio et al., "A Boronic Ester Annulation Strategy for Diversity-Oriented Organic Synthesis", Angew Chem Int Ed Engl. (2002) 41(1):152-154.
Montalbetti et al., "Amide bond formation and peptide coupling", Tetrahedron (2005) 61:10827-10852.
Montefour et al., "Acinetobacter baumannii: an emerging multidrug-resistant pathogen in critical care", Crit Care Nurse (2008) 28(1):15-25.
Morandi et al., "Structure-based optimization of cephalothin-analogue boronic acids as beta-lactamase inhibitors", Bioorg Med Chem. (2008) 16(3):1195-205. Epub Nov. 7, 2007.
Nema et al., "Excipients and Their Role in Approved Injectable Products: Current Usage and Future Directions", PDA J Pharm Sci Technol. (2011) 65(3):287-332.
Ness et al., "Structure-based design guides the improved efficacy of deacylation transition state analogue inhibitors of TEM-1 beta-Lactamase", Biochemistry (2000) 39(18):5312-5321.
Nordmann et al., How to Detect NDM-1 Producers, J. Clin. Micro. (2011) 49:718-721.
Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.
Patani et al., "Bioisosterism: A Rational Approach in Drug Design", Chem Rev. (1996) 96:3147-3176.
Paterson et al., "Extended-Spectrum beta-Lactamases: a Clinical Update", Clin Microbiol Rev. (2005) 18(4):657-686

Perez et al., "Why are we afraid of Acinetobacter baumannii?", Expert Rev Anti Infect Ther. (2008) 6(3):269-71.
Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34):11825-11827.
Powell et al., "Compendium of excipients for parenteral formulations", PDA J Pharm Sci Technol. (1998) 52(5):238-311.
Reissig et al.,"High diastereoselection in the alkylation of siloxy-substituted methyl cyclopropanecarboxylates: consequence of a pyramidal ester enolate anion?", J. Am. Chem. Soc. (1982) 104:1735-1737.
Robak et al., "Synthesis and applications of tert-butanesulfinamide", Chem Rev. (2010) 110(6):3600-3740.
Rodriguez-Martinez et al., "VIM-19, a Metallo-beta-lactamase with increased Carbapenemase Activity from *Escherichia coli* and Klebsiella pneumoniae", Antimicro Agents Chemother. (2010) 54(1):471-476.
Sabet et al., "In Vivo Efficacy of Carbavance (Meropenem/RPX7009) Against KPC-producing Enterobacteriaceae", Abstracts of the 54th Interscience Conference on Antimicrobial Agents and Chemotherpy (Sep. 5-9, 2014) F-958; 3 pages.
Sawyer et al., "Physical properties and synthetic utility of a-alkoxyorganolithium species as studied through ligand selectivity in tin-lithium exchange", J. Am. Chem. Soc. (1988) 110:842-853.
Selander et al., "Palladium-catalyzed allylic C—OH functionalization for efficient synthesis of functionalized allylsilanes", J Am Chem Soc. (2011) 133(3):409-411.
Shaffer, Robyn Kroop, "The Challenge of Antibiotic-Resistant *Staphylococcus*: Lessons from Hospital Nurseries in the mid-20th Century", Yale J Biol Med. (2013) 86:261-270.
Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.
Singh et al., "Asymmetric Homologation of Boronic Esters Bearing Azido and Silyloxy Substituents", J Org Chem. (2000) 65(20):6650-6653 and Erratum: J Org Chem. (2001) 66(22):7560.
Sliwka et al., "Synthetic Sulfur Carotenoids II: Optically Active Carotenoid Thiols", Tetrahedron: Asymmetry (1993) 4(3):361-368.
Solladié et al., "First Stereocontrolled Synthesis of the (3S,5R,7R,10R,11R)-C1-C13 Fragment of Nystatin A(1)", J Org Chem. (1999) 64(15):5447-5452.
Souto et al., "Synthesis and biological characterization of the histone deacetylase inhibitor largazole and c7-modified analogues", J. Med. Chem. (2010) 53(12):4654-4667.
Spiegel et al., "CP-263,114 synthetic studies. Construction of an isotwistane ring system via rhodium carbenoid C—H insertion", Tetrahedron (2002) 58:6545-6554.
Sun et al., "Programmed Synthesis of a Contiguous Stereotriad Motif by Triple Stereospecific Reagent-controlled Homologation", Org Lttr. (Jul. 2013) 15(17):4500-4503.
Teo et al., "Efficient and highly aldehyde selective Wacker oxidation", Org Lett. (2012) 14(13):3237-3239.
Theuretzbacher et al., "Update on antibacterial and antifungal drugs—can we master the resistance crisis?", Curr Opin Pharmacol. (2011) 11:429-432.
Vasil'ev et al., (1977): STN International HCAPLUS database, Columbus (OH), accession No. 1977: 72730; 1 page.
Vitor et al., "Rhenium(I)- and technetium(I) tricarbonyl complexes anchored by bifunctional pyrazole-diamine and pyrazole-dithioether chelators", J Organometal Chem (2004) 689(25):4764-4774.
Waley, Stephen G., "A quick method for the determination of inhibition constants", Biochem J. (1982) 205(3):631-633.
Walsh et al., "Metallo-beta-Lactamases: the Quiet before the Storm?", Clin Microbiol Rev. (2005) 18(2):306-325.
Wang et al., "Recognition and resistance in TEM beta-lactamase", Biochemistry (2003) 42(28):8434-8444.
Webb et al., "Metal catalysed hydroboration of vinyl sulfides, sulfoxides, sulfones, and sulfonates", J Mol Cat A: Chem. (2007) 275:91-100.

(56) References Cited

OTHER PUBLICATIONS

Wohlrab et al., "Total synthesis of plusbacin A3: a depsipeptide antibiotic active against vancomycin-resistant bacteria", J. Am. Chem. Soc. (2007) 129:4175-4177.

Xia et al., "Synthesis and SAR of novel benzoxaboroles as a new class of beta-lactamase inhibitors", Bioorg Med Chem Lett. (2011) 21:2533-2536.

Xie et al., "Group-assisted purification (GAP) chemistry for the synthesis of Velcade via asymmetric borylation of N-phosphinylimines", Beilstein J Org Chem (Mar. 2014) 10:746-751.

Yamamoto et al., "Iridium-catalyzed hydroboration of alkenes with pinacolborane", Tetrahedron (2004) 60:10695-10700.

Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.

Yuen et al., "Deprotection of pinacolyl boronate esters via hydrolysis of intermediate potassium trifluoroborates", Tetrahed Lttr. (2005)46(46):7899-7903.

\* cited by examiner

BORONIC ACID DERIVATIVES AND THERAPEUTIC USES THEREOF

CROSS-REFERENCE TO RELATED APPLICATIONS

This application is the U.S. National Phase of International Application No. PCT/US2015/031400 entitled Boronic Acid Derivatives And Therapeutic Uses Thereof, filed May 18, 2015 and published on Nov. 26, 2015 as WO 2015/179308, which claims the benefit of U.S. Provisional Application No. 62/000,400, filed May 19, 2014, the disclosure of which is incorporated herein by reference in its entirety.

BACKGROUND OF THE INVENTION

Field of the Invention

The present invention relates to the fields of chemistry and medicine. More particularly, the present invention relates to boronic acid antimicrobial compounds, compositions, their preparation, and their use as therapeutic agents.

Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of anti-bacterial therapy. The increase in antibiotic resistant strains has been particularly common in major hospitals and care centers. The consequences of the increase in resistant strains include higher morbidity and mortality, longer patient hospitalization, and an increase in treatment costs.

Various bacteria have evolved β-lactam deactivating enzymes, namely, β-lactamases, that counter the efficacy of the various β-lactam antibiotics. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K.; et al. Crit. Care Nurse 2008, 28, 15; Perez, F. et al. Expert Rev. Anti Infect. Ther. 2008, 6, 269; Bou, G.; Martinez-Beltran, J. Antimicrob. Agents Chemother. 2000, 40, 428. 2006, 50, 2280; Bou, G. et al, J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other Enterobacteriaceae, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in *Pseudomonas aeruginosa*. Efflux pump over expression combined with hyperproduction of the ampC β-lactamase can also result in resistance to a carbapenem such as meropenem.

Thus, there is a need for improved β-lactamase inhibitors.

SUMMARY OF THE INVENTION

Some embodiments disclosed herein include a compound having the structure of formula (I) or formula (II):

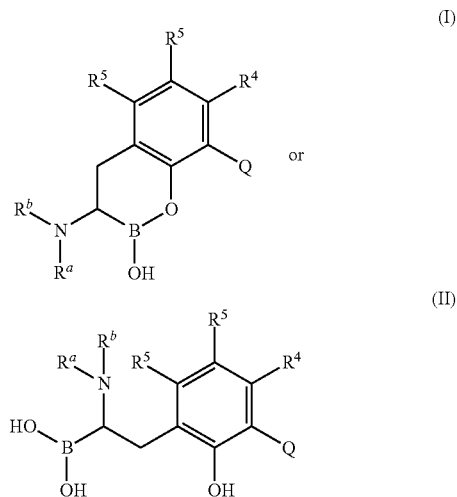

or pharmaceutically acceptable salts thereof, wherein:

$R^a$ is independently selected from the group consisting of hydrogen; $C_1$-$C_6$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_{3-7}$cycloalkyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; 5-10 membered heteroaryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 3-10 membered heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and $R^b$ is independently selected from the group consisting of hydrogen; —OH; —C(O)G; —C(O)OG; —S(O)$_2$G; —C($=NR^1R^2$)G; —C($=NOR^3$)G; $C_1$-$C_6$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; —O—$C_1$-$C_6$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; —S—$C_1$-$C_6$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_3$-$C_8$ cycloalkyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$ aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; 5-10 membered heteroaryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 3-10 membered heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; or $R^a$ and $R^b$ together with the nitrogen to which they are attached form a 5-8 membered heterocyclic or heteroaryl ring, optionally comprising additional 1-3 heteroatoms selected from O, S or N;

G is selected from the group consisting of hydrogen; —NR$^1$R$^2$; —CH$_2$N$_3$; —CH$_2$CN; —C(O)NR$^1$R$^2$; —CH(=CH—R$^6$)R$^7$; —CH$_2$C(O)NR$^1$R$^2$; —CH$_2$S(O)$_2$ NR$^1$R$^2$; —(CH$_2$)$_n$—Y—Z; —O—(CH$_2$)—C(O)NR$^1$R$^2$; —SR$^3$; —P(O)R$^1$R$^2$; —CH$_2$NR$^1$C(O)R$^6$; —C($=NOR^3$)—Z; —C(O)OR$^3$; —C(O)—Z; —S(O)$_2$R$^3$; —C(O)NR$^1$OR$^3$; —NR$^1$(OR$^3$); —NR$^1$C(O)R$^6$; —NR$^1$C(O)NR$^2$R$^{1a}$; —NR$^1$C(O)OR$^3$; —NR$^1$S(O)R$^3$; —NR$^1$S(O)$_2$NR$^2$R$^{1a}$; —NR$^1$NR$^2$R$^{1a}$; —C(O)NR$^1$NR$^2$R$^{1a}$; —S(O)$_2$NR$^1$NR$^2$R$^{1a}$; —C($=NR^1$)R$^6$; —C($=NR^1$)NR$^2$R$^{1a}$; —NR$^1$CR$^6$($=NR^2$); —NR$^1$C($=NR^2$)NR$^{1a}$R$^{2a}$; $C_1$-$C_{10}$ alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_2$-$C_{10}$alkenyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_2$-$C_{10}$alkynyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_3$-$C_7$ carbocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; 5-10 membered heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 5-10 membered heteroaryl optionally substituted with one or more substituents selected from the group consisting of $C_1$-$C_6$alkyl, $C_6$-$C_{10}$aryl, 5-10 membered heteroaryl, —O—$C_1$-$C_6$alkyl, —S—$C_1$-$C_6$alkyl, amino, —C(O)-amino, —S(O)$_2$-amino, hydroxy, cyano, azido, and halogen;

n is 0 to 3;

Y is selected from a group consisting of —S—, —S(O)—, —S(O)$_2$—, —O—, —C(O)—, —CR$^6$R$^7$—, —O—C R$^6$R$^7$—, and —NR$^1$—;

Z is selected from the group consisting of hydrogen; CONR$^1$R$^2$; —COOH; $C_1$-$C_6$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, —COOH, and halogen; $C_2$-$C_{10}$ alkenyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, —COOH, and halogen; $C_2$-$C_{10}$ alkynyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, —COOH, and halogen; $C_3$-$C_7$carbocyclyl optionally substituted with one or more substituents selected from the group consisting of $C_1$-$C_6$alkyl, —O—$C_1$-$C_6$alkyl, amino, —C(O)-amino, —S(O)$_2$-amino, hydroxy, cyano, azido, —COOH, and halogen; 3-10 membered heterocyclyl optionally substituted with one or more substituents selected from the group consisting of $C_1$-$C_6$alkyl, —O—$C_1$-$C_6$alkyl, amino, —C(O)-amino, —S(O)$_2$-amino, hydroxy, cyano, azido, —COOH, and halogen; $C_6$-$C_{10}$ aryl optionally substituted with one or more substituents selected from the group consisting of $C_1$-$C_6$alkyl, —O—$C_1$-$C_6$alkyl, amino, —C(O)-amino, —S(O)$_2$-amino, hydroxy, cyano, azido, —COOH, and halogen; and 5-10 membered heteroaryl optionally substituted with one or more substituents selected from the group consisting of $C_1$-$C_6$alkyl, —O—$C_1$-$C_6$alkyl, amino, —C(O)-amino, —S(O)$_2$-amino, hydroxy, cyano, azido, —COOH, and halogen;

Q is a carboxylic acid, carboxylic acid prodrug moiety, or carboxylic acid isostere;

$R^1$, $R^2$, $R^{1a}$ and $R^{2a}$ are independently selected from the group consisting of —H; hydroxy; $C_1$-$C_{10}$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; —$C_2$-$C_{10}$alkenyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_2$-$C_{10}$alkynyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_3$-$C_7$ carbocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; 3-8 membered heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 5-10 membered heteroaryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen;

$R^3$ is hydrogen; hydroxy; $C_1$-$C_{10}$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, 5-10 membered heteroaryl, and halogen; —$C_1$-$C_{10}$alkyl-COOH optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_3$-$C_7$ carbocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; 3-8 membered heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 5-10 membered heteroaryl optionally substituted with one or more substituents selected from the group consisting of $C_1$-$C_6$alkyl, —S—$C_1$-$C_6$alkyl, amino, —C(O)-amino, —S(O)$_2$-amino, hydroxy, cyano, azido, and halogen;

$R^4$ is selected from the group consisting of hydroxy, —C(O)$R^6$, —C(O)$NR^1R^2$, —C(O)$NR^1OR^3$, —$NR^1C(O)R^6$, —$NR^1C(O)OR^3$, —$NR^1S(O)_2R^3$, —$NR^1S(O)_2NR^2R^{1a}$, —C(=$NR^1$)$R^6$, —C(=$NR^1$)$NR^2R^{1a}$, —$NR^1CR^6$(=$NR^2$), —$NR^1C$(=$NR^2$)$NR^{1a}R^{2a}$, halogen, —CF$_3$, $C_1$-$C_6$ alkenyl, $C_1$-$C_6$ alkynyl, $C_1$-$C_6$ heteroalkyl, $C_3$-$C_7$ carbocyclyl, 3-10 membered heterocyclyl, $C_6$-$C_{10}$ aryl, 5-10 membered heteroaryl, cyano, $C_1$-$C_6$ alkoxy($C_1$-$C_6$)alkyl, $C_6$-$C_{10}$ aryloxy, sulfhydryl (mercapto), and —(CH$_2$)$_m$—Y'—(CH$_2$)$_p$M';

m and p are independently 0 to 3;

Y' is selected from the group consisting of —S—, —S(O)—, —S(O)$_2$—, —P(O)$R^1$—, —O—, —CR$^6$R$^7$—, and —NR$^1$—;

M' is selected from the group consisting of hydrogen; hydroxy; —C(O)$NR^1R^2$; —C(O)$NR^1OR^3$; —$NR^1C(O)R^6$; —$NR^1C(O)NR^2R^{1a}$; —$NR^1C(O)OR^3$; —$NR^1S(O)_2R^3$; —$NR^1S(O)_2NR^2R^{1a}$; —C(=$NR^1$)$R^6$; —C(=$NR^1$)$NR^2R^{1a}$; —$NR^1CR^6$(=$NR^2$); —$NR^1C$(=$NR^2$)$NR^{1a}R^{2a}$; —COOH; $C_1$-$C_4$ alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_{3-10}$ cycloalkyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$ aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; 5 to 10 membered heteroaryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 4 to 10 membered heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen;

each $R^5$ is independently hydrogen, $C_1$-$C_6$alkyl, $C_2$-$C_6$ alkenyl, $C_2$-$C_6$ alkynyl, hydroxy, $OR^3$, —$SR^3$, halogen, amino, —C(O)-amino, —S(O)$_2$-amino, $C_3$-$C_7$ cycloalkyl, 3-8 membered heterocyclyl, and —CF$_3$; and each $R^6$ and $R^7$ are independently selected from the group consisting of hydrogen; hydroxy; amino; —C(O)-amino; —S(O)$_2$-amino; —O—$C_1$-$C_6$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; —S—$C_1$-$C_6$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_1$-$C_{10}$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_2$-$C_{10}$alkenyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_2$-$C_{10}$alkynyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_3$-$C_7$ cycloalkyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; 3-8 membered heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 5-10 membered heteroaryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen.

Other embodiments disclosed herein include a pharmaceutical composition comprising a therapeutically effective amount of a compound disclosed herein and a pharmaceutically acceptable excipient.

Some embodiments disclosed herein include a pharmaceutical composition comprising a therapeutically effective amount of a compound disclosed herein, a pharmaceutically acceptable excipient and one or more β-lactam antibacterial agents.

Other embodiments disclosed herein include a method of treating or preventing a bacterial infection, comprising administering to a subject in need thereof a compound disclosed herein.

DETAILED DESCRIPTION OF THE PREFERRED EMBODIMENT

In some embodiments, compounds that contain a boronic acid moiety are provided that act as antimicrobial agents and/or as potentiators of antimicrobial agents. Various embodiments of these compounds include compounds having the structures of Formulas I and II as described above or pharmaceutically acceptable salts thereof.

In some embodiments of Formulas I and II, $R^b$ is —C(O)G, —C(O)OG, —S(O)$_2$G, —C(=NR$^1$R$^2$)G or —C(=NOR$^3$)G.

Some embodiments of the compound of Formula (I) or (II) have the structure of Formula (Ia) or (IIa):

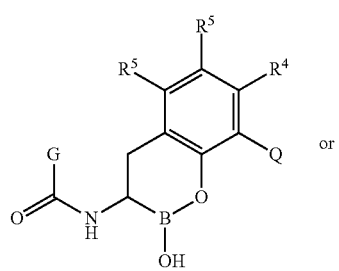

(Ia)

or

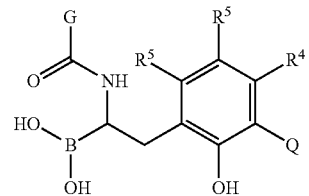

(IIa)

or pharmaceutically acceptable salts thereof, wherein:

G is selected from the group consisting of hydrogen; —NR$^1$R$^2$; —CH$_2$N$_3$; —CH$_2$CN; —C(O)NR$^1$R$^2$; —CH(=CH—R$^6$)R$^7$; —CH$_2$C(O)NR$^1$R$^2$; —CH$_2$S(O)$_2$NR$^1$R$^2$; —CH$_2$C(O)OR$^3$; —CH$_2$—Y—Z; —SR$^3$; —P(O)R$^1$R$^2$; $C_1$-$C_{10}$ alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_3$-$C_7$ carbocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; 5-10 membered heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 5-10 membered heteroaryl optionally substituted with one or more substituents selected from the group consisting of $C_1$-$C_6$alkyl, $C_6$-$C_{10}$aryl, 5-10 membered heteroaryl, —O—$C_1$-$C_6$alkyl, —S—$C_1$-$C_6$alkyl, amino, —C(O)-amino, —S(O)$_2$-amino, hydroxy, cyano, azido, and halogen;

$R^1$, $R^2$, $R^{1a}$, $R^{2a}$, $R^6$, and $R^7$ are each independently selected from the group consisting of hydrogen, hydroxy, and $C_1$-$C_4$alkyl; and $R^3$ is selected from the group consisting of hydrogen, hydroxy, $C_1$-$C_6$alkyl, $C_1$-$C_6$ cycloalkyl, and $C_1$-$C_6$heterocycle.

Some embodiments of compounds of Formula (I) or (II) have the structure of Formula (Ia):

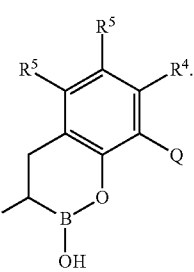

(Ia)

Some embodiments of compounds of Formula (I) or (Ia) have the stereochemistry as shown in the structure of Formula (Ia-1):

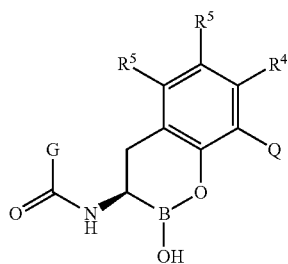

(Ia-1)

Some embodiments of compounds of Formula (I) or (Ia) have the stereochemistry as shown in the structure of Formula (Ia-2):

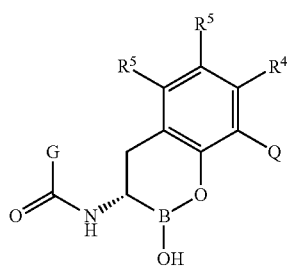

(Ia-2)

In some embodiments, $R^5$ is hydrogen.
In some embodiments, at least one $R^5$ is halogen.
In some embodiments, at least one $R^5$ is —F.
In some embodiments, at least one $R^5$ is —Cl.
In some embodiments, $R^4$ is selected from the group consisting of $C_1$-$C_6$alkyl, $C_2$-$C_6$ alkenyl, $C_2$-$C_6$ alkynyl, $C_3$-$C_7$ carbocyclyl, $C_1$-$C_6$ heteroalkyl, 5-10 membered heterocyclyl, $C_6$-$C_{10}$ aryl, 5-10 membered heteroaryl, cyano, —OH, —$OR^3$, —$SR^3$, —$S(O)_2M'$, —$P(O)R^1M'$, and halogen.
In some embodiments, $R^4$ is —$SO_3H$.
In some embodiments, $R^4$ is —$PO_3H_2$.
In some embodiments, $R^4$ is halogen.
In some embodiments, $R^4$ is F.
In some embodiments, $R^4$ is Cl, Me, —$CF_3$, or —$(CH_2)_m$-Y'—$(CH_2)_pM'$ wherein m and p are 0.
In some embodiments, $R^4$ is —$(CH_2)_m$-Y'—$(CH_2)_pM'$ wherein:
m is 0;
p is 0 to 3; and
Y' is O or S.
In some embodiments, M' is hydrogen; hydroxyl; —C(O)$NR^1R^2$; COOH; $C_1$-$C_4$ alkyl optionally substituted with one or more substituents selected from the group consisting of —O—$C_1$-$C_6$alkyl, —S—$C_1$-$C_6$alkyl, amino, —C(O)-amino, —$S(O)_2$-amino, hydroxy, cyano, azido, and halogen; $C_{3-10}$ cycloalkyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —$S(O)_2$-amino, hydroxy, cyano, azido, and halogen; $C_6$-$C_{10}$ aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —$S(O)_2$-amino, hydroxy, cyano, azido, and halogen; 5 to 10 membered heteroaryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —$S(O)_2$-amino, hydroxy, cyano, azido, and halogen; and 4 to 10 membered heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —$S(O)_2$-amino, hydroxy, cyano, azido, and halogen.

In some embodiments, $R^4$ is —O—C(O)N $R^1R^2$, and $R^1$ and $R^2$ in $R^4$ are each independently selected from hydrogen and hydroxy.

In some embodiments, $R^1$ is hydrogen and $R^2$ is hydrogen or hydroxy.

In some embodiments, $R^4$ is —S—$C_1$-$C_6$alkyl, —S—$C_1$-$C_6$ cycloalkyl, or —S—$C_1$-$C_6$heterocycle.

In some embodiments, $R^4$ is —S—$CH_3$.

In some embodiments, $R^4$ is

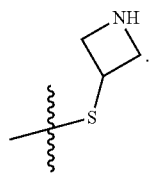 [SMILES: *SC1CNC1]

In some embodiments, $R^4$ is —O—$C_1$-$C_6$alkyl.
In some embodiments, $R^4$ is —$OCH_3$.
In some embodiments, $R^4$ is

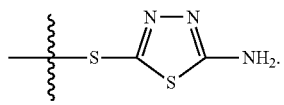 [SMILES: *Sc1nnc(N)s1]

In some embodiments, $R^4$ is —S—$CH_2$—C(O)—$NH_2$.
In some embodiments, $R^4$ is —S—$CH_2$—$CH_2$—OH.
In some embodiments, $R^4$ is

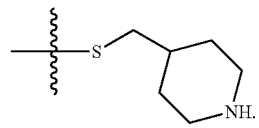

In some embodiments, $R^4$ is

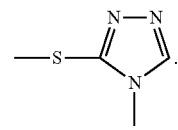

In some embodiments, $R^6$ and $R^7$ are independently selected from the group consisting of hydrogen, hydroxy, and —$C_1$-$C_4$alkyl.

In some embodiments, Q is COOR, and R is selected from the group consisting of hydrogen, $C_{1-9}$alkyl, —$CR^6R^7OC(O)C_{1-9}$alkyl, —$CR^6R^7OC(O)OC_{1-9}$alkyl, $CR^6R^7OC(O)C_{6-10}$ aryl, $CR^6R^7OC(O)OC_{6-10}$aryl, and

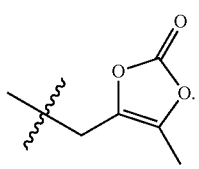 [SMILES: *Cc1oc(=O)oc1C]

In some embodiments, R is H.

In some embodiments, R is —CR$^6$R$^7$OC(O)C$_1$-C$_9$alkyl.

In some embodiments, R is —CH$_2$OC(O)CH$_3$, —CH$_2$OC(O)CH$_2$CH$_3$, —CH$_2$OC(O)CH$_2$CH$_2$CH$_3$, —CH$_2$OC(O)CH(CH$_3$)$_2$, or —CH$_2$OC(O)C(CH$_3$)$_3$.

In some embodiments, R is —CR$^6$R$^7$OC(O)OC$_1$-C$_9$alkyl, or

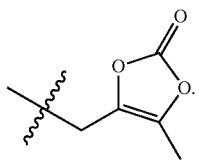

In some embodiments, R is —CH$_2$OC(O)OCH(CH$_3$)$_2$ or —CH$_2$OC(O)OCH$_2$CH$_3$.

In some embodiments, R is CR$^6$R$^7$OC(O)C$_{6-10}$aryl or CR$^6$R$^7$OC(O)OC$_{6-10}$aryl. In some embodiments, R is CH$_2$OC(O)OC$_6$H$_5$, In some embodiments, R is CH$_2$OC(O)C$_6$H$_5$, In some embodiments, G is H.

In some embodiments, G is —SO$_3$H.

In some embodiments, G is —PO$_3$H$_2$.

In some embodiments, G is is selected from the group consisting of C$_1$-C$_{10}$ alkyl optionally substituted with one or more substituents selected from the group consisting of —O—C$_1$-C$_6$alkyl, —S—C$_1$-C$_6$alkyl, amino, —C(O)-amino, —S(O)$_2$-amino, hydroxy, cyano, azido, and halogen; C$_{3-7}$ carbocyclyl optionally substituted with one or more substituents selected from the group consisting of C$_1$-C$_6$alkyl, —O—C$_1$-C$_6$alkyl, —S—C$_1$-C$_6$alkyl, amino, —C(O)-amino, —S(O)$_2$-amino, hydroxy, cyano, azido, and halogen; 5-10 membered heterocyclyl optionally substituted with one or more substituents selected from the group consisting of C$_1$-C$_6$alkyl, —O—C$_1$-C$_6$alkyl, —S—C$_1$-C$_6$alkyl, amino, —C(O)-amino, —S(O)$_2$-amino, hydroxy, cyano, azido, and halogen; C$_{6-10}$aryl optionally substituted with one or more substituents selected from the group consisting of C$_1$-C$_6$alkyl, —O—C$_1$-C$_6$alkyl, —S—C$_1$-C$_6$alkyl, amino, —C(O)-amino, —S(O)$_2$-amino, hydroxy, cyano, azido, and halogen; and 5-10 membered heteroaryl optionally substituted with one or more substituents selected from the group consisting of C$_1$-C$_6$alkyl, —C$_6$-C$_{10}$aryl, 5-10 membered heteroaryl, —O—C$_1$-C$_6$alkyl, —S—C$_1$-C$_6$alkyl, amino, —C(O)-amino, —S(O)$_2$-amino, hydroxy, cyano, azido, and halogen.

In some embodiments, G is 5-10 membered heteroaryl optionally substituted with one or more substituents selected from the group consisting of C$_1$-C$_6$alkyl, —C$_6$-C$_{10}$aryl, 5-10 membered heteroaryl, —O—C$_1$-C$_6$alkyl, —S—C$_1$-C$_6$alkyl, amino, —C(O)-amino, —S(O)$_2$-amino, hydroxy, cyano, azido, and halogen.

In some embodiments, G is

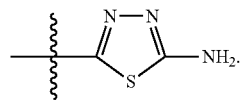 [SMILES: *c1nnc(N)s1]

In some embodiments, G is —NH$_2$.

In some embodiments, G is —C(O)NR$^1$R$^2$ and R$^1$ and R$^2$ in G are each independently selected from hydrogen and C$_1$-C$_6$alkyl.

In some embodiments, R$^1$ in G is —CH$_3$ and R$^2$ in G is —CH$_3$.

In some embodiments, G is —CH$_2$OC(O) R$^1$R$^2$, and R$^1$ and R$^2$ in G are each independently selected from hydrogen and hydroxy.

In some embodiments, R$^1$ in G is hydrogen and R$^2$ in G is hydrogen or hydroxy.

In some embodiments, G is —CH$_2$C(O)NR$^1$R$^2$ and R$^1$ and R$^2$ in G are each independently selected from hydrogen and C$_1$-C$_4$alkyl.

In some embodiments, R$^1$ in G is —CH$_3$ and R$^2$ in G is H or —CH$_3$.

In some embodiments, G is —CH$_2$C(O)OR$^3$ and R$^3$ in G is hydrogen or C$_1$-C$_6$alkyl.

In some embodiments, R$^1$ in G is H.

In some embodiments, G is —S—CH$_3$.

In some embodiments, G is —CH$_2$—Y—Z; and Y is —S—.

In some embodiments, G is —CH$_2$—Y—Z; and Y is —S(O)$_2$—.

In some embodiments, G is —Y—Z; and Y is —CH$_2$—.

In some embodiments, Z is —CH$_3$.

In some embodiments, Z is

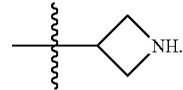

In some embodiments, Z is CH$_2$CN.

In some embodiments, Z is CH$_2$N$_3$.

In some embodiments, Z is —CH$_2$F.

In some embodiments, Z is —CHF$_2$.

In some embodiments, Z is —CF$_3$.

In some embodiments, Z is selected from the group consisting of thiophene, imidazole, N-methylimidazole, aminoimidazole, triazole, N-methyltriazole, aminotriazole, tetrazole, N-methyltetrazole, aminotetrazole, thiazole, aminothiazole, thiadiazole, aminothiadiazole, oxazole, oxadiazole, pyridine, pyridazine, pyrimidine, pyrazine, azitidine and piperdine.

In some embodiments, Z is N-methyltetrazole.

In some embodiments, Z is thiadiazole.

In some embodiments, Z is aminothiadiazole.

In some embodiments, Z is azitidine.

In some embodiments, Z is thiophene.

In some embodiments, Z is selected from the group consisting of

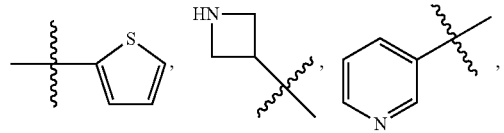

-continued
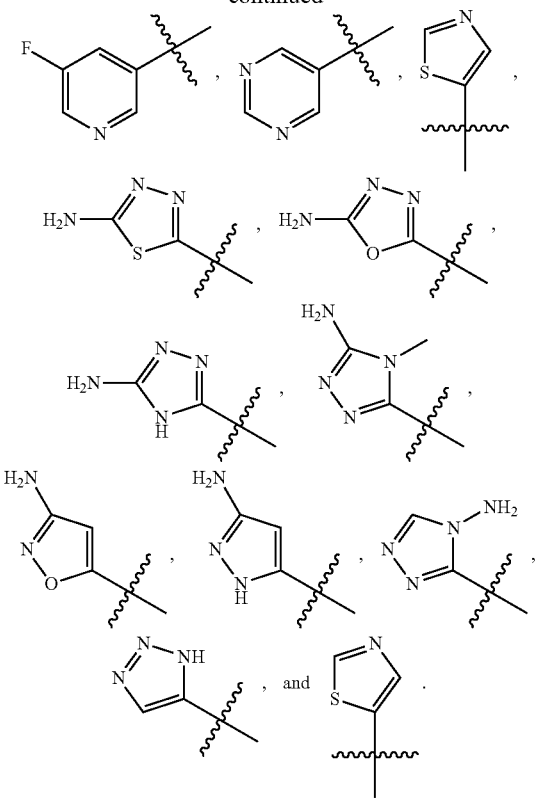
In some embodiments, Z is
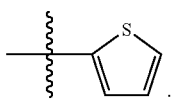 [SMILES: *c1cccs1]
Some specific embodiments of the compound described herein have the following structures:
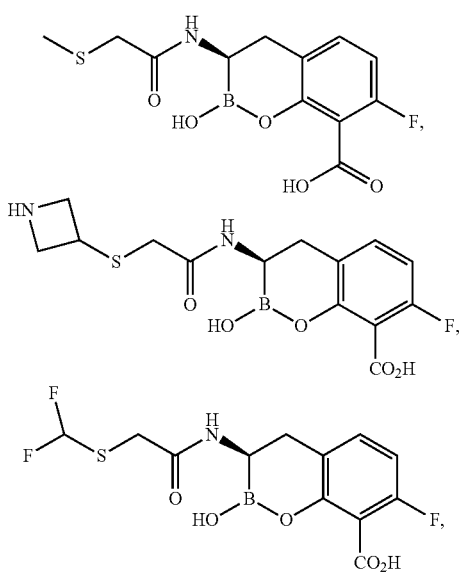
-continued
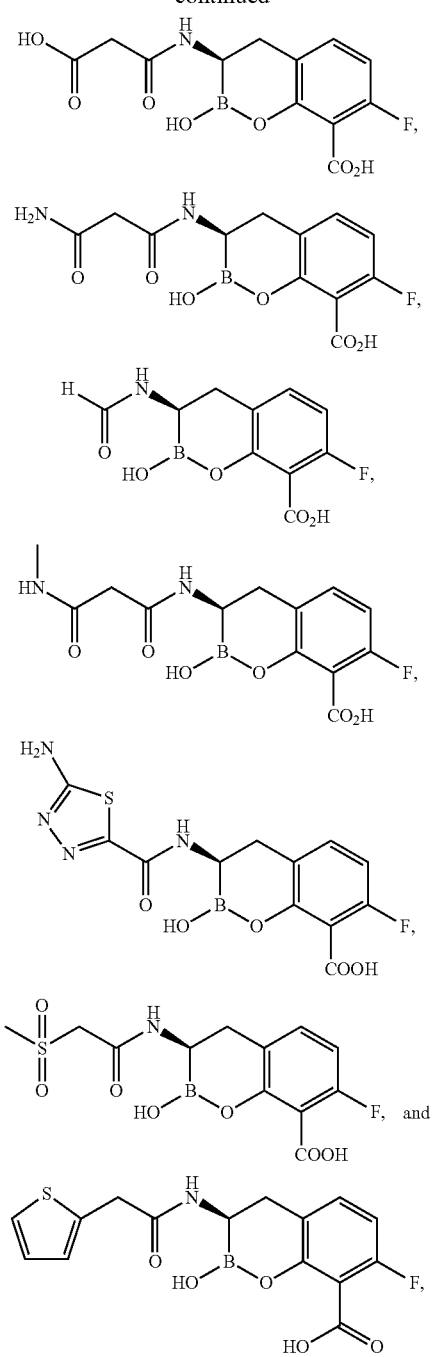
or pharmaceutically acceptable salts thereof.
Some specific embodiments of the compound described herein have the following structures:
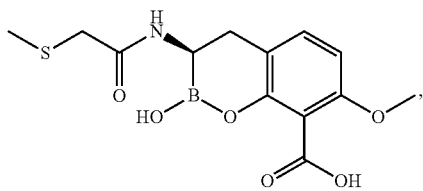

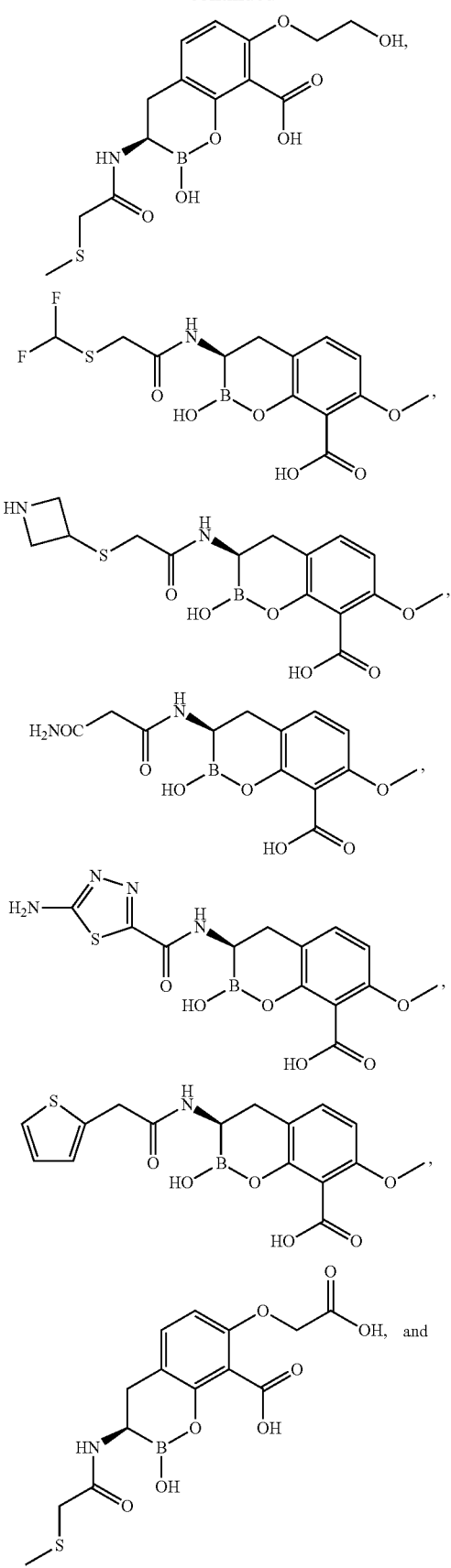
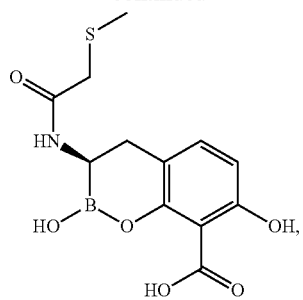
or pharmaceutically acceptable salts thereof.
Some specific embodiments of the compound described herein have the following structures:
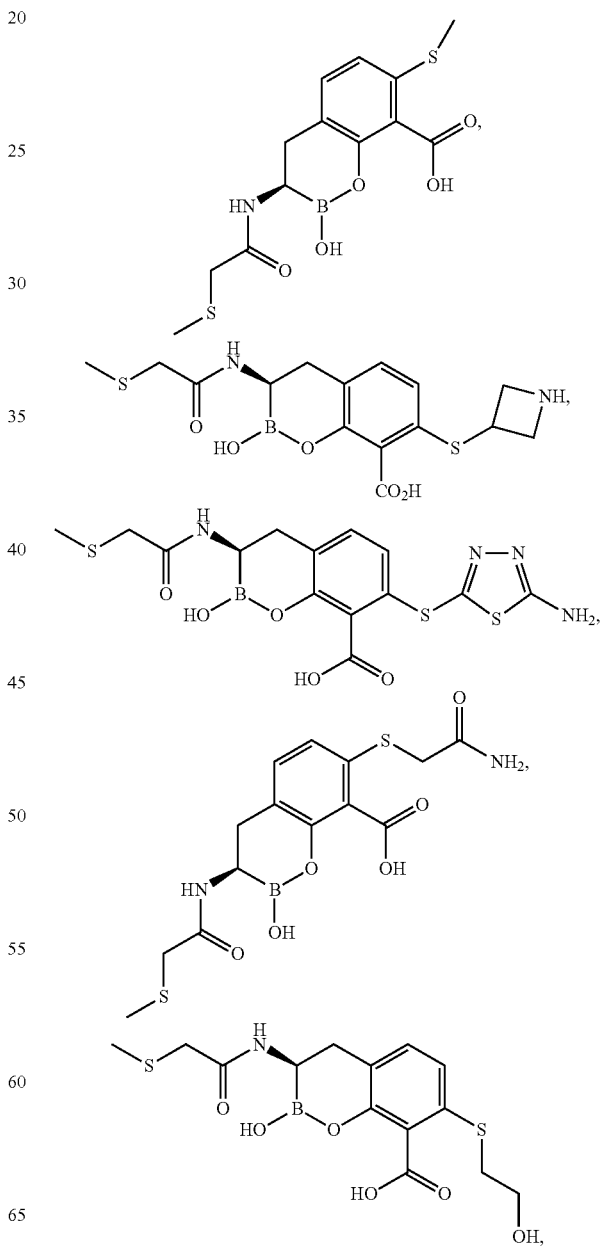

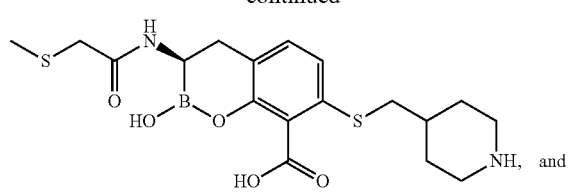
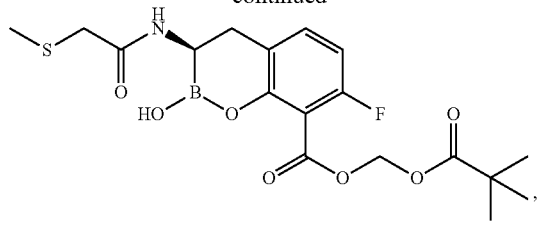
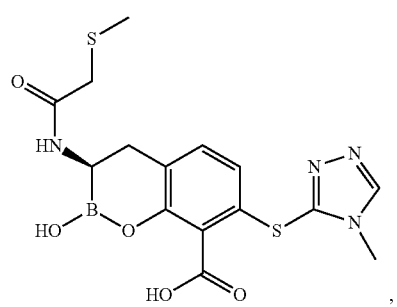
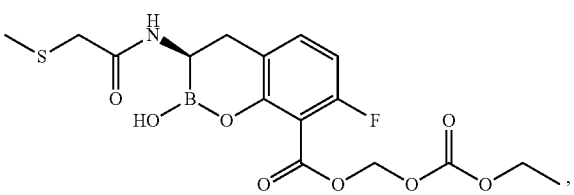
or pharmaceutically acceptable salts thereof.
Some specific embodiments of the compound described herein have the following structures:
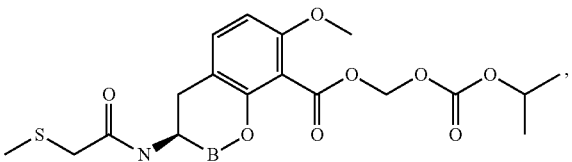
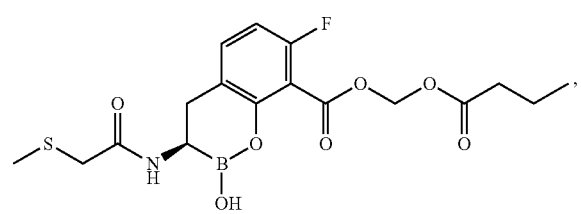
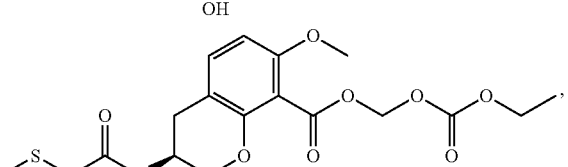
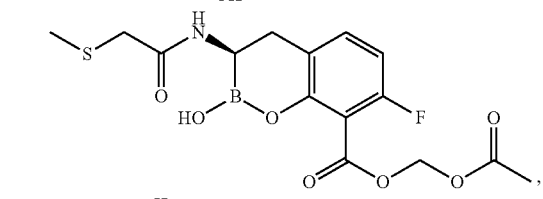
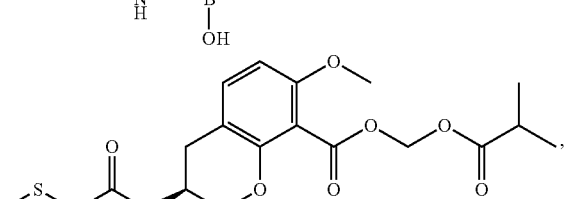
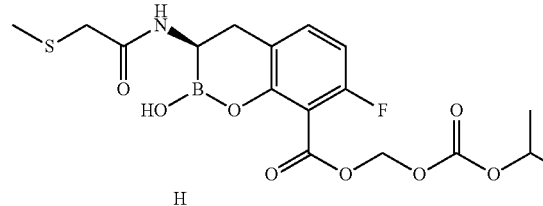
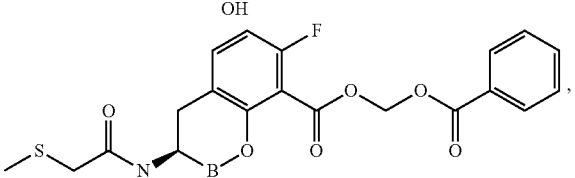
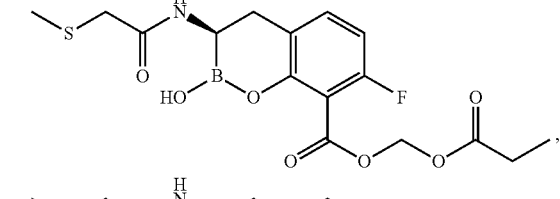
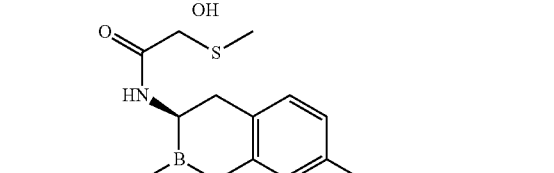
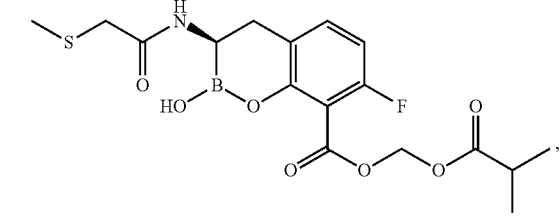
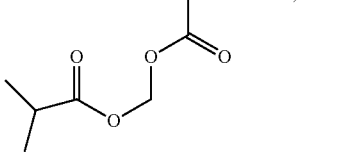

-continued

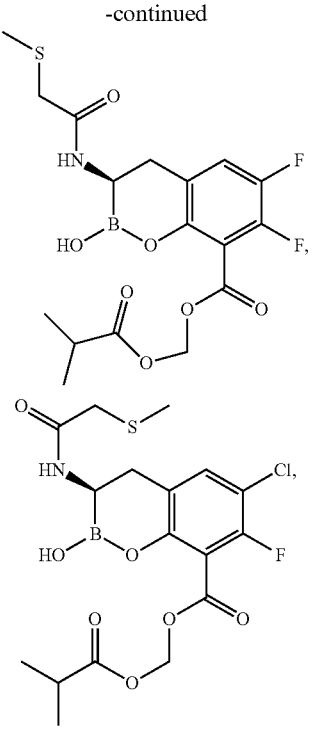

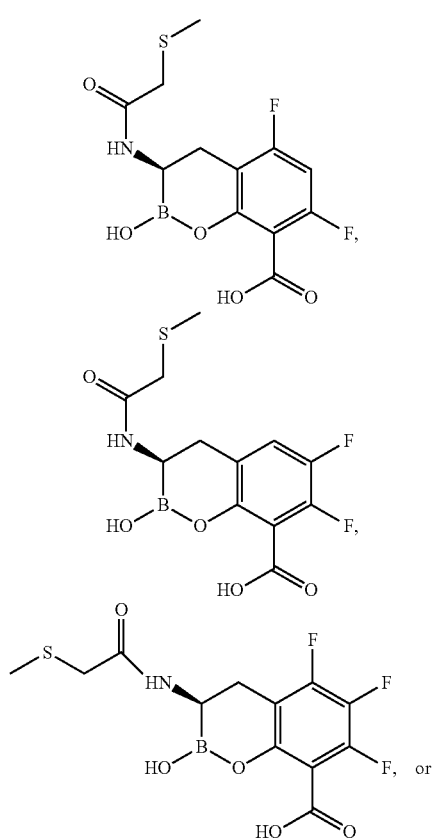

or pharmaceutically acceptable salts thereof.

Some specific embodiments of the compounds described herein have the following structures:

-continued

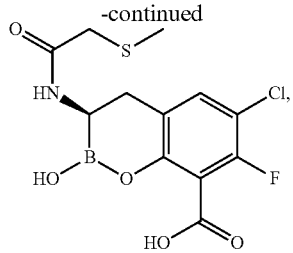

or pharmaceutically acceptable salts thereof.

Some specific embodiments of the compounds described herein have the following structure:

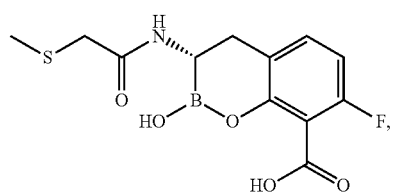 [SMILES: CSCC(=O)N[C@@H]1Cc2ccc(F)c(C(=O)O)c2OB1O]

or pharmaceutically acceptable salts thereof.

Some specific embodiments of the compounds described herein have the following structure:

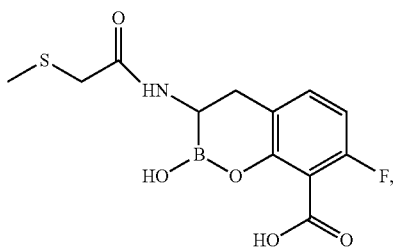 [SMILES: CSCC(=O)NC1Cc2ccc(F)c(C(=O)O)c2OB1O]

or pharmaceutically acceptable salts thereof.

In some embodiments, due to the facile exchange of boron esters, the compounds described herein may convert to or exist in equilibrium with alternate forms. Accordingly, in some embodiments, the compounds described herein may exist in combination with one or more of these forms. For example, as shown below, the compounds disclosed herein may exist in cyclic form as cyclic boronate monoesters as formula I or in acyclic form as boronic acids as formula II (*Biochemistry*, 2000, 39, 5312-21), or may exist as a mixture of the two forms depending on the medium.

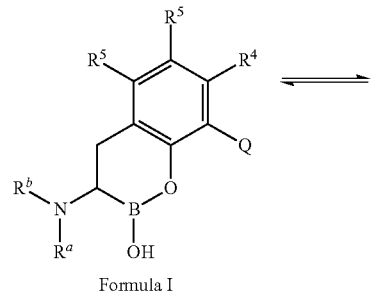

Formula I

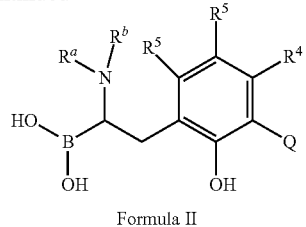

Formula II

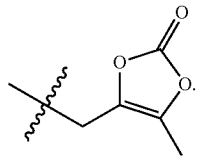 [SMILES: *Cc1oc(=O)oc1C]

Some boronic acid compounds have the undesirable tendency to form oligomers (e.g., dimers, trimers, tetramers, etc.). While not being bound by any particular theory, it is believed that the compounds of Formula (I) or (II) as described herein can prevent the formation of oligomers.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Definitions

The term "carboxylic acid prodrug moiety" as used herein refers to a moiety that converts to a carboxylic acid moiety in vivo, when administered to a patient. In some embodiments, the carboxylic acid prodrug moiety is an ester. Examples of carboxylic acid prodrug moieties can include but are not limited to COOR, wherein R is $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, 5-10 membered heterocyclyl; —$CR^6R^7OC(O)C_{1-9}$alkyl; —$CR^6R^7OC(O)OC_{1-9}$alkyl; —$CR^6R^7OC(O)C_{6-10}$aryl; —$CR^6R^7OC(O)OC_{6-10}$aryl; and "Solvate" refers to the compound formed by the interaction of a solvent and a compound described herein or salt thereof. Suitable solvates are pharmaceutically acceptable solvates including hydrates.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms.

The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[14.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)C(=O)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N(R$_A$)C(=S)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —CF$_3$), halo($C_1$-$C_6$)alkoxy (e.g., —OCF$_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

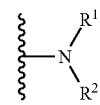

and R$^1$ and R$^2$ are defined as selected from the group consisting of hydrogen and alkyl, or R$^1$ and R$^2$ together with the nitrogen to which they are attached form a heteroaryl, it is meant that R¹ and R² can be selected from hydrogen or alkyl, or alternatively, the substructure has structure:

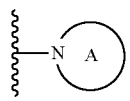

where ring A is a heteroaryl ring containing the depicted nitrogen.

Similarly, when two "adjacent" R groups are said to form a ring "together with the atoms to which they are attached," it is meant that the collective unit of the atoms, intervening bonds, and the two R groups are the recited ring. For example, when the following substructure is present:

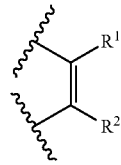

and R¹ and R² are defined as selected from the group consisting of hydrogen and alkyl, or R¹ and R² together with the atoms to which they are attached form an aryl or carbocyclyl, it is meant that R¹ and R² can be selected from hydrogen or alkyl, or alternatively, the substructure has structure:

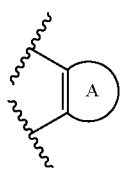

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

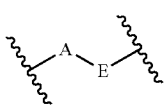

includes the substituent being oriented such that the A is attached at the leftmost attachment point of the molecule as well as the case in which A is attached at the rightmost attachment point of the molecule.

As used herein, "isosteres" of a chemical group are other chemical groups that exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated include —$SO_3H$, —$SO_2HNR$, —$PO_2(R)_2$, —$PO_3(R)_2$, —$CONHNHSO_2R$, —$COHNSO_2R$, and —$CONRCN$, where R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. In addition, carboxylic acid isosteres can include 5-7 membered carbocycles or heterocycles containing any combination of $CH_2$, O, S, or N in any chemically stable oxidation state, where any of the atoms of said ring structure are optionally substituted in one or more positions. The following structures are non-limiting examples of carbocyclic and heterocyclic isosteres contemplated. The atoms of said ring structure may be optionally substituted at one or more positions with R as defined above.

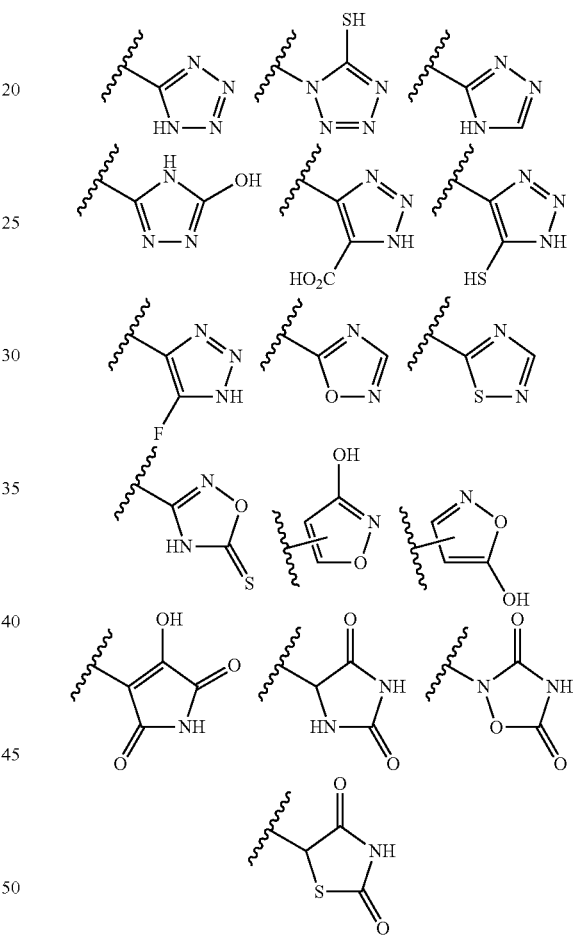

It is also contemplated that when chemical substituents are added to a carboxylic isostere, the compound retains the properties of a carboxylic isostere. It is contemplated that when a carboxylic isostere is optionally substituted with one or more moieties selected from R as defined above, then the substitution and substitution position is selected such that it does not eliminate the carboxylic acid isosteric properties of the compound. Similarly, it is also contemplated that the placement of one or more R substituents upon a carbocyclic or heterocyclic carboxylic acid isostere is not a substitution at one or more atom(s) that maintain(s) or is/are integral to the carboxylic acid isosteric properties of the compound, if such substituent(s) would destroy the carboxylic acid isosteric properties of the compound.

Other carboxylic acid isosteres not specifically exemplified in this specification are also contemplated.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

"Monosaccharide" as used herein refers to a chemical compound of general formula $C_x(H_2O)_x$, where x is 3 to 10. Examples of monosaccharide include but are not limited to glucose (dextrose), arabinose, mannitol, fructose (levulose) and galactose. "Monosaccharide derivative" as used herein refers to a monosaccharide wherein one or more —OH groups can be replaced by the substituents described above in the definition of "substituted." In some monosaccharide derivatives, one ore more —OH groups on the monosaccharide can be replaced by one or more —NH$_2$ or —NH—CH$_3$ groups. One example of a monosaccharide derivative includes meglumine. Other examples of a monosaccharide derivative can include an amino alcohol.

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protective groups, such as those described in *Protective Groups in Organic Chemistry* (ed. J. F. W. McOmic, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protective groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims. Unless otherwise indicated, substituent variables in the following schemes have the same definitions as elsewhere in this application.

Synthesis of Compounds of Formula I or II

The intermediate compound of Formula III-c can be prepared from the compounds of formula III-a as shown in Scheme 1a. In the starting compound III-a, $X^1$ can be an alkyl, alkoxy, or halogen; Z' can be a halogen, —OH, —SH, —O—C$_{1-6}$ alkyl, or —S—C$_{1-6}$ alkyl; R' can be any suitable protective group including but not limited to a tert-butyloxycarbonyl; and R" can be any suitable protective group including but not limited to t-butyl. R' and R" can be the same or different. The compound of formula III-b can be prepared via carboxylation of the compound of formula III-a or derivative thereof following the method described in PCT Publication No. WO2012/106995, which is incorporated herein by reference in its entirety. In the compound III-b, R' can be any suitable protective group including but not limited to t-butyl The compound of formula III-c can be synthesized from compounds of formula III-b where $X^2$ is substituted as bromomethylene, triflate, bromo or iodo groups. For example, some compounds of formula III-b wherein $X^2$ is Br, I, or —OTf can be transformed to the compound of formula III-c by utilizing Reformatsky reagent of bromomethylene boronate ester as described in *J. Org. Chem.*, 2013, 78, 8250-8266; *Chem Lett.*, 1993, 845-848, which is incorporated herein by reference in its entirety, or by the reaction of methylenediboronate ester as described in *Org. Lett.* 2011, 13, 3368-3371, which is incorporated herein by reference in its entirety. In addition, some compounds of Formula III-b wherein $X^2$ is —CHO and Z' is F can be utilized to introduce various $R^4$ groups such as —O—C$_{1-6}$ alkyl, or —S—C$_{1-6}$ alkyl by displacement of corresponding Z group (*Journal of Medicinal Chemistry*, 2008, 51, 1925-1944, which is incorporated herein by reference in its entirety). Such benzaldehyde derivative of Formula III-b can be converted to bromomethyl intermediates via one step as described in *Tetrahedron Lett.*, 1984, 25, 1103-1104, which is incorporated herein by reference in its entirety, or two step transformations including reduction and halide formation. The bromomethyl intermediate can be transformed to the compound of formula III-c via palladium catalyzed reaction utilizing diboronate ester of desired enantiomerically pure pinanediol ester (*Tetrahedron Lett.*, 2003, 44, 233-235, which is incorporated herein by reference in its entirety).

Scheme 1a

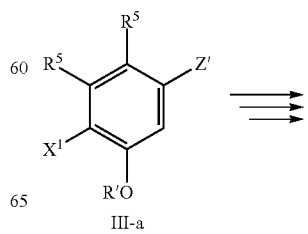

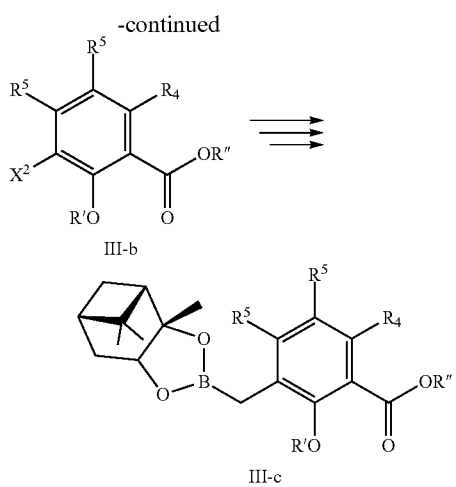

Some exemplary but non-limiting general synthetic schemes for preparing the intermediate compound of Formula III-c is shown in Scheme 1b below. The compound of Formula III-c can be made using two exemplary synthesis routes. The first route starts with a salicylic acid compound of formula S1-1, wherein X can be a halogen. The salicylic acid compound of formula S1-1 can react with allyl bromide to undergo alkylation and esterification to first form the ether compound of formula S1-2 and then to form a vinyl phenyl compound of S1-3. The ester group of compound of S1-3 can be converted back to a carboxylic acid group. Protective groups can then be added to the carboxylic acid and hydroxyl groups of compound S1-4 to form the compound of S1-5. R' in the compound of S1-5 can be any suitable protective groups, including but not limited to a tert-butyloxycarbonyl. The double bond in compound of S1-5 can migrate and subsequently undergo oxidation to form an aldehyde group of compound S1-7. The halogen group X in compound of S1-7 can be replaced with a $R^4$ group to form the compound of S1-8, which can undergo protection to form a compound of S1-9. The aldehyde group in the compound of S1-9 can undergo hydrogenation to become a hydroxyl group in the compound of S1-10, and the hydroxyl group can be subsequently converted into a halogen group X' in the compound of S1-11. The compound S1-11 can undergo boron addition to form the compound of formula III-c.

Another route for making the compound of formula III-c starts with a compound of formula S2-1, wherein the $X^2$ can be alkyl, alkoxy, and halogen. The compound of S2-1 can undergo reaction to have a suitable protective group added to the hydroxyl group and form the compound of S2-2. R" in the compound of S2-2 can be any suitable protection group including but not limited to a t-butyl group. The compound of S2-3 can be prepared through carboxylation of the compound of S2-2. The compound of S2-3 can then undergo boron addition to form the compound of Formula III-c.

Scheme 1b.

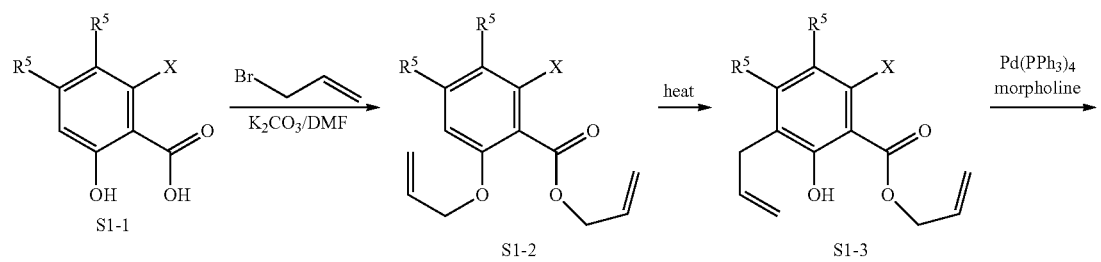

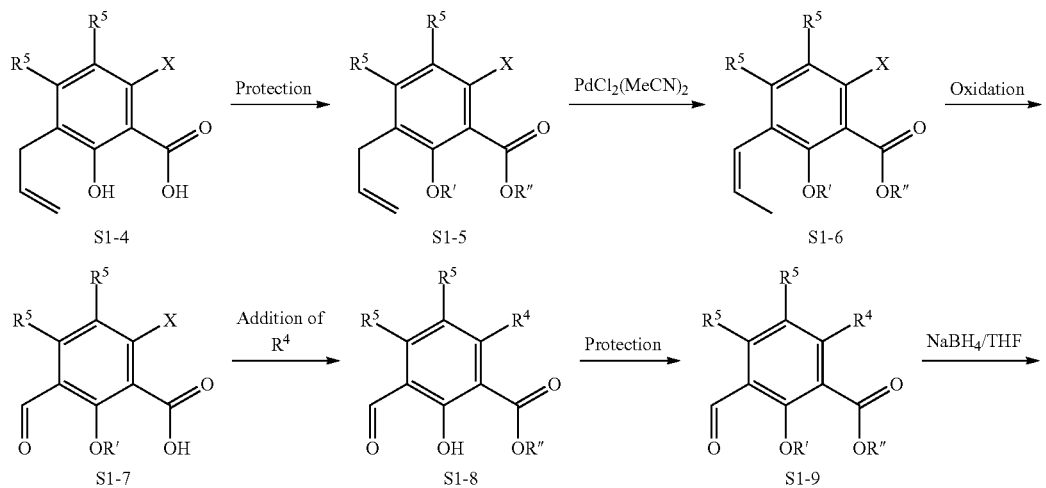

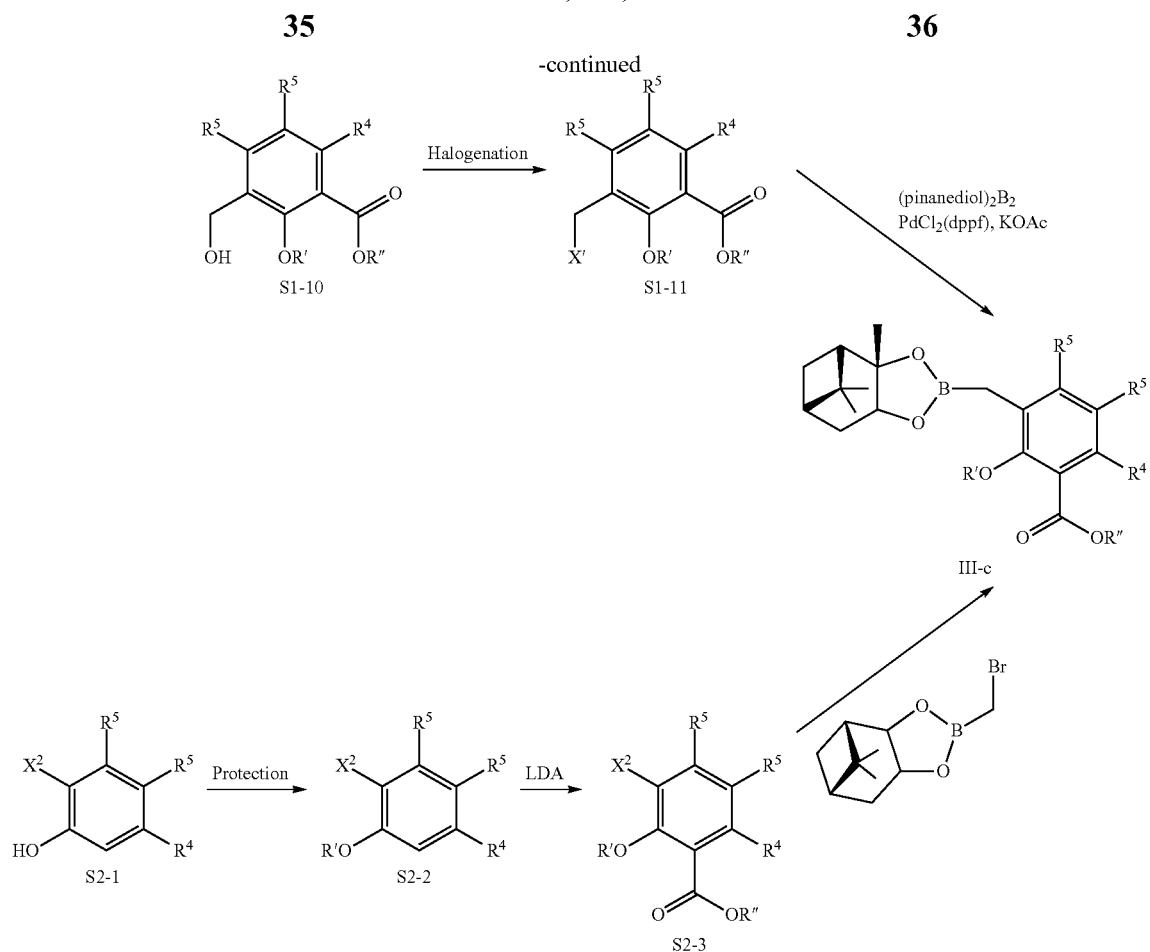

Scheme 1c shows an exemplary synthetic scheme for using an intermediate compound of Formula III-c to prepare the compound of formula Ia-1. The compound of formula III-c can undergo homologation to form the compound of formula III-d, which then can undergo amide formation to form the compound of formula III-e. Various G group can be introduced into the compound via a reaction between the carboxylic acid compounds G-COOH and compound III-e. The compound of formula III-f can then undergo deprotection to form the compound of formula (Ia-a).

Scheme 1c

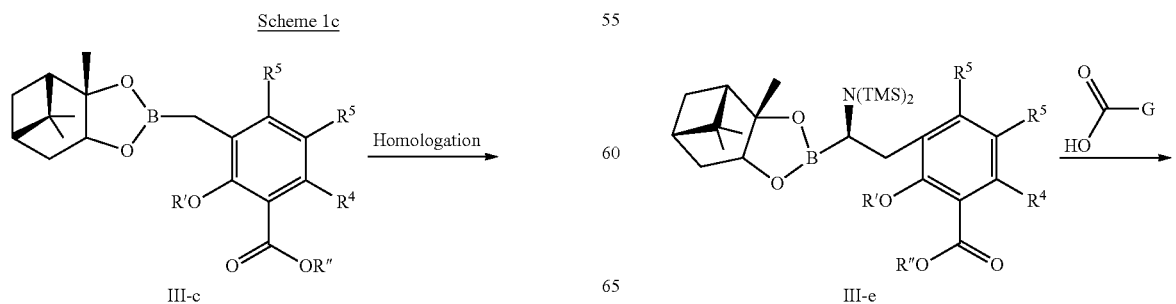

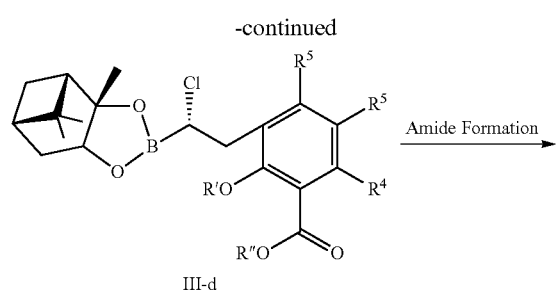

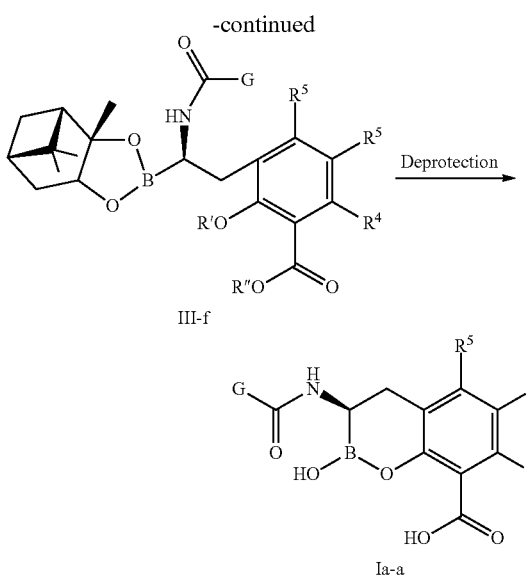

Scheme 1d is an exemplary but non-limiting general synthetic scheme for preparing the compound of S2-3 in scheme 1b. In the compound of S2-3, at least one of the $R^5$ is a halogen, alkoxy, or alkylthio. For example, one of the $R^5$ is a halogen, alkoxy, or alkylthio and the other $R^5$ is hydrogen; or each $R^5$ is independently a halogen, alkoxy, or alkylthio.

There are two routes in Scheme 1d for preparing the compound of S2-3. The first route starts with a phenol compound S2a-1 and adds a protective group to the hydroxyl group to form the compound of Formula S2a-2. The compound of S2a-3 can be prepared through carboxylation of the compound of Formula S2a-2. The compound of Formula 2a-3 can then undergo halogenation to form the compound of S2a-4, and the $X^2$ group in the compound of S2a-4 can be a halogen. The compound of S2a-4 can react with a suitable protecting agent to form the compound S2-3. The R' group in the compound of S2-3 can be any suitable protective group including but not limited to tert-butyl group; and the R" group in the compound of S2-3 can be any suitable protective group including but not limited to tert-butyloxycarbonyl.

The second route for making the compound of S2-3 as shown in Scheme 1d starts with a salicyclic acid compound of S2b-1. The compound of S2b-1 can undergo halogenation to form a compound of S2b-2 wherein the $X^2$ group can be a halogen. The compound of S2b-2 can then react with one or more suitable protecting agents to form the compound of S2-3.

Scheme 1d

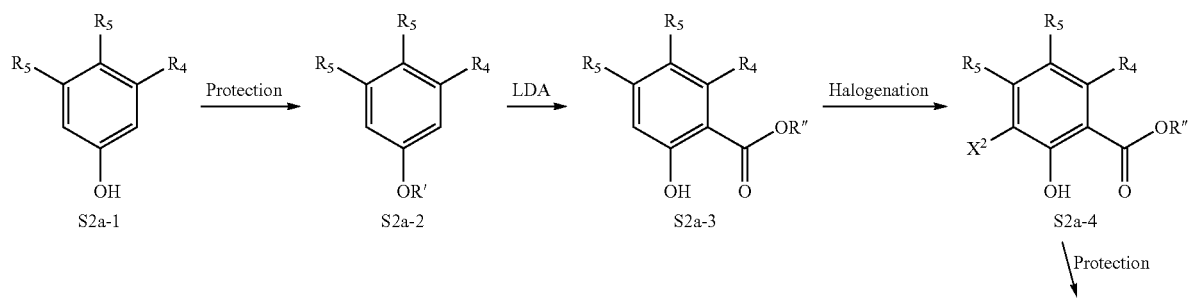

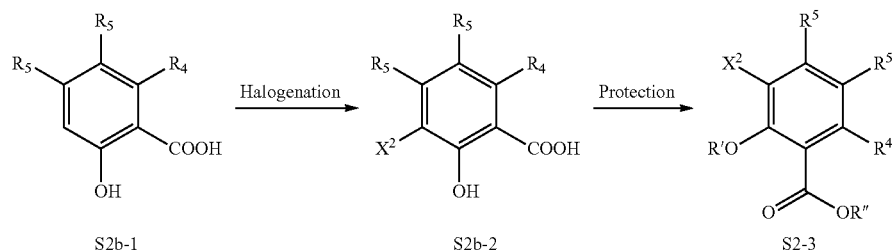

Scheme 1e below is another exemplary but non-limiting general synthetic scheme for preparing the compound of Formula Ia-1. The intermediate compound of Formula III-g can be made using two exemplary synthetic routes, and $X^4$ in Formula III-g can be alkoxy, aryloxy, alkylthio, or arylthio. The first route starts with a salicylic acid compound of formula S3-1, wherein $X^2$ can be a halogen; and R can be any suitable protective group for carboxylic acid. The salicyclic acid compound of formula S3-1 can react with a protecting agent such as p-Methoxybenzylchloride to form the compound of formula S3-2. The compound of formula S3-2 can undergo reaction to have another protective group added to the hydroxyl group that is para to the $X^2$ group. The compound of S3-3 can then undergo boron addition to form the compound of Formula III-g.

Another route for making the compound of formula III-g starts with a compound of formula S4-1, wherein the $X^2$ can be alkyl, alkoxy, or halogen; $X^3$ can be a halogen; R' can be any suitable protective group for the hydroxyl; and R" can be any suitable protective group for the carboxylic acid. The compound of S4-1 can react with an organosulfur compound such as 3-Methoxybenzenethiol to replace $X^3$ with a thio group and R''' can be any suitable protective group for the thiol including but not limited to the methoxybenzyl group. The compound of S4-2 can then undergo boron addition to form the compound of Formula III-g.

The compound of Formula III-g can then undergo homologation, amide formation and other steps shown in Scheme 1c to form the compound of formula III-h. The compound of formula III-h can then react with suitable agent to replace the $X^4$ with a $R^4$ group to form the compound of Formula Ia-a.

Synthesis of Prodrugs

Compounds of Formula I or II where the Q is a prodrug moiety may be synthesized by a variety of known methods of different carboxylic acid prodrugs (*Prodrugs: Challenges and Rewards*, V. J. Stella, et al., ed., Springer, New York, 2007, which is incorporated herein by reference in its entirety). These prodrugs include but are not limited to substituted or non-substituted alkyl esters, (acyloxy)alkyl esters (*Synthesis* 2012, 44, 207, which is incorporated herein by reference in its entirety), [(alkoxycarbonyl)oxy]methyl esters (PCT Publication No. WO10097675, which is incorporated herein by reference in its entirety), or (oxodioxolyl) methyl esters (*J. Med. Chem.* 1996, 39, 323-338, which is incorporated herein by reference in its entirety). Such prodrugs can be made from compounds of Formula I or II where Q is COOH by treatment with acid or in neutral conditions (e.g., carbodiimide coupling) in the presence of alcohols (ROH) or via base promoted esterification with RX where X is a leaving group in the presence of an appropriate base.

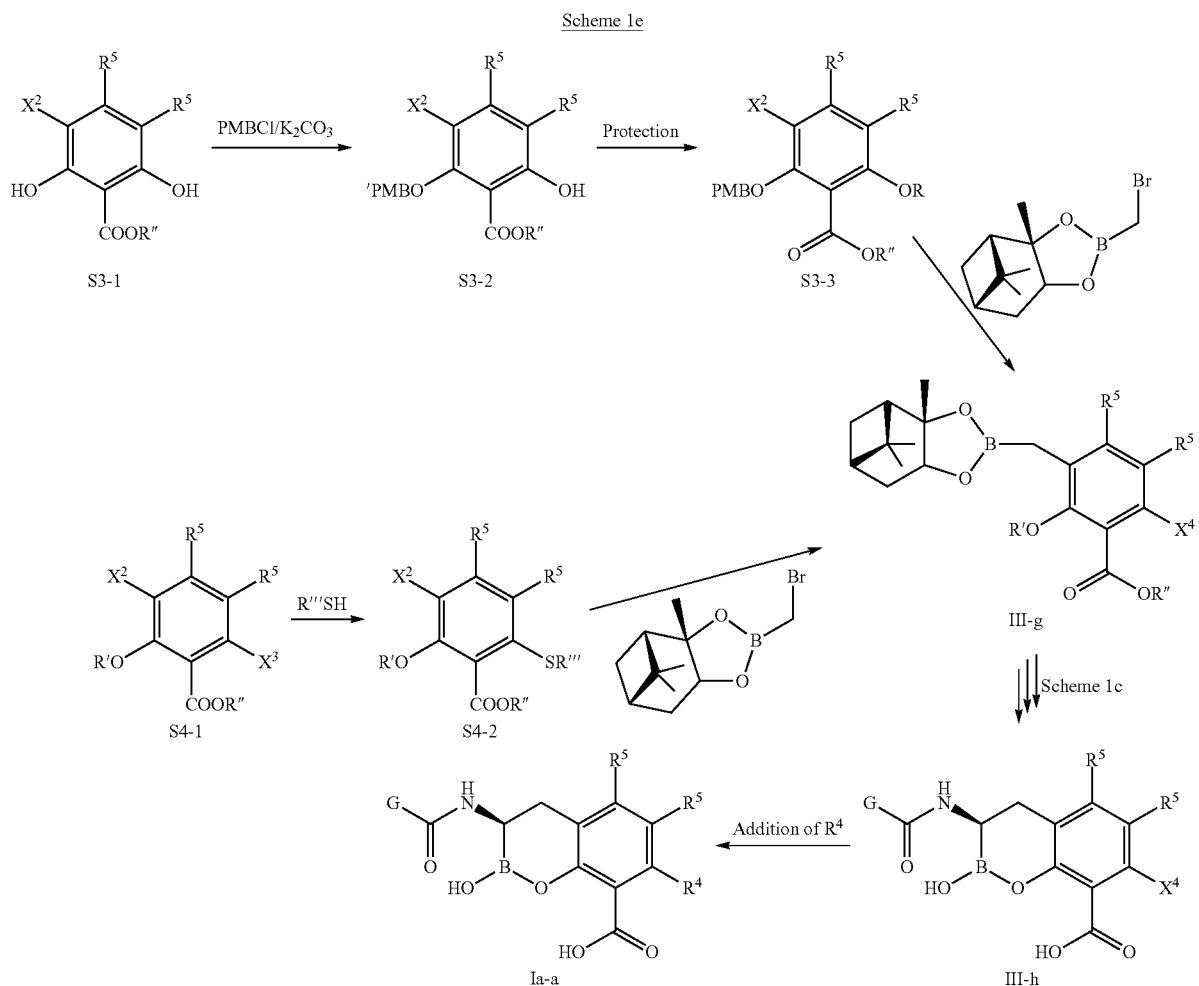

Scheme 1e

One exemplary but non-limiting general synthetic scheme for preparing the prodrug is shown in Scheme 2a below. The boronic acid of Formula Ia-a (Q is COOH) can react with a chloro/bromo-substituted prodrug moiety to form a prodrug of Formula Ia-b. Examples of the prodrug moiety R can be —C$_{1-9}$alkyl, —CR$^6$R$^7$OC(O)C$_{1-9}$alkyl, —CR$^6$R$^7$OC(O)OC$_{1-9}$alkyl, CR$^6$R$^7$OC(O)C$_{6-10}$aryl, CR$^6$R$^7$OC(O)OC$_{6-10}$aryl, and

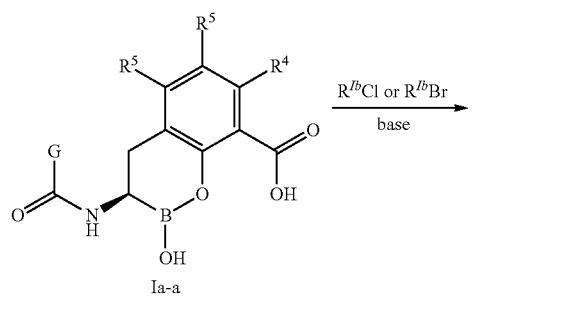

Scheme 2a

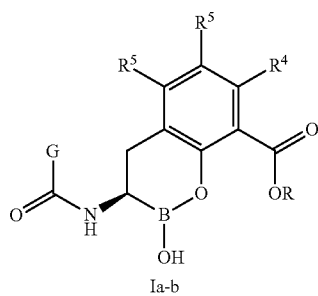

Ia-b

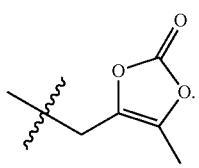 [SMILES: *Cc1oc(=O)oc1C]

Alternatively, compounds of Formula III-f may be also utilized for introduction of prodrugs (Scheme 2b). Such carboxylic acids III-f can be made from compounds of Formula III-e (scheme 1c) by selective deprotection of OR'. The prodrug group may also be introduced earlier in the sequence in compounds where —COOR" is —COOR. Such a sequence where the prodrug is introduced in earlier intermediates is only feasible when the ester is stable under the final deprotection conditions to remove the phenol protective group and the boronate ester.

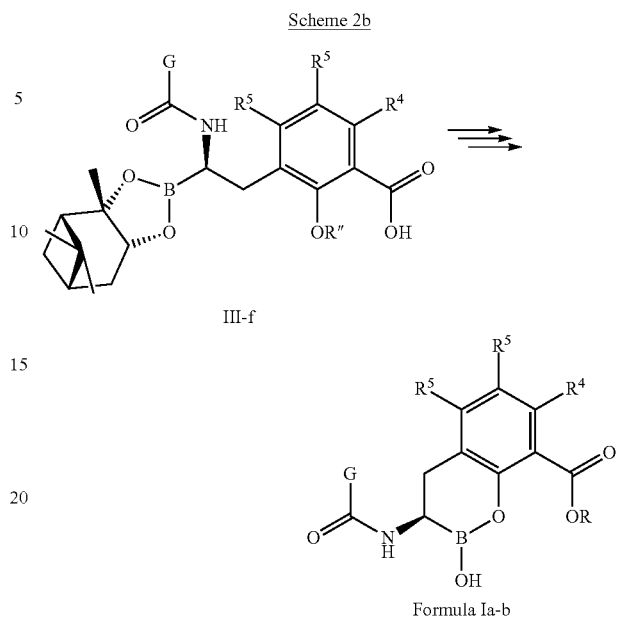

Scheme 2b

Formula Ia-b

Administration and Pharmaceutical Compositions

The compounds are administered at a therapeutically effective dosage. While human dosage levels have yet to be optimized for the compounds described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated herein by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

As noted above, it is believed that the compounds described herein, having a non-hydrogen substituents at the $R^4$ position, can reduce or prevent the formation of oligomers. To further reduce the likelihood of oligomer formation among the boronic acid derivatives described herein, some embodiments include pharmaceutical composition in which an excipient is included that prevents or limits the formation of oligomers. The excipient can be a monosaccharide or monosaccharide derivative. In one embodiment, the monosaccharide or monosaccharide derivative is meglumine. Other excipients include but are not limited to ethanolamine, diethanolamine, tris(hydroxymethyl)aminomethane (Tris), L-lysine, and Pyridine-2-methanol.

Some embodiments described herein relate to a chemical complex formed between the monosaccharide or monosaccharide derivative and the compound of Formula (I) or (II) described herein. In some embodiments, the interaction between the two components help increase the stability and/or solubility of the compound of Formula (I) or (II).

More generally, in some embodiments the monosaccharide or monosaccharide derivative can form a chemical complex with any compound containing a boronate moiety. In some embodiments, the compound containing a boronate moiety can be a boronic acid derivative described herein such as a compound of Formula (I) or (II) described herein. In other embodiments, the compound containing a boronate moiety can be any other boronate containing compounds, for example, known boronate-containing pharmaceutical agents. In some other embodiments, the monosaccharide or monosaccharide derivative used in forming the stable complex can be meglumine.

In some embodiments, of the inclusion of meglumine in a pharmaceutical composition prevents or reduces the formation of oligomers at a pH range desirable for pharmaceutical administration. In some embodiments, the pH of the composition can be in the range of about 5 to about 9, about 6 to 8, about 6 to about 7.5, about 7.1 to about 7.3, or about 7.1 to about 7.2. In some embodiments, the pH of the composition can be in the range of about 7.0-7.3. In some embodiments, the pH of the composition can be about 6.5, 6.6, 6.7, 6.8, 6.9, 7.0, 7.1, 7.2, 7.3, 7.4, 7.5, 7.6, 7.7, and 7.8. In some embodiments, the pH of the composition can be about 7.1. In some embodiments, the pH of the composition can be about 7.2.

The amount of the boronic acid derivatives that are present in a monomer form can vary depending on the pH of the solution, the oligomer-preventing excipient included, and the amount of the excipient in the composition. In some embodiments, the percentage of the monomer form can be more than 85%, more than 88%, more than 90%, more than 92%, more than 95%, more than 97% by weight, based on the total amount of the boronic acid derivative in the composition. In some embodiments, the percentage of the monomer form can be more than 96% by weight based on the total amount of the boronic acid derivative in the composition. In some embodiments, the percentage of the monomer form can be more than 97% by weight based on the total amount of the boronic acid derivative in the composition.

Methods of Treatment

Some embodiments of the present invention include methods of treating bacterial infections with the compounds and compositions comprising the compounds described herein. Some methods include administering a compound, composition, pharmaceutical composition described herein to a subject in need thereof. In some embodiments, a subject can be an animal, e.g., a mammal (including a human). In some embodiments, the bacterial infection comprises a bacteria described herein. As will be appreciated from the foregoing, methods of treating a bacterial infection include methods for preventing bacterial infection in a subject at risk thereof.

In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered i.v.

Examples of additional medicaments include an antibacterial agent, antifungal agent, an antiviral agent, an anti-inflammatory agent and an anti-allergic agent.

Preferred embodiments include combinations of a compound, composition or pharmaceutical composition described herein with an antibacterial agent such as a β-lactam. Examples of such β-lactams include Amoxicillin, Ampicillin (e.g., Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (e.g., Dicloxacillin, Flucloxacillin), Oxacillin, Methicillin, Nafcillin, Faropenem, Biapenem, Doripenem, Ertapenem, Imipenem, Meropenem, Tebipenem, Ceftibuten, Panipenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftiofur, Cefquinome, Cefovecin, Aztreonam, Tigemonam and Carumonam, CXA-101, RWJ-54428, MC-04,546, ME1036, RWJ-442831, RWJ-333441, or RWJ-333442.

Preferred embodiments include β-lactams such as Ceftazidime, Biapenem, Doripenem, Ertapenem, Imipenem, Meropenem Tebipenem, Ceftibuten, and Panipenem.

Additional preferred embodiments include β-lactams such as Aztreonam, Tigemonam, BAL30072, SYN 2416 and Carumonam.

Additional Examples of such β-lactams include penicillin, cephalosporin, carbapenem, monobactam, bridged monobactam, or combination thereof, wherein the penicillin is benzathine penicillin, benzylpenicillin, phenoxymethylpenicillin, procaine, penicillin, oxacillin, methicillin, dicloxacillin, flucloxacillin, temocillin, amoxicillin, ampicillin, co-amoxiclav, azlocillin, carbenicillin, ticarcillin, mezlocillin, piperacillin, apalcillin, hetacillin, bacampicillin, sulbenicillin, mecicilam, pevmecillinam, ciclacillin, talapicillin, aspoxicillin, cloxacillin, nafcillin, pivampicillin, or a combination thereof.

In some embodiments, the cephalosporin can be cephalothin, cephaloridin, cefaclor, cefadroxil, cefamandole, cefazolin, cephalexin, cephradine, ceftizoxime, cefoxitin, cephacetril, cefotiam, cefotaxime, cefsulodin, cefoperazone, ceftizoxime, cefinenoxime, cefinetazole, cephaloglycin, cefonicid, cefodizime, cefpirome, ceftazidime, ceftriaxone, cefpiramide, cefbuperazone, cefozopran, cefpim, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbacef, latamoxef, or a combination thereof.

In some embodiments, the cephalosporin can be an anti-MRSA cephalosporin.

In some embodiments, the anti-MRSA cephalosporin is cefiobiprole, cefiaroline, or a combination thereof.

In some embodiments, the carbapenem is imipenem, meropenem, ertapenem, faropenem, doripenem, biapenem, panipenem, tebipenem, ceftibuten, or a combination thereof.

In some embodiments, the carbapenem is an anti-MRSA carbapenem.

In some embodiments, the anti-MRSA carbapenem is PZ601 or ME1036.

Some embodiments include a combination of the compounds, compositions and/or pharmaceutical compositions described herein with an additional agent, wherein the additional agent comprises a monobactam. Examples of monobactams include aztreonam, tigemonam, nocardicin A, carumonam, and tabtoxin. In some such embodiments, the compound, composition and/or pharmaceutical composition comprises a class A, C, or D beta-lactamase inhibitor. Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises a class B beta lactamase inhibitor. An example of a class B beta lactamase inhibitor includes ME1071 (Yoshikazu Ishii et al, "In Vitro Potentiation of Carbapenems with ME1071, a Novel Metallo-β-Lactamase Inhibitor, against Metallo-β-lactamase Producing *Pseudomonas aeruginosa* Clinical Isolates." Antimicrob. Agents Chemother. doi:10.1128/AAC.01397-09 (July 2010)). Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises one or more agents that include a class A, B, C, or D beta lactamase inhibitor. Some embodiments include co-administering the compound, composition or pharmaceutical composition described herein with the one or more additional agents.

Indications

The compounds and compositions comprising the compounds described herein can be used to treat bacterial infections. Bacterial infections that can be treated with the compounds, compositions and methods described herein can comprise a wide spectrum of bacteria. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

The following examples will further describe the present invention, and are used for the purposes of illustration only, and should not be considered as limiting.

EXAMPLES

Example 1: (R)-7-fluoro-2-hydroxy-3-(2-(methylthio)acetamido)-3,4-dihydro-2H-benzo[e][1,2]oxaborinine-8-carboxylic acid (1)

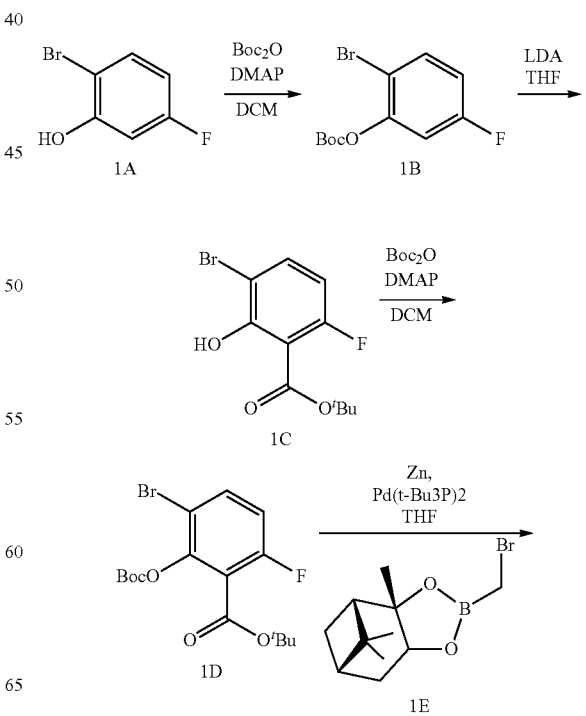

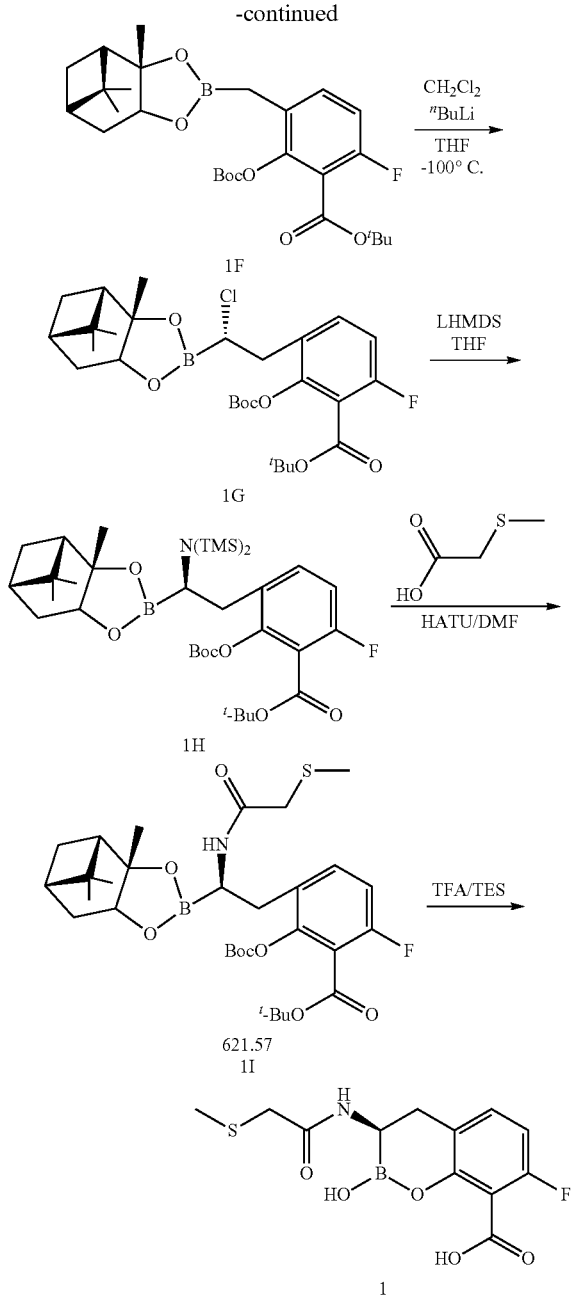

was evaporated to dryness to afford compound 1C (17.9 g, 83%) which was used directly to the next step without further purification.

$^1$H NMR (400 MHz, CDCl$_3$) δ 12.23 (s, 1H), 7.59 (m, 1H), 6.53 (m, 1H), 1.61 (s, 9H).

Step 3: Synthesis of 1D

To a solution of compound 1C (17.99 g, 62 mmol) and Boc$_2$O (20.2 g, 92.7 mmol) in DCM (200 mL) at r.t. was added DMAP (400 mg, 3.1 mmol), the mixture was stirred at r.t. overnight, evaporated to dryness, purified by silica gel chromatography to afford compound 1D (19.1 g, 79%).

$^1$H NMR (400 MHz, CDCl$_3$) δ 7.59 (m, 1H), 6.93 (m, 1H), 1.56 (s, 9H), 9, 1.52 (s, 9H).

Step 4: Synthesis of 1F

To a mixture of Zn powder (10.8 g, 166 mmol) and compound 1E (WO2013/56163) (362 mg, 1.3 mmol) in anhydrous THF (60 mL) was added DIBAL-H (2 mL, 3 mmol, 1.5 M in toluene) at r.t., the mixture was stirred at room temperature for 5 min, then more compound 1E (17.7 g, 65 mmol) in anhydrous THF (60 mL) was added dropwise into the mixture over 20 min, the reaction mixture was warmed up to 50° C. and stirred at this temperature for 1 h, then the clear solution on the up-layer was transferred into a mixture of compound 1D (17.3 g, 44 mmol) and Pd(t-Bu$_3$P)$_2$ (558 mg, 1.1 mmol) in THF (60 mL), the mixture was stirred at r.t. under N$_2$ for 1 h, concentrated, and purified by silica gel chromatography directly to afford the titled compound 1F (18.5 g, 83%).

$^1$H NMR (400 MHz, CDCl3) δ 7.27-7.39 (m, 1H), 6.88-6.92 (m, 1H), 4.25-4.27 (m, 1H), 2.26-2.32 (m, 1H), 2.20 (m, 3H), 2.00-2.03 (m, 1H), 1.81-1.88 (m, 2H), 1.56 (s, 9H), 1.54 (s, 9H), 1.38 (s, 3H), 1.27 (s, 3H), 1.16-1.19 (d, 1H), 0.82 (s, 3H).

Step 5: Synthesis of 1G

To a solution of DCM (4.73 mL, 73.4 mmol) in anhydrous THF (400 mL) at −100° C. was added drop-wise n-BuLi (2.5 M in hexane, 21 mL, 51.2 mmol) over 1 h, the mixture was stirred at this temperature for 30 min, then a solution of compound 1F (18.5 g, 36.7 mmol) in anhydrous THF (100 mL) was added drop-wise into this mixture at −100° C. over 30 min, the mixture was slowly warmed up to r.t. and stirred at r.t. overnight, evaporated to dryness, and purified by silica gel chromatography to afford the titled compound 1G (16.3 g, 80%).

$^1$H NMR (400 MHz, CDCl$_3$) δ 7.35-7.39 (m, 1H), 6.92-6.96 (m, 1H), 4.35-4.37 (m, 1H), 3.61-3.65 (m, 1H), 3.13-3.19 (m, 1H), 2.94-3.00 (m, 1H), 2.33-2.36 (m, 1H), 2.30-2.31 (m, 1H), 2.18-2.20 (m, 1H), 1.89-1.93 (m, 2H), 1.56 (s, 9H), 1.54 (s, 9H), 1.38 (s, 3H), 1.28 (s, 3H), 1.08 (d, 1H), 0.82 (s, 3H).

Step 6: Synthesis of 1H

To a solution of compound 1G (0.5 g, 0.9 mmol) in anhydrous THF (5 mL) at −78° C. was added drop-wise LHMDS (1.0 M in hexane, 1.26 mL, 1.26 mmol) over 30 min, the mixture was stirred at this temperature for 1 h, and then warmed up slowly to r.t. and stirred at r.t. overnight to afford compound 1H in THF solution which was used directly without any workup (0.9 mmol, 100%).

Step 7: Synthesis of 1I

To a solution of 2-(methylthio)acetic acid (0.51 g, 4.8 mmol) in anhydrous DMF (5 mL) was added HATU (1.8 g, 4.8 mmol), the mixture was stirred at r.t. for 10 min, then compound 1H in THF solution (20 mL, 4 mmol) was added and the mixture was stirred at r.t. overnight, extracted with EtOAc, washed with water and brine, dried over Na$_2$SO$_4$, Step 1: Synthesis of 1B To a solution of 2-bromo-5-fluorophenol (1A) (13.5 g, 71 mmol) and Boc2O (18.5 g, 85 mmol) in DCM (300 mL) at r.t. was added DMAP (439 mg, 3.6 mmol), the mixture was stirred at r.t. for 0.5 h, concentrated to dryness, and purified by silica gel chromatography to afford compound 1B (20.1 g, 97%).

$^1$H NMR (400 MHz, CDCl$_3$) δ 7.54 (m, 1H), 6.98 (m, 1H), 6.89 (m, 1H), 1.56 (s, 9H).

Step 2: Synthesis of 1C

To a solution of compound 1B (21.7 g, 74.6 mmol) in THF (150 mL) at −78° C. was added freshly prepared LDA solution (140 mL, 82.1 mmol), the mixture was stirred at −78° C. for 1 h, then warmed up slowly to r.t., quenched with 1 N HCl (aq., 200 mL), extracted with EtOAc, washed with water and brine, dried over Na$_2$SO$_4$, filtered and the filtrate filtered and evaporated to dryness, purified by silica gel chromatography to afford compound 1I (1.0 g, 40%). Confirmed by H NMR as below:

$^1$H NMR (400 MHz, CDCl$_3$) δ 7.27 (m, 1H), 6.96-6.98 (m, 1H), 4.28-4.30 (m, 1H), 3.19 (s, 2H), 3.07-3.10 (m, 1H), 2.93-2.95 (m, 2H), 2.22 (m, 2H), 2.10 (m, 1H), 1.97-2.04 (m, 3H), 1.81-1.88 (m, 3H), 1.56 (s, 9H), 1.54 (s, 9H), 1.39 (s, 3H), 1.30 (m, 1H), 1.27 (s, 3H), 0.85 (s, 3H).

ESI-MS: [M+Na]$^+$: 644.

Step 8: Synthesis of 1

The solution of compound 11 (410 mg, 0.66 mmol) in THF (90%)/TES (3 mL/0.5 mL) was stirred at room temperature overnight and evaporated to dryness. The resulting oil was suspended in ether and some white solid precipitated out. The precipitation was filtered to afford a mixture of compound 1 and its dimer (110 mg). The filtrate was kept at r.t. for 2 days and filtered again to afford pure compound 1 (40 mg) after HPLC purification.

$^1$H NMR (400 MHz, CDCl$_3$) δ 7.11 (m, 1H), 6.60 (m, 1H), 3.24 (s, 2H), 3.17 (s, 1H), 2.86 (m, 2H), 1.83 (s, 3H).
ESI-MS: 314 [M+H]$^+$.

Example 2: (R)-3-(2-(azetidin-3-ylthio)acetamido)-7-fluoro-2-hydroxy-3,4-dihydro-2H-benzo[e][1,2]oxaborinine-8-carboxylic acid (2)

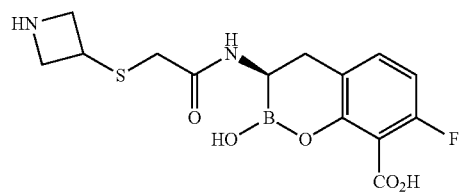

Compound 2 was prepared following the procedure described in Example 1 except replacing the 2-(methylthio)acetic acid in step 7 with 2-(azetidin-3-ylthio)acetic acid.

$^1$H NMR (400 MHz, CD$_3$OD) δ 7.10 (dd, 1H), 6.62 (dd, 1H), 4.28-4.38 (m, 2H), 3.72-3.88 (m, 3H), 3.44 (dd, 2H), 3.15 (s, 1H), 2.86 (s, 2H).
MS calcd for (C$_{14}$H$_{16}$BFN$_2$O$_5$S): 354.
MS (ESI, positive) found: (M+1): 355.
MS (ESI, negative) found: (M−1): 353.

Example 3: (R)-3-(2-(difluoromethylthio)acetamido)-7-fluoro-2-hydroxy-3,4-dihydro-2H-benzo[e][1,2]oxaborinine-8-carboxylic acid (3)

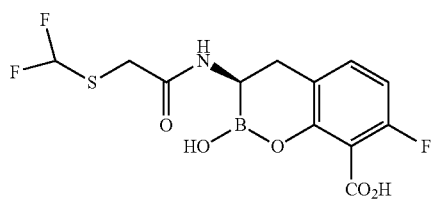

Compound 3 was prepared following the procedure described in Example 1 except replacing the 2-(methylthio) acetic acid in step 7 with 2-((difluoromethyl)thio)acetic acid.

$^1$H NMR (400 MHz, CD$_3$OD) δ 7.09 (dd, 1H), 6.93 (t, 1H, J=56 Hz), 6.59 (dd, 1H), 3.58-3.68 (m, 2H), 3.18 (S, 1H), 2.86 (s, 2H).
MS calcd for (C$_{12}$H$_{11}$BF$_3$NO$_5$S): 349.
MS (ESI, positive) found: (M+1): 350.
MS (ESI, negative) found: (M−1): 348.

Example 4: (R)-3-(2-carboxyacetamido)-7-fluoro-2-hydroxy-3,4-dihydro-2H-benzo[e][1,2]oxaborinine-8-carboxylic acid (4)

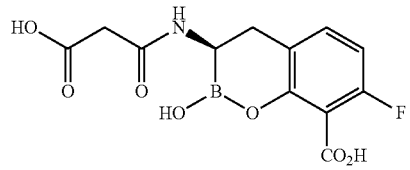

Compound 4 was prepared following the procedure described in Example 1 except replacing the 2-(methylthio) acetic acid in step 7 with 3-(tert-butoxy)-3-oxo-propanoic acid.

$^1$H NMR (400 MHz, CD$_3$OD) δ 7.11 (dd, 1H), 6.60 (dd, 1H), 3.30 (s, 2H), 3.19 (s, 1H), 2.86 (s, 2H).
MS calcd for (C$_{12}$H$_{11}$BFNO$_7$): 311.
MS (ESI, positive) found: (M+1): 312.

Example 5: (R)-3-(3-amino-3-oxopropanamido)-7-fluoro-2-hydroxy-3,4-dihydro-2H-benzo[e][1,2]oxaborinine-8-carboxylic acid (5)

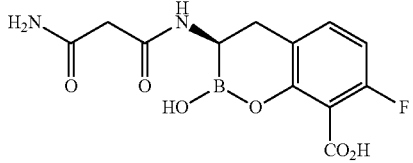

Compound 5 was prepared following the procedure described in Example 1 except replacing the 2-(methylthio) acetic acid in step 7 with 3-amino-3-oxopropanoic acid.

$^1$H NMR (400 MHz, CD$_3$OD) δ 7.09 (dd, 1H), 6.59 (dd, 1H), 3.32 (s, 2H), 3.18 (s, 1H), 2.88 (s, 2H).
MS calcd for (C$_{12}$H$_{12}$BFN$_2$O$_6$): 310.
MS (ESI, positive) found: (M+1): 311.
MS (ESI, negative) found: (M−1): 309.

Example 6: (R)-7-fluoro-3-formamido-2-hydroxy-3,4-dihydro-2H-benzo[e][1,2]oxaborinine-8-carboxylic acid (6)

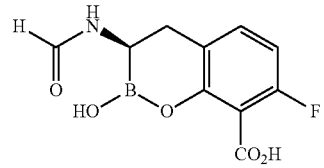

Compound 6 was prepared following the procedure described in Example 1 except replacing the 2-(methylthio) acetic acid in step 7 with formic acid.

$^1$H NMR (400 MHz, CD$_3$OD) δ 8.05 (s, 1H), 7.10 (dd, 1H), 6.59 (dd, 1H), 3.08 (s, 1H), 2.89 (s, 2H).

MS calcd for (C$_{10}$H$_9$BFNO$_5$): 253.

MS (ESI, positive) found: (M+1): 254.

MS (ESI, negative) found: (M−1): 252.

Example 7: (R)-7-fluoro-2-hydroxy-3-(3-(methylamino)-3-oxopropanamido)-3,4-dihydro-2H-benzo[e][1,2]oxaborinine-8-carboxylic acid (7)

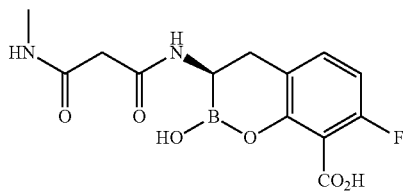

Compound 7 was prepared following the procedure described in Example 1 except replacing the 2-(methylthio) acetic acid in step 7 with 3-(methylamino)-3-oxopropanoic acid.

$^1$H NMR (400 MHz, CD$_3$OD) δ 7.09 (dd, 1H), 6.59 (dd, 1H), 3.30 (s, 2H), 3.17 (s, 1H), 2.85 (s, 2H), 2.65 (s, 3H).

MS calcd for (C$_{13}$H$_{14}$BFN$_2$O$_6$): 324.

MS (ESI, positive) found: (M+1): 325.

MS (ESI, negative) found: (M−1): 323.

Example 8: (R)-3-(5-amino-1,3,4-thiadiazole-2-carboxamido)-7-fluoro-2-hydroxy-3,4-dihydro-2H-benzo[e][1,2]oxaborinine-8-carboxylic acid (8)

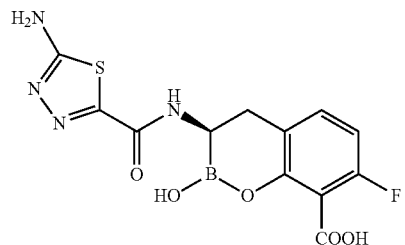

Compound 8 was prepared following the procedure described in Example 1 except replacing the 2-(methylthio) acetic acid in step 7 with 5-amino-1,3,4-thiadiazole-2-carboxylic acid.

$^1$H NMR (400 MHz, CD$_3$OD) δ 7.10 (m, 1H), 6.53 (m, 1H), 2.76-3.16 (m, 3H).

MS calcd for (C$_{12}$H$_{10}$BFN$_4$O$_5$S): 352.

MS (ESI, positive) found: (M+1): 353.

MS (ESI, negative) found: (M−1): 351.

Example 9: (R)-7-fluoro-2-hydroxy-3-(2-(methylsulfonyl)acetamido)-3,4-dihydro-2H-benzo[e][1,2]oxaborinine-8-carboxylic acid (9)

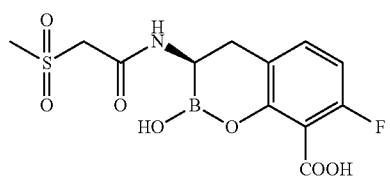

Compound 9 was prepared following the procedure described in Example 1 except replacing the 2-(methylthio) acetic acid in step 7 with 2-(methylsulfonyl)acetic acid.

$^1$H NMR (400 MHz, CD$_3$OD) δ 7.07 (dd, 1H), 6.60 (dd, 1H), 4.32 (d, 1H), 4.13 (d, 1H), 3.21 (s, 1H), 2.91 (s, 3H), 2.86 (s, 2H).

MS calcd for (C$_{12}$H$_{13}$BFNO$_7$S): 345.

MS (ESI, positive) found: (M+1): 346.

MS (ESI, negative) found: (M−1): 344.

Example 10: (R)-2-hydroxy-7-(methylthio)-3-(2-(methylthio)acetamido)-3,4-dihydro-2H-benzo[e][1,2]oxaborinine-8-carboxylic acid (10)

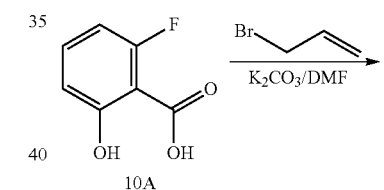

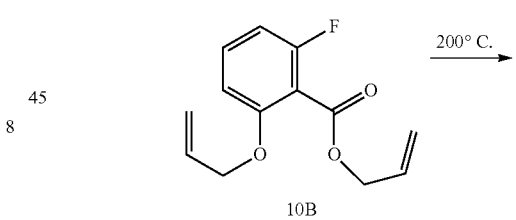

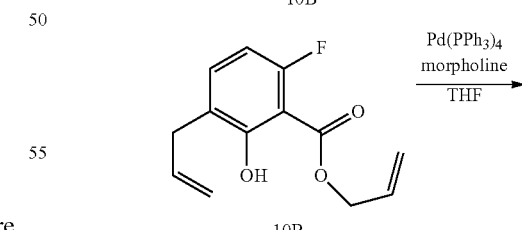

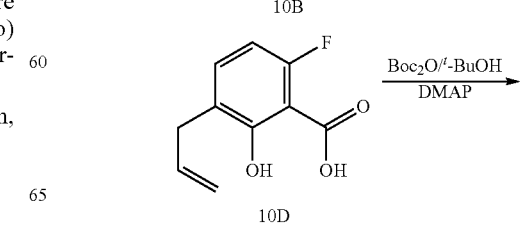

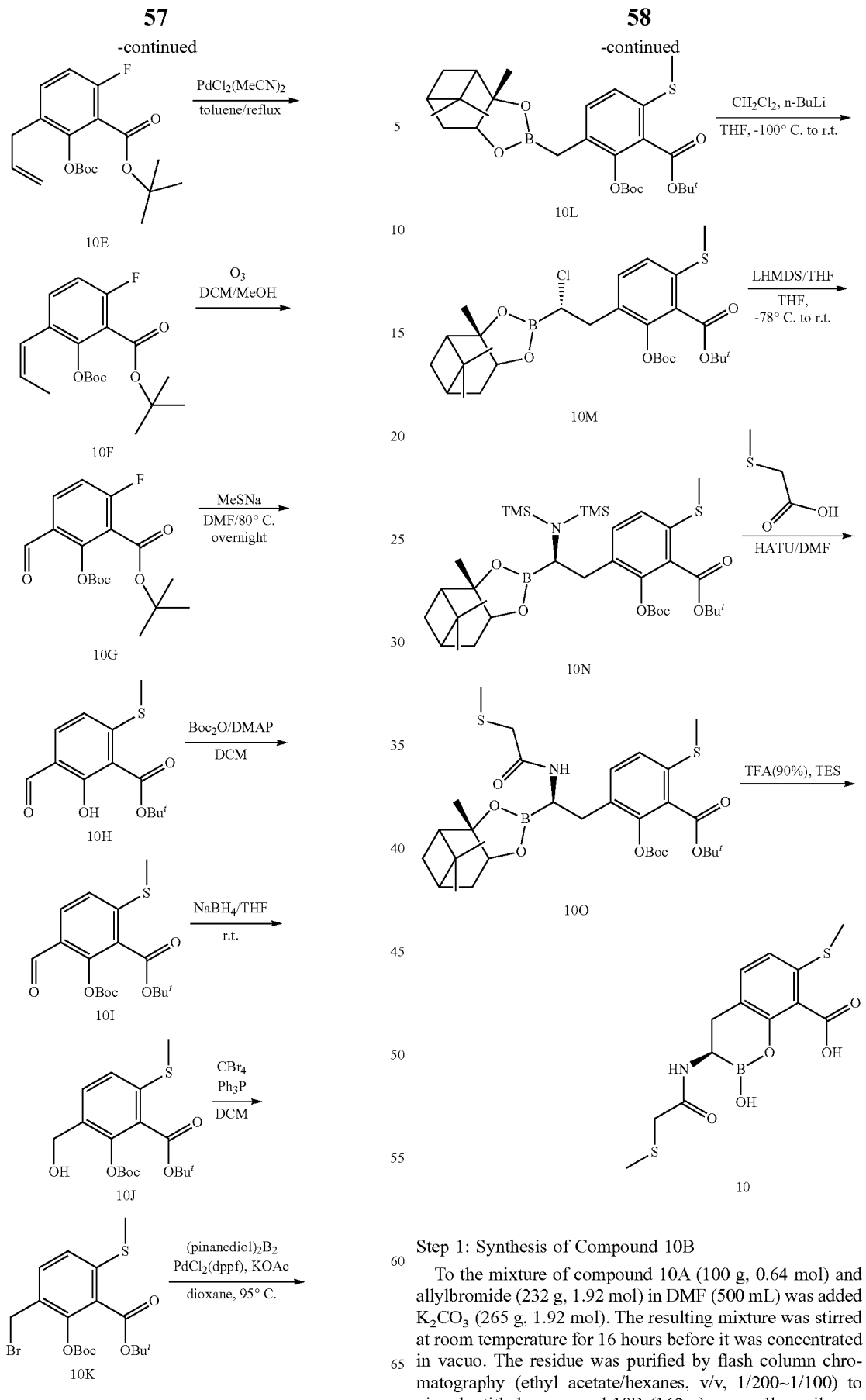
Step 1: Synthesis of Compound 10B
To the mixture of compound 10A (100 g, 0.64 mol) and allylbromide (232 g, 1.92 mol) in DMF (500 mL) was added K₂CO₃ (265 g, 1.92 mol). The resulting mixture was stirred at room temperature for 16 hours before it was concentrated in vacuo. The residue was purified by flash column chromatography (ethyl acetate/hexanes, v/v, 1/200~1/100) to give the titled compound 10B (162 g) as a yellow oil.

Step 2: Synthesis of Compound 10C

Compound 10B (162 g, 0.64 mol) was heated up to 200° C. for 8 hours under nitrogen. The resulting mixture was purified using column chromatography (ethyl acetate/hexanes, v/v, 1/200~1/100) to give the titled compound 10C (153 g) as yellow oil.

Step 3: Synthesis of Compound 10D

To the solution of 10C (153 g, 0.64 mol) in THF (1.2 L) was added Pd(PPh$_3$)$_4$ (22 g, 19.2 mmol) and morpholine (557 g, 6.4 mmol). The resulting solution was stirred at room temperature for two days. The reaction mixture was concentrated to dryness and purified by column chromatography (ethyl acetate/hexanes, v/v, 1/20~1/8) to obtain the titled compound 10D (101 g, 80% yield) as slightly yellow oil.

$^1$H-NMR (400 MHz, CDCl$_3$) δ 11.50 (bs, 1H), 7.45-7.70 (m, 1H), 7.25-7.31 (m, 1H), 6.55-6.62 (m, 1H), 5.93-6.01 (m, 1H), 5.08 (d, 1H), 3.38 (s, 2H).

Step 4: Synthesis of Compound 10E

To the solution of compound 10D (95 g, 0.48 mol) in THF (1.0 L) was added Boc$_2$O (418 g, 1.92 mol), DMAP (2.9 g, 24 mmol) and $^t$BuOH (1.0 L). The resulting solution was stirred at 60° C. overnight before it was concentrated in vacuo. The residue was purified by flash column chromatography (ethyl acetate/hexanes, v/v, 1/200~1/100) to give the titled compound 10E (109 g, 65% yield) as slightly yellow oil.

$^1$H-NMR (400 MHz, CDCl$_3$) δ 7.20-7.26 (m, 1H), 6.92-6.97 (m, 1H), 5.85-5.90 (m, 1H), 5.05-5.11 (m, 2H), 3.30 (d, 2H), 1.57 (s, 9H), 1.53 (s, 9H).

Step 5: Synthesis of Compound 10F

The solution of 10E (109 g, 0.31 mol) and PdCl$_2$(MeCN)$_2$ (4.0 g, 15.5 mmol) in toluene (500 mL) was heated at 100° C. for 3 hours. After concentration, the residue was purified by flash column chromatography (ethyl acetate/hexanes, v/v, 1/200~1/100) to give the titled compound 10F (99 g, 90% yield) as colorless oil, which contains some Boc-depleted side-product.

$^1$H-NMR (400 MHz, CDCl$_3$) δ 7.44-7.49 (m, 1H), 6.92-6.97 (m, 1H), 6.34-6.39 (m, 1H), 6.16-6.20 (m, 1H), 1.87 (d, 3H), 3.30 (d, 2H), 1.57 (s, 9H), 1.53 (s, 9H).

Step 6: Synthesis of Compound 10G

To the solution of 1OF (27 g, 77 mmol, contains some Boc-depleted side product) in MeOH (100 mL) and DCM (500 mL) was bubbled ozone gas (generated is situ from oxygen) at −78° C. until light blue color appeared. Nitrogen gas was bubbled in to remove the blue color and then Me$_2$S (50 mL) was added in. The resulting solution was slowly warmed up to room temperature overnight. After concentration, the residue was purified by column chromatography (ethyl acetate/hexanes, v/v, 1/50~1/20) to obtain the titled compound 10G (20 g, 76% yield, contains some Boc-depleted side product) as slightly yellow oil.

$^1$H-NMR (400 MHz, CDCl$_3$) δ 10.10 (s, 1H), 7.95 (dd, 1H), 7.14 (dd, 1H), 1.59 (s, 9H), 1.57 (s, 9H).

Step 7: Synthesis of Compound 10H

To the solution of 10G (19 g, 56 mmol, contains some Boc-depleted side product) in DMF (150 mL) was added NaSMe (11.8 g, 168 mmol). The resulting solution was stirred at 80° C. overnight, cooled to r.t., concentrated to small volume, and the pH was adjust to 5 with 1 N HCl solution, extracted with EtOAc, washed with water and brine, evaporated to dryness, the residue was purified by column chromatography (ethyl acetate/hexanes, v/v, 1/20~1/10) to obtain the titled compound 10H (9.0 g, 59% yield) as slightly yellow oil.

$^1$H-NMR (400 MHz, CDCl$_3$) δ 12.03 (s, 1H), 10.14 (s, 1H), 7.67 (d, 1H), 6.79 (d, 1H), 2.48 (s, 3H), 1.65 (s, 9H).

Step 8: Synthesis of Compound 10I

To the solution of compound 10H (9.0 g, 34 mmol) in THF (50 mL) was added Boc$_2$O (7.4 g, 34 mol), DMAP (210 mg, 1.7 mmol) and $^t$BuOH (50 mL). The resulting solution was stirred at 60° C. overnight before it was concentrated in vacuo. The residue was purified by flash column chromatography (ethyl acetate/hexanes, v/v, 1/200~1/100) to give the titled compound 10I (9.6 g, 78% yield) as slightly yellow oil.

$^1$H-NMR (400 MHz, CDCl$_3$) δ 10.00 (s, 1H), 7.82 (d, 1H), 7.21 (d, 1H), 2.52 (s, 3H), 1.65 (s, 9H), 1.61 (s, 9H).

Step 9: Synthesis of Compound 10J

To the solution of compound 10I (2.95 g, 8.0 mmol) in anhydrous THF (30 mL) was added NaBH$_4$ (240 mg, 6.4 mmol). The resulting solution was stirred at room temperature for 40 minutes before it was quenched with saturated NH$_4$Cl solution. The reaction mixture was extracted with EtOAc three times, after concentration in vacuo, the residue was purified by flash column chromatography (ethyl acetate/hexanes, v/v, 1/20~1/5) to give the titled compound 10J (1.5 g, 51% yield) as colorless oil.

$^1$H-NMR (400 MHz, CDCl$_3$) δ 7.47 (d, 1H), 7.20 (d, 1H), 4.55 (s, 2H), 2.47 (s, 3H), 1.65 (s, 9H), 1.61 (s, 9H).

Step 10: Synthesis of Compound 10K

To the solution of compound 10J (1.5 g, 4.0 mmol) in DCM (15 mL) was added CBr$_4$ (1.99 g, 6.0 mmol), followed by PPh$_3$ (1.57 g, 6.0 mmol). The resulting reaction mixture was stirred at room temperature for one hour before it was concentration in vacuo to dryness. The residue was purified by flash column chromatography (ethyl acetate/hexanes, v/v, 1/200~1/100) to give the titled compound 10K (1.4 g, 81% yield) as yellow solid.

$^1$H-NMR (400 MHz, CDCl$_3$) δ 7.40 (d, 1H), 7.13 (d, 1H), 4.41 (s, 2H), 2.46 (s, 3H), 1.60 (s, 9H), 1.55 (s, 9H).

Step 11: Synthesis of Compound 10L

The mixture of compound 10K (1.4 g, 3.2 mmol), bis (pinanediolato)diboron (1.03 g, 2.88 mmol) (WO 2004/076467), PdCl$_2$(dppf) (130 mg, 0.16 mmol) and KOAc (940 mg, 9.6 mmol) in dioxane (10 mL) was flushed with nitrogen (3 times) and then stirred at 100° C. for 10 hours before it was concentration in vacuo to dryness. The residue was purified by flash column chromatography (ethyl acetate/hexanes, v/v, 1/200~1/100) to give the titled compound 10L (0.77 g, 45% yield) as slightly yellow oil.

MS calcd for (C$_{28}$H$_{41}$BO$_7$S): 532.

MS (ESI, positive) found: (M+1): 533.

Step 12: Synthesis of Compound 10M

To a solution of CH$_2$Cl$_2$ (0.18 mL, 2.9 mmol) in THF (20 mL) at −100° C. was added 2.5 M n-butyl lithium in hexane (0.8 mL, 2.03 mmol) slowly under nitrogen and down the inside wall of the flask, maintaining the temperature below −90° C. The reaction mixture was stirred at −100° C. for another 30 minutes before the addition of compound 10L (0.77 g, 1.45 mmol) in THF (10 mL) at −90° C. and then the reaction was allowed to warm to room temperature where it was stirred for 16 h. The reaction was concentrated in vacuo directly to dryness and purified by column chromatography (100% hexane-20% EtOAc-hexane) to obtain the titled compound 10M (639 mg, 76% yield) as slightly yellow oil.

MS calcd for (C$_{29}$H$_{42}$BClO$_7$S): 580.

MS (ESI, positive) found: (M+1): 581.

Step 13: Synthesis of Compound 10N

To the solution of compound 10M (639 mg, 1.1 mmol) in THF (anhydrous, 15 mL) was added LiHMDS solution (1.21 mL, 1.0 M in hexane, 1.1 eq) at −78° C. in 15 minutes. The resulting solution was slowly warmed up to room temperature in 24 hours. The reaction solution was concentrated in vacuo. The residue was diluted with 20 mL hexanes and stirred for 20 minutes. The solid was filtered off by Celite and the solution was concentrated to give crude compound 10N as yellow oil (415 mg), which was directly used for next step without further purification.

Step 14: Synthesis of Compound 10O

To the solution of (methylthio)acetic acid (75 mg, 1.2 eq) in DMF (5 mL) was added HATU (268 mg, 1.2 eq) at 0° C. After 15 minutes, the above solution was added into compound 10N (415 mg). After stirring at room temperature for 2 hours, the mixture was diluted with EtOAc/hexanes and washed with saturated NH$_4$Cl and water. The organic layer was concentrated to dryness and purified by column chromatography (100% hexane-20% EtOAc-hexane) to obtain the titled compound 10O (130 mg, 18% yield over two steps) as slightly yellow oil.

MS calcd for ($C_{32}H_{48}BNO_8S_2$): 649.

MS (ESI, positive) found: (M+1): 650.

MS (ESI, negative) found: (M−1): 648.

Step 15: Synthesis of Compound 10

To the mixture of compound 10O (130 mg, 0.2 mmol) and triethylsilane (232 mg, 2 mmol) was added 90% TFA (3 mL). After stirring at room temperature for 2 hours, the reaction mixture was concentrated to dryness and purified by prep-HPLC (C18, acetonitrile and water as mobile phases, 0.1% formic acid) to obtain the titled compound 10 (10 mg) as a white solid.

MS calcd for ($C_{13}H_{16}BNO_5S_2$): 341.

MS (ESI, positive) found: (M+1): 342.

MS (ESI, negative) found: (M−1): 341.

$^1$H-NMR (400 MHz, CD$_3$OD) δ 7.12 (d, 1H), 6.86 (d, 1H), 3.23 (s, 2H), 3.20 (m, 1H), 2.88 (m, 2H), 2.37 (s, 3H), 1.86 (s, 3H).

Example 11: (R)-7-(azetidin-3-ylthio)-2-hydroxy-3-(2-(methylthio)acetamido)-3,4-dihydro-2H-benzo oxaborinine-8-carboxylic acid

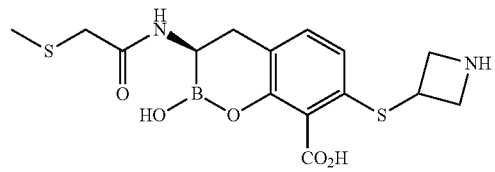

11

Compound 11 was prepared following the procedure described in Example 10 except replacing the MeSNa in step 7 with sodium azetidine-3-thiolate.

$^1$H-NMR (400 MHz, CD$_3$OD) δ 7.13 (d, 1H), 6.82 (d, 1H), 4.36-4.43 (m, 2H), 4.25-4.30 (m, 1H), 3.90-3.99 (m, 2H), 3.24 (s, 2H), 3.19 (s, 1H), 2.94 (s, 2H), 1.82 (s, 3H).

MS calcd for ($C_{15}H_{19}BN_2O_5S_2$) 382.

MS (ESI, positive) found: (M+1): 383.

MS (ESI, negative) found: (M−1): 381.

Example 12: (R)-2-hydroxy-7-methoxy-3-(2-(methylthio)acetamido)-3,4-dihydro-2H-benzo[e][1,2] oxaborinine-8-carboxylic acid (12)

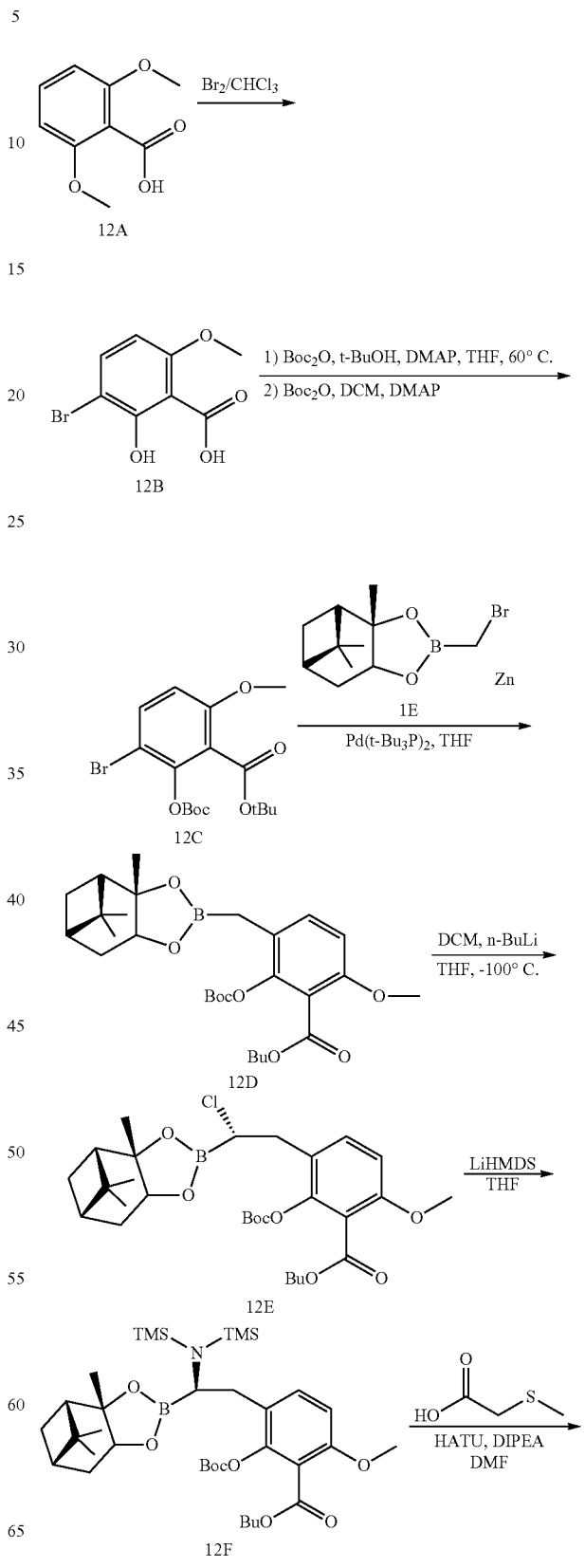

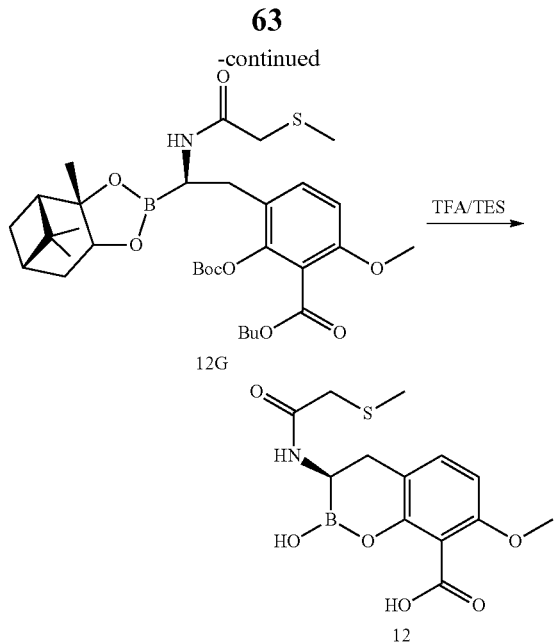

Step 1: Synthesis of 12B

To a solution of 2,6-dimethoxybenzoic acid (12A) (50 g, 0.275 mol) in CHCl3 (1 L) at 0° C. was added dropwise bromine (14.4 mL, 0.263 mol). The reaction mixture was stirred at 25° C. for 30 hours, before it was concentrated to dryness. The residue was purified by column chromatography (ethyl acetate/hexanes) to afford compound 12B (32.5 g, 48%) as white solid.

Step 2: Synthesis of 12C

To the solution of compound 12B (32.5 g, 0.132 mol) in THF (200 mL) was added Boc2O (114.7 g, 0.526 mol), DMAP (4.8 g, 0.04 mol) and tBuOH (400 mL). The resulting solution was stirred at 60° C. for 6 hours before it was concentrated in vacuo. The residue was quickly passed through a silica gel column (ethyl acetate/hexanes) to give the corresponding t-butyl ester. To the solution of this ester and Boc2O (17 g, 0.078 mol) in DCM (300 mL) was added DMAP (475 mg, 3.89 mmol). The resulting reaction mixture was stirred at room temperature for 1 hour before it was concentrated to dryness. The residue was purified by column chromatography (ethyl acetate/hexanes) to afford compound 12C (52.1 g, 98%) as white solid.

Step 3: Synthesis of 12D

To a mixture of Zn powder (20 g, 0.302 mol) and compound 1E (100 mg, 0.37 mmol) in anhydrous THF (100 mL) was added DIBAL-H (2.45 mL, 6.05 mmol, 1.5 M in toluene) at room temperature. The mixture was stirred at room temperature for 5 min, then more compound 1E (33 g, 0.121 mol) in anhydrous THF (100 mL) was added dropwise into the mixture over 20 min. The reaction mixture was warmed up to 50° C. and stirred at this temperature for 1 hour before it was settled down at room temperature. The top clear solution was transferred into a mixture of compound 12C (20 g, 50 mmol) and Pd(t-Bu3P)2 (917 mg, 1.79 mmol) in THF (300 mL) at room temperature under N2. After stirring at room temperature for 1 hour, the reaction mixture was concentrated, and purified by column chromatography (ethyl acetate/hexanes) to afford compound 12D (21 g, 81%) as light yellow solid.

Step 4: Synthesis of 12E

To a solution of dichloromethane (4.2 mL, 0.066 mol) in anhydrous THF (200 mL), was added dropwise n-butyl-lithium (2.5 M in hexane, 18.5 mL, 0.046 mol) along the wall of the flask over 1 h at −100° C. (cooled with liquid nitrogen and methanol), while keeping the internal temperature below −90° C. After the addition, the mixture was stirred at −100° C. for 30 min before slow addition of the solution of compound 12D (17 g, 0.033 mol) in anhydrous THF (60 mL) over 1 h at −100° C. The reaction mixture was slowly warmed up to room temperature over a period of 6 hours and stirred overnight. The solvent was evaporated and the residue was purified by column chromatography (ethyl acetate/hexanes) to afford compound 12E (16.5 g, 88%) as light yellow solid.

Step 5: Synthesis of 12F

To a solution of compound 12E (16.5 g, 0.029 mol) in anhydrous THF (160 mL) at −78° C. was added drop-wise LiHMDS (1.0 M in hexane, 35 mL, 0.035 mol) over 60 min. The mixture was stirred at this temperature for 0.5 h, and then warmed up slowly to r.t. and stirred for 8 hours to afford compound 12F in THF solution which was used directly without any workup.

Step 6: Synthesis of 12G

To a solution of 2-(methylthio)acetic acid (3.7 g, 0.035 mol) in anhydrous DMF (100 mL) was added HATU (13.3 g, 0.035 mol). The mixture was stirred at r.t. for 10 min before compound 12F in THF solution (160 mL, 0.029 mol) was added. The reaction mixture was stirred at rt for 15 hours before it was concentrated to about 20 mL. The residue was extracted with EtOAc/hexanes (v/v, 1:1), washed with water and brine, dried over $Na_2SO_4$. It was purified by column chromatography (ethyl acetate/hexanes) to afford compound 12G (13.7 g, 75%) as light yellow solid.

Step 7: Synthesis of 12

A solution of compound 12G (2 g, 3.157 mmol) in TFA (90%)/TES (20 mL/4 mL) was stirred at room temperature overnight before it was evaporated to dryness. The residue oil was suspended in ether, some white solid precipitated out. After filtration, a mixture of 12 and its oligomer (500 mg) was obtained. The filtrate was kept at r.t. for 2 days and filtered again to afford pure 12 (200 mg).

$^1$H NMR (400 MHz, $CD_3OD$) δ 10.04 (bs, 1H), 7.01 (dd, 1H), 6.48 (d, 1H), 3.76 (s, 3H), 3.23 (s, 2H), 3.06 (m, 1H), 2.76-2.86 (m, 2H), 1.83 (s, 3H).

MS calcd for ($C_{13}H_{16}BNO_6S$): 325.

MS (ESI, positive) found: (M+1): 326.

MS (ESI, negative) found: (M−1): 324.

Example 13: (R)-butyryloxymethyl 7-fluoro-2-hydroxy-3-(2-(methylthio)acetamido)-3,4-dihydro-2H-benzo[e][1,2]oxaborinine-8-carboxylate (13)

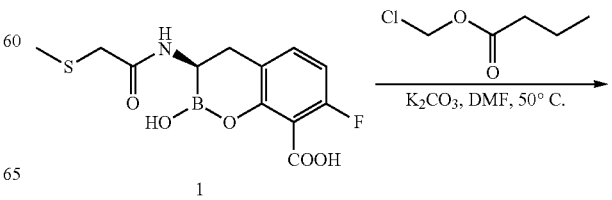

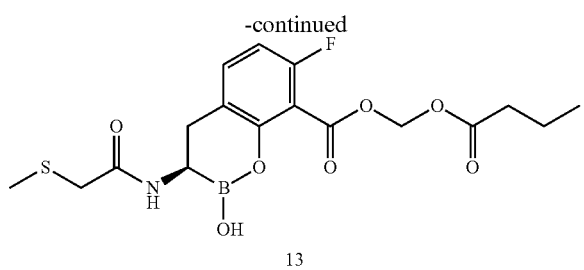

13

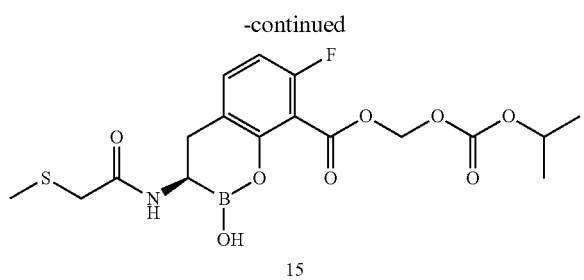

15

To the solution of Compound 1 (156 mg, 0.5 mmol) in DMF (5 mL) was added chloromethyl butanoate (136 mg, 1 mmol), followed by $K_2CO_3$ (103 mg, 0.75 mmol). The resulting mixture was stirred at 50° C. for 18 hours before it was diluted with 25 mL MeOH. After stirred at room temperature for 24 hours, the solution was concentrated to ~6 mL. The residue was purified by purified by prep-HPLC (C18, acetonitrile and water as mobile phases, 0.1% formic acid) to obtain the titled compound 13 (82 mg) as white solid.

$^1$H-NMR (300 MHz, $CD_3OD$) δ 10.20 (bs, 1H), 7.08 (dd, 1H), 6.56 (dd, 1H), 5.92 (s, 2H), 3.22 (s, 2H), 3.12 (m, 1H), 2.84 (d, 2H), 2.39 (t, 2H), 1.80 (s, 3H), 1.66 (m, 2H), 0.97 (t, 3H).

MS calcd for ($C_{17}H_{21}BFNO_7S$): 413.
MS (ESI, positive) found: (M+1): 414.
MS (ESI, negative) found: (M−1): 412.

Example 14: (R)-acetoxymethyl 7-fluoro-2-hydroxy-3-(2-(methylthio)acetamido)-3,4-dihydro-2H-benzo[e][1,2]oxaborinine-8-carboxylate (14)

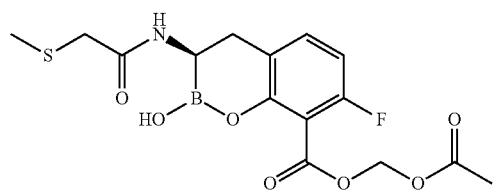

14

Compound 14 was prepared following the same procedure described in example 13 except for replacing the chloromethyl butanoate with chloromethyl acetate.

$^1$H NMR (300 MHz, $CD_3OD$) δ 10.12 (bs, 1H), 7.09 (dd, 1H), 6.57 (d, 1H), 5.91 (s, 2H), 3.23 (s, 2H), 3.12 (m, 1H), 2.84 (m, 2H), 2.11 (s, 3H), 1.81 (s, 3H).

MS calcd for ($C_{15}H_{17}BFNO_7S$): 385.
MS (ESI, positive) found: (M+1): 386.
MS (ESI, negative) found: (M−1): 384.

Example 15: (R)-(isopropoxycarbonyloxy)methyl 7-fluoro-2-hydroxy-3-(2-(methylthio)acetamido)-3,4-dihydro-2H-benzo[e][1,2]oxaborinine-8-carboxylate (15)

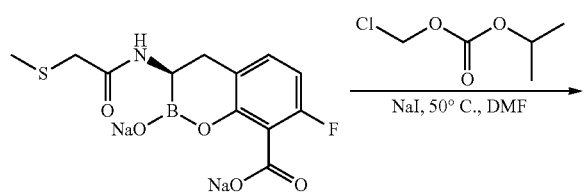

To a solution of sodium salt of 1 (3.0 g, 8.95 mmol, 1.0 eq, prepared by treating 1 in MeCN-water with 1N NaOH to pH7.6-8 and lyophilization) in anhydrous DMF (72 mL) was added chloromethylisopropyl carbonate (2.74 g, 17.9 mmol, 2 eq) and NaI (2.66 g, 17.9 mmol, 2 eq). After the addition, the mixture was stirred at 50° C. for 16 hours before it was diluted with 200 mL MeOH and was added $K_2CO_3$ (618 mg, 4.47 mmol, 0.5 eq). After stirring at 50° C. for 2 h, the solution was cooled down and concentrated to about 80 mL. The resulting mixture was diluted with 300 mL EtOAc and washed with 0.2 N HCl (aq., 300 mL) and water, dried over $Na_2SO_4$. Subsequent prep-HPLC (C18, acetonitrile and water as mobile phases, 0.1% formic acid) and lyophilization provided 1.16 g of 15 as while solid (31% yield).

$^1$H NMR (300 MHz, $CD_3OD$) δ 7.10 (dd, 1H), 6.57 (d, 1H), 5.91 (s, 2H), 3.22 (s, 2H), 3.11 (m, 1H), 2.83 (m, 2H), 1.81 (s, 3H), 1.30 (d, 6H).

MS calcd for ($C_{17}H_{21}BFNO_8S$): 429.
MS (ESI, positive) found: (M+1): 430.
MS (ESI, negative) found: (M−1): 428.

Example 16: (R)-propionyloxymethyl 7-fluoro-2-hydroxy-3-(2-(methylthio)acetamido)-3,4-dihydro-2H-benzo[e][1,2]oxaborinine-8-carboxylate (16)

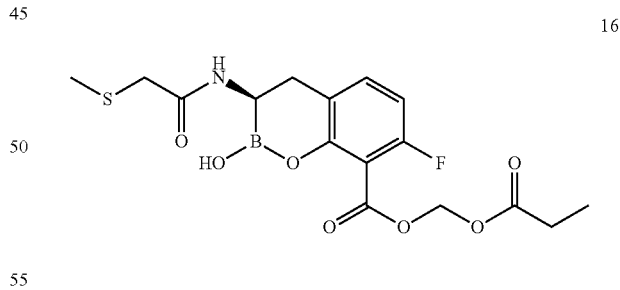

16

Compound 16 was prepared following the same procedure described in example 13 except for replacing the chloromethyl butanoate with chloromethyl propionate.

$^1$H NMR (300 MHz, $CD_3OD$) δ 7.09 (dd, 1H), 6.57 (dd, 1H), 5.92 (s, 2H), 3.23 (s, 2H), 3.12 (m, 1H), 2.85 (m, 2H), 2.45 (q, 2H), 1.80 (s, 3H), 1.14 (t, 3H).

MS calcd for ($C_{16}H_{19}BFNO_7S$): 399.
MS (ESI, negative) found: (M−1): 398.

Example 17: (R)-isobutyryloxymethyl 7-fluoro-2-hydroxy-3-(2-(methylthio)acetamido)-3,4-dihydro-2H-benzo[e][1,2]oxaborinine-8-carboxylate (17

17

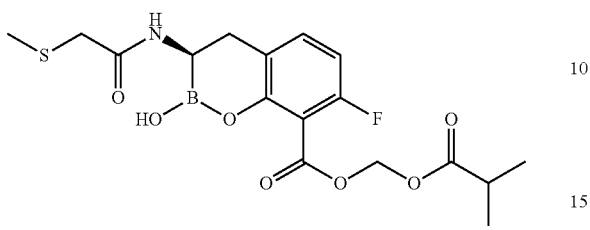

Compound 17 was prepared following the same procedure described in example 13 except for replacing the chloromethyl butanoate with chloromethyl isobutyrate.
¹H NMR (300 MHz, CD₃OD) δ 7.09 (dd, 1H), 6.57 (dd, 1H), 5.93 (s, 2H), 3.22 (s, 2H), 3.11 (m, 1H), 2.83 (m, 2H), 2.63 (m, 1H), 1.81 (s, 3H), 1.18 (d, 6H).
MS calcd for (C₁₇H₂₁BFNO₇S): 413.
MS (ESI, negative) found: (M−1): 412.

Example 18: (R)-pivaloyloxymethyl 7-fluoro-2-hydroxy-3-(2-(methylthio)acetamido)-3,4-dihydro-2H-benzo[e][1,2]oxaborinine-8-carboxylate (18)

18

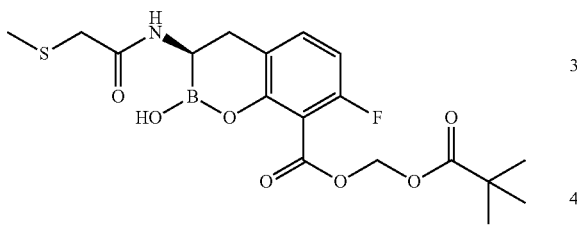

Compound 18 was prepared following the same procedure described in example 13 except for replacing the chloromethyl butanoate with chloromethyl pivalate.
¹H NMR (300 MHz, CD₃OD) δ 7.09 (dd, 1H), 6.57 (dd, 1H), 5.93 (s, 2H), 3.22 (s, 2H), 3.11 (m, 1H), 2.83 (m, 2H), 1.81 (s, 3H), 1.23 (s, 9H).
MS calcd for (C₁₈H₂₃BFNO₇S): 427.
MS (ESI, negative) found: (M−1): 426.

Example 19: (R)-(ethoxycarbonyloxy)methyl 7-fluoro-2-hydroxy-3-(2-(methylthio)acetamido)-3,4-dihydro-2H-benzo[e][1,2]oxaborinine-8-carboxylate (19)

19

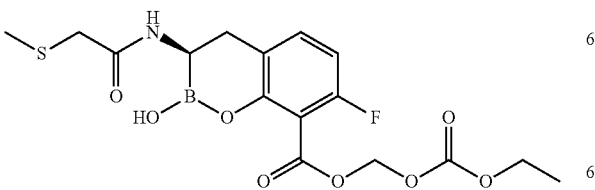

Compound 19 was prepared following the same procedure described in example 13 except for replacing the chloromethyl butanoate with chloromethyl ethyl carbonate.
¹H NMR (300 MHz, CD₃OD) δ 7.109 (dd, 1H), 6.57 (dd, 1H), 5.92 (s, 2H), 4.24 (q, 2H), 3.23 (s, 2H), 3.11 (m, 1H), 2.83 (m, 2H), 1.81 (s, 3H), 1.30 (t, 3H).
MS calcd for (C₁₆H₁₉BFNO₈S): 415.
MS (ESI, negative) found: (M−1): 414.

Example 20: (R)-2-hydroxy-7-(2-hydroxyethoxy)-3-(2-(methylthio)acetamido)-3,4-dihydro-2H-benzo[e][1,2]oxaborinine-8-carboxylic acid (20)

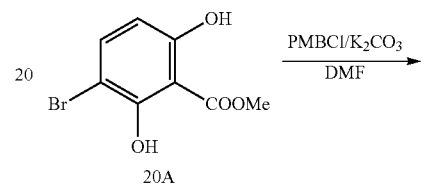

20A

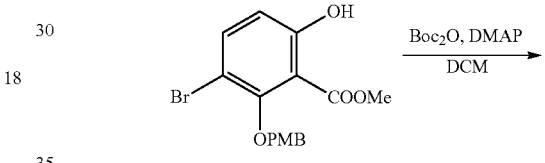

20B

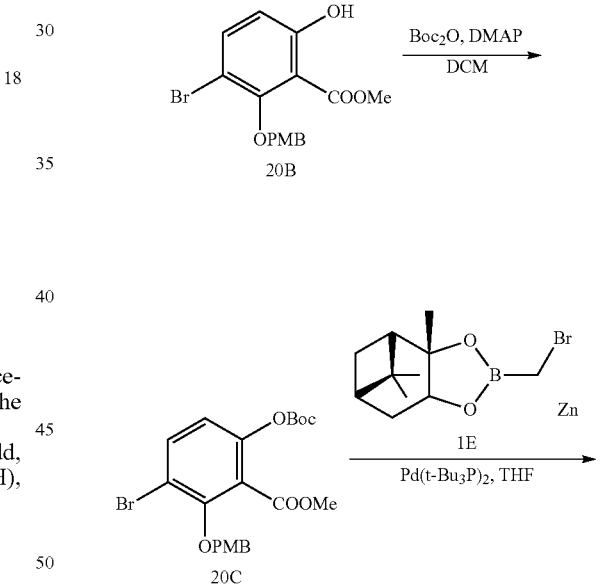

20C

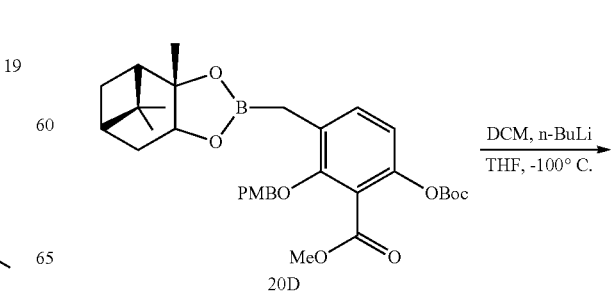

20D

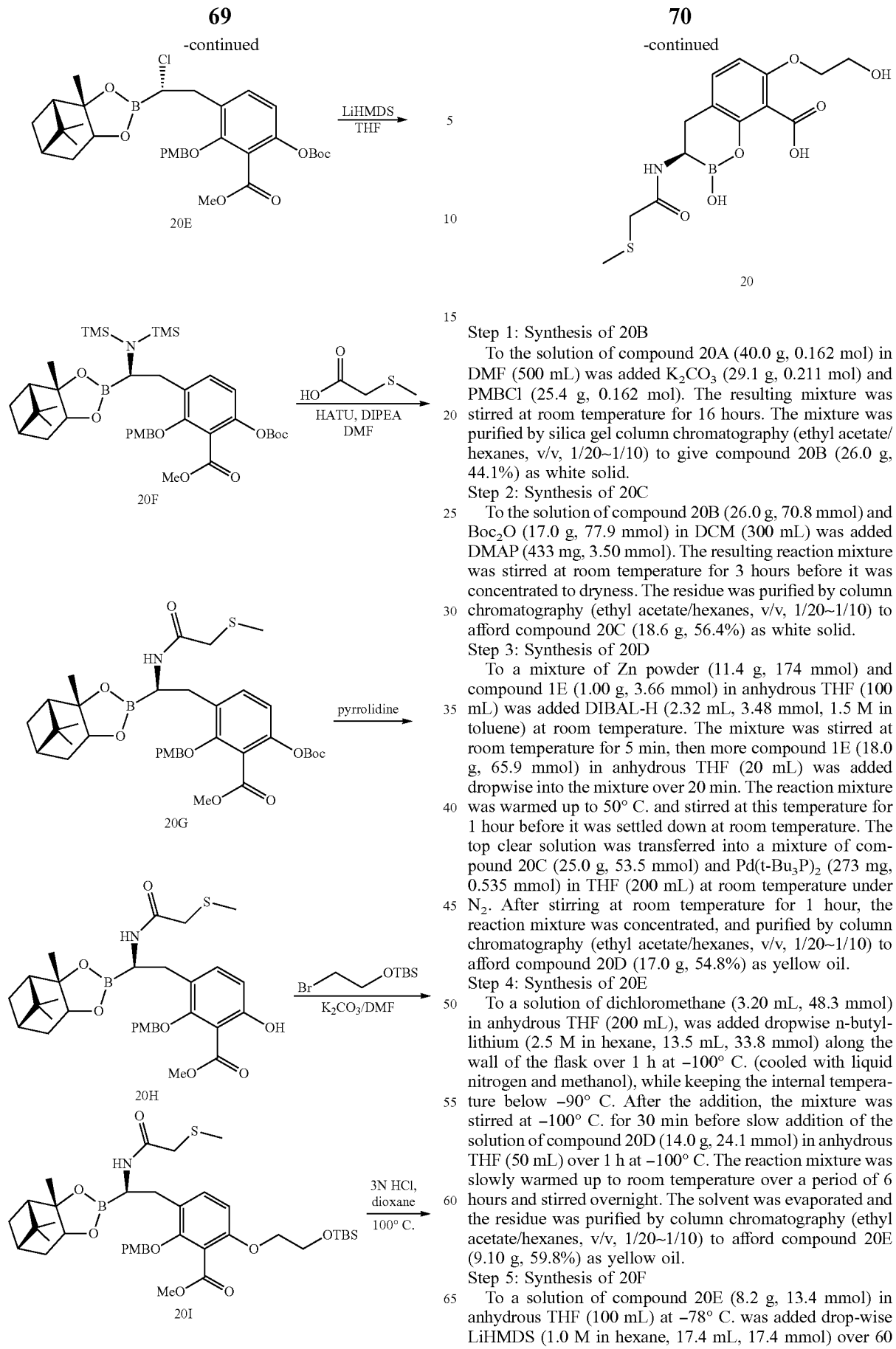

Step 1: Synthesis of 20B

To the solution of compound 20A (40.0 g, 0.162 mol) in DMF (500 mL) was added $K_2CO_3$ (29.1 g, 0.211 mol) and PMBCl (25.4 g, 0.162 mol). The resulting mixture was stirred at room temperature for 16 hours. The mixture was purified by silica gel column chromatography (ethyl acetate/hexanes, v/v, 1/20~1/10) to give compound 20B (26.0 g, 44.1%) as white solid.

Step 2: Synthesis of 20C

To the solution of compound 20B (26.0 g, 70.8 mmol) and $Boc_2O$ (17.0 g, 77.9 mmol) in DCM (300 mL) was added DMAP (433 mg, 3.50 mmol). The resulting reaction mixture was stirred at room temperature for 3 hours before it was concentrated to dryness. The residue was purified by column chromatography (ethyl acetate/hexanes, v/v, 1/20~1/10) to afford compound 20C (18.6 g, 56.4%) as white solid.

Step 3: Synthesis of 20D

To a mixture of Zn powder (11.4 g, 174 mmol) and compound 1E (1.00 g, 3.66 mmol) in anhydrous THF (100 mL) was added DIBAL-H (2.32 mL, 3.48 mmol, 1.5 M in toluene) at room temperature. The mixture was stirred at room temperature for 5 min, then more compound 1E (18.0 g, 65.9 mmol) in anhydrous THF (20 mL) was added dropwise into the mixture over 20 min. The reaction mixture was warmed up to 50° C. and stirred at this temperature for 1 hour before it was settled down at room temperature. The top clear solution was transferred into a mixture of compound 20C (25.0 g, 53.5 mmol) and $Pd(t-Bu_3P)_2$ (273 mg, 0.535 mmol) in THF (200 mL) at room temperature under $N_2$. After stirring at room temperature for 1 hour, the reaction mixture was concentrated, and purified by column chromatography (ethyl acetate/hexanes, v/v, 1/20~1/10) to afford compound 20D (17.0 g, 54.8%) as yellow oil.

Step 4: Synthesis of 20E

To a solution of dichloromethane (3.20 mL, 48.3 mmol) in anhydrous THF (200 mL), was added dropwise n-butyl-lithium (2.5 M in hexane, 13.5 mL, 33.8 mmol) along the wall of the flask over 1 h at −100° C. (cooled with liquid nitrogen and methanol), while keeping the internal temperature below −90° C. After the addition, the mixture was stirred at −100° C. for 30 min before slow addition of the solution of compound 20D (14.0 g, 24.1 mmol) in anhydrous THF (50 mL) over 1 h at −100° C. The reaction mixture was slowly warmed up to room temperature over a period of 6 hours and stirred overnight. The solvent was evaporated and the residue was purified by column chromatography (ethyl acetate/hexanes, v/v, 1/20~1/10) to afford compound 20E (9.10 g, 59.8%) as yellow oil.

Step 5: Synthesis of 20F

To a solution of compound 20E (8.2 g, 13.4 mmol) in anhydrous THF (100 mL) at −78° C. was added drop-wise LiHMDS (1.0 M in hexane, 17.4 mL, 17.4 mmol) over 60 min, the mixture was stirred at this temperature for 0.5 h, and then warmed up slowly to r.t. and stirred at rt for 16 hours to afford compound 20F in THF solution which was used directly without any workup.

Step 6: Synthesis of 20G

To a solution of 2-(methylthio)acetic acid (2.13 g, 20.1 mmol) in anhydrous DMF (100 mL) was added HATU (7.64 g, 20.1 mmol). The mixture was stirred at r.t. for 10 min before compound 20F in THF solution (150 mL, 13.4 mmol) was added. The reaction mixture was stirred at rt for 2 hours before it was concentrated to about 150 mL. The residue was extracted with EtOAc/hexanes (v/v, 4/1), washed with water and brine, dried over $Na_2SO_4$ It was purified by column chromatography (ethyl acetate/hexanes, v/v, 1/10~1/3) to afford compound 20G (4.6 g, 49.3% over two steps) as yellow oil.

Step 7: Synthesis of 20H

A solution of compound 20G (1.02 g, 1.46 mmol) in THF (50 mL) was added pyrrolidine (208 mg, 2.9 mmol). The resulting solution was stirred at 50° C. for two hours before it was evaporated to dryness. The residue was purified by column chromatography (ethyl acetate/hexanes, v/v, 1/10~1/2) to afford compound 20H (670 mg, 76.9%) as yellow solid.

Step 8: Synthesis of 20I

A solution of compound 20H (420 mg, 0.7 mmol) in DMF (6 mL) was added (2-bromoethoxy)(tert-butyl)dimethylsilane (504 mg, 2.1 mmol) and $K_2CO_3$ (389 mg, 2.8 mmol). The resulting solution was stirred at 40° C. for 16 hours. The mixture was purified by column chromatography (ethyl acetate/hexanes, v/v, 1/10~1/3) to afford compound 20I (350 mg, 65.8%) as yellow oil.

Step 9: Synthesis of 20

A solution of compound 20I (180 mg, 0.24 mmol) in dioxane (4 mL) was added 3 N aqueous HCl solution (2 mL). The resulting solution was stirred at 100° C. for 3 hours before it was concentrated to dryness. The residue was purified by prep-HPLC (C18, acetonitrile and water as mobile phases, 0.1% TFA) to obtain the titled compound 20 (8.5 mg) as white solid.

$^1$H NMR (400 MHz, $CD_3OD$) δ 10.07 (s, 1H), 7.01 (d, 1H), 6.50 (d, 1H), 4.05 (s, 2H), 3.81 (s, 2H), 3.30 (s, 2H), 3.11 (s, 1H), 2.87-2.76 (m, 2H), 1.82 (m, 3H).

MS calcd for ($C_{14}H_{18}BNO_7S$): 355.

MS (ESI, positive) found: (M+1): 356.

MS (ESI, negative) found: (M−1): 354.

Example 21: (R)-7-(5-amino-1,3,4-thiadiazol-2-ylthio)-2-hydroxy-3-(2-(methylthio)acetamido)-3,4-dihydro-2H-benzo[e][1,2]oxaborinine-8-carboxylic acid (21)

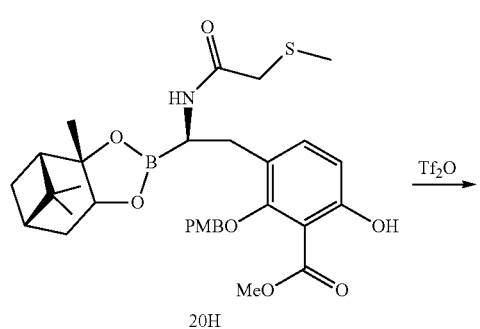

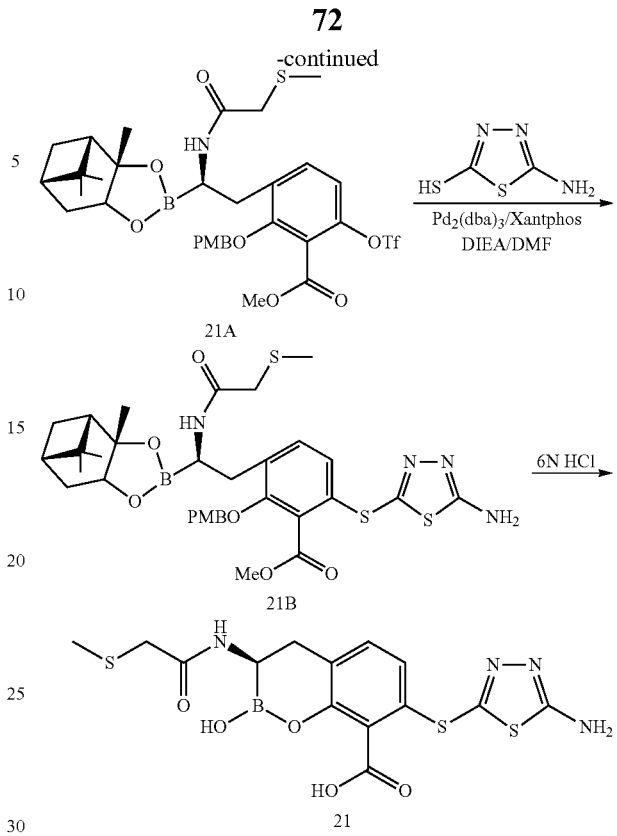

Step 1: Synthesis of Compound 21A

To the solution of compound 20H (570 mg, 0.95 mmol) in DCM (30 mL) was added DIPEA (306 mg, 2.38 mmol). The solution was cooled to −30° C. and $Tf_2O$ (323 mg, 1.15 mmol) was added dropwise. The reaction mixture was stirred at r.t for 1 hour before it was concentrated to dryness. The residue was purified by column chromatography (ethyl acetate/hexanes, v/v, 1/10~1/3) to afford compound 21A (420 mg, 60.6%) as yellow oil.

Step 2: Synthesis of Compound 21B

To the mixture of compound 21A (320 mg, 0.439 mmol), compound 5-amino-1,3,4-thiadiazole-2-thiol (70 mg, 0.527 mmol), $Pd_2(dba)_3$ (40 mg, 0.044 mmol) and Xanphos (51 mg, 0.088 mmol) in DMF (5 mL) was added DIPEA (113 mg, 0.878 mmol) under nitrogen. The reaction mixture was stirred at 115° C. for 2 hours. The mixture was concentrated to afford 580 mg crude 21B which was used directly without any workup.

Step 3: Synthesis of 21

A solution of compound 21B (580 mg, 0.439 mmol, crude) in dioxane (4 mL) was added 6 N aqueous HCl solution (4 mL). The resulting solution was stirred at 100° C. for 7 hours before it was concentrated to dryness. The residue was purified by prep-HPLC (C18, acetonitrile and water as mobile phases, 0.1% TFA) to obtain the titled compound 21 (13.6 mg) as white solid.

$^1$H NMR (400 MHz, $CD_3OD$) δ 10.2 (s, 1H), 7.15 (d, 1H), 6.86 (d, 1H), 3.24-2.21 (m, 3H), 2.90 (s, 2H), 1.81 (s, 3H).

MS calcd for ($C_{14}H_{15}BN_4O_5S_3$): 426.

MS (ESI, positive) found: (M+1): 427.

MS (ESI, negative) found: (M−1): 425.

Example 22: (R)-7-(2-amino-2-oxoethylthio)-2-hydroxy-3-(2-(methylthio)acetamido)-3,4-dihydro-2H-benzo[e][1,2]oxaborinine-8-carboxylic acid (22)

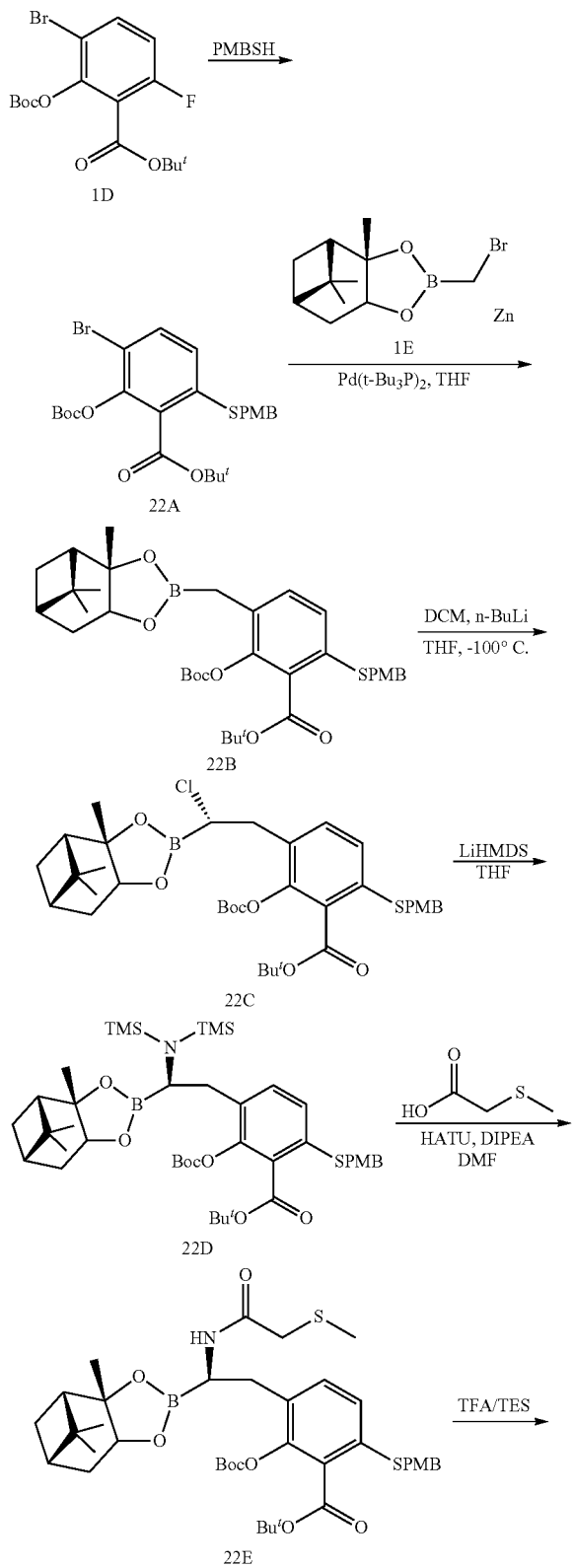

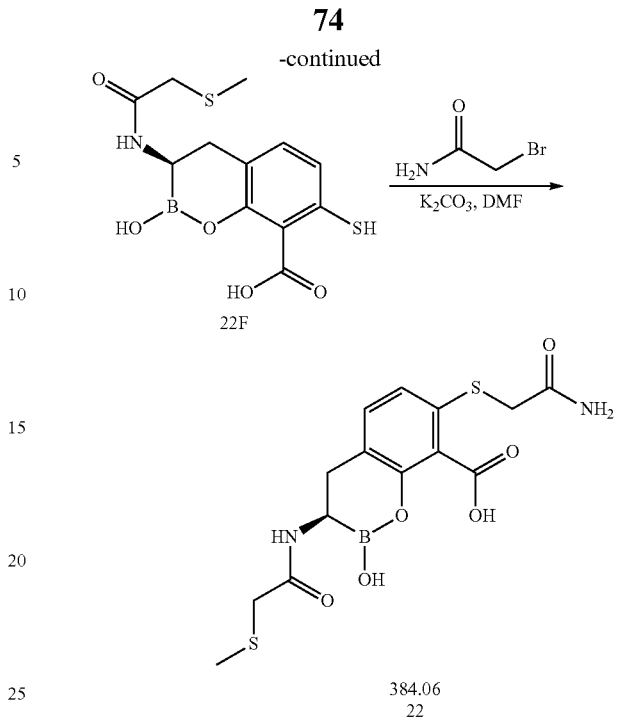

Steps 1-3: Synthesis of 1D

Compound 1D was synthesized as described in example 1.

Step 4: Synthesis of 22A

To the solution of compound 1D (20 g, 0.051 mol) in DMF (300 mL) was added PMBSH (9.47 g, 0.062 mol) and NaH (1.49 g, 0.062 mol). The resulting solution was stirred at 25° C. for 24 hours. The mixture was purified by silica gel column chromatography (ethyl acetate/hexanes, v/v, 1/20~1/10) to give compound 22A (15.2 g, 57%) as yellow oil.

Step 5: Synthesis of 22B

To a mixture of Zn powder (4.8 g, 0.075 mol) and compound 1E (100 mg, 30 mmol) in anhydrous THF (25 mL) was added DIBAL-H (1 mL, 1.5 mmol, 1.5 M in toluene) at room temperature. The mixture was stirred at room temperature for 5 min, then more compound 1E (8.09 g, 29 mmol) in anhydrous THF (25 mL) was added dropwise into the mixture over 20 min. The reaction mixture was warmed up to 50° C. and stirred at this temperature for 1 hour before it was settled down at room temperature. The top clear solution was transferred into a mixture of compound 22A (12 g, 22.9 mmol) and Pd(t-Bu$_3$P)$_2$ (351 mg, 0.687 mmol) in THF (150 mL) at room temperature under N$_2$. After stirring at room temperature for 1 hour, the reaction mixture was concentrated, and purified by column chromatography (ethyl acetate/hexanes, v/v, 1/20~1/10) to afford compound 22B (9.7 g, 66%) as yellow oil.

Step 6: Synthesis of 22C

To a solution of dichloromethane (1.95 mL, 0.031 mol) in anhydrous THF (200 mL), was added dropwise n-butyllithium (2.5 M in hexane, 8.5 mL, 0.022 mol) along the wall of the flask over 1 h at −100° C. (cooled with liquid nitrogen and methanol), while keeping the internal temperature below −90° C. After the addition, the mixture was stirred at −100° C. for 30 min before slow addition of the solution of compound 22B (9.7 g, 0.015 mol) in anhydrous THF (50 mL) over 1 h at −100° C. The reaction mixture was slowly warmed up to room temperature over a period of 6 hours and stirred overnight. The solvent was evaporated and the residue was purified by column chromatography (ethyl acetate/hexanes, v/v, 1/20~1/10) to afford compound C (8.5 g, 82.6%) as oil.

Step 7: Synthesis of 22D

To a solution of compound 22C (8.5 g, 0.012 mol) in anhydrous THF (80 mL) at −78° C. was added drop-wise LiHMDS (1.0 M in hexane, 24.8 mL, 0.025 mol) over 60 min. The mixture was stirred at this temperature for 0.5 h, and then warmed up slowly to r.t. and stirred at rt for 16 hours to afford compound 22D in THF solution, which was used directly without any workup.

Step 8: Synthesis of 22E

To a solution of 2-(methylthio)acetic acid (1.71 g, 0.016 mol) in anhydrous DMF (50 mL) was added HATU (5.66 g, 0.015 mol). The mixture was stirred at r.t. for 10 min before compound 22D in THF solution (100 mL, 0.012 mol) was added. The reaction mixture was stirred at rt for 15 hours before it was concentrated to about 50 mL. The residue was extracted with EtOAc/hexanes (v/v, 1/1), washed with water and brine, dried over $Na_2SO_4$ It was purified by column chromatography (ethyl acetate/hexanes, v/v, 1/10~1/3) to afford compound 22E (2.94 g, 33%) as oil.

Step 9: Synthesis of 22F

A solution of compound 22E (2.94 g, 4.0 mmol) in TFA (90%)/TES (28 mL/4 mL) was stirred at room temperature overnight before it was evaporated to dryness. The residue was washed with ether (3×) to afford crude compound 22F (750 mg) as solid, which was used for next step without further purification.

Step 10: Synthesis of 22

A solution of compound 22F (150 mg, 0.46 mmol) in DMF (2 mL) was added 2-bromoacetamide (32 mg, 0.23 mmol) and $K_2CO_3$ (127 mg, 0.92 mmol). The resulting solution was stirred at 25° C. for 2 hours. The mixture was purified by prep-HPLC (C18, acetonitrile and water as mobile phases, 0.1% formic acid) to obtain the titled compound 22 (13.3 mg) as white solid.

$^1$H NMR (400 MHz, $CD_3OD$) δ 7.09 (d, 1H), 6.94 (d, 1H), 3.58 (s, 2H), 3.24 (s, 2H), 3.18 (s, 1H), 2.87 (s, 2H), 1.76 (s, 3H).

MS calcd for ($C_{14}H_{17}BN_2O_6S_2$): 384.

MS (ESI, positive) found: (M+1): 385.

MS (ESI, negative) found: (M−1): 383.

Example 23: (R)-2-hydroxy-7-(2-hydroxyethylthio)-3-(2-(methylthio)acetamido)-3,4-dihydro-2H-benzo[e][1,2]oxaborinine-8-carboxylic acid (23)

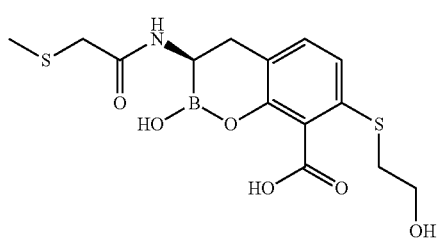

23

Compound 23 was prepared following the procedure described in Example 22 except replacing the 2-bromoacetamide in step 10 with 2-bromoethanol.

$^1$H NMR (400 MHz, $CD_3OD$) δ 7.06 (d, 1H), 6.96 (d, 1H), 3.63 (t, 2H), 3.1-3.16 (3, 4H), 2.97 (t, 2H), 2.86 (s, 2H), 1.81 (s, 3H).

MS calcd for ($C_{14}H_{18}BNO_6S_2$): 371.

MS (ESI, positive) found: (M+1): 372.

MS (ESI, negative) found: (M−1): 370.

Example 24: (R)-2-hydroxy-3-(2-(methylthio)acetamido)-7-(piperidin-4-ylmethylthio)-3,4-dihydro-2H-benzo[e][1,2]oxaborinine-8-carboxylic acid (24)

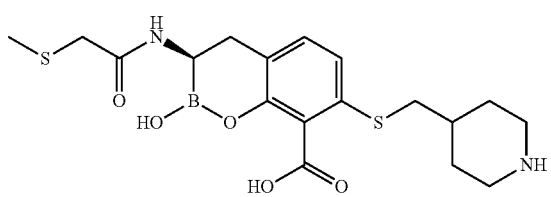

24

Compound 24 was prepared following the procedure described in Example except replacing the 2-bromoacetamide in step 10 with tert-Butyl 4-(bromomethyl)piperidine-1-carboxylate.

$^1$H NMR (400 MHz, $CD_3OD$) δ 7.06 (d, 1H), 6.96 (d, 1H), 3.43-3.16 (m, 7H), 2.95-2.77 (m, 5H), 2.10 (dd, 2H), 1.81 (s, 3H), 1.41 (m, 2H).

MS calcd for ($C_{18}H_{25}BN_2O_5S_2$): 424.

MS (ESI, positive) found: (M+1): 425.

MS (ESI, negative) found: (M−1): 423.

Example 25: (R)-3-(2-(difluoromethylthio)acetamido)-2-hydroxy-7-methoxy-3,4-dihydro-2H-benzo[e][1,2]oxaborinine-8-carboxylic acid (25)

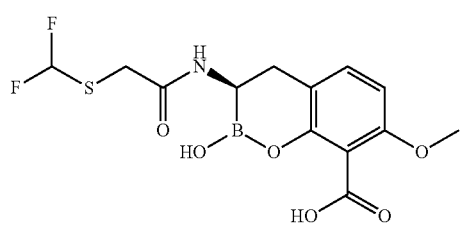

25

Compound 25 was prepared following the procedure described in Example 12 except replacing the 2-(methylthio)acetic acid in step 6 with 2-((difluoromethyl)thio)acetic acid.

$^1$H NMR (400 MHz, $CD_3OD$) δ 7.12-6.75 (m, 2H), 6.47 (d, 1H), 3.86 (s, 3H), 3.68 (s, 2H), 3.30 (s, 1H), 2.83 (q, 2H).

MS calcd for ($C_{13}H_{14}BF_2NO_6S$): 361.

MS (ESI, positive) found: (M+1): 362.

MS (ESI, negative) found: (M−1): 360.

Example 26: (R)-3-(2-(azetidin-3-ylthio)acetamido)-2-hydroxy-7-methoxy-3,4-dihydro-2H-benzo[e][1,2]oxaborinine-8-carboxylic acid (26)

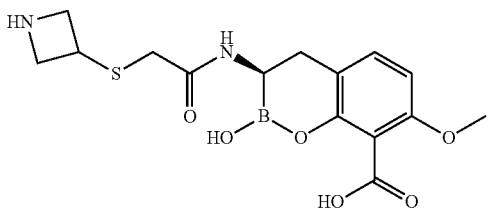

26

Compound 26 was prepared following the procedure described in Example 12 except replacing the 2-(methylthio)acetic acid in step 6 with 2-(azetidin-3-ylthio)acetic acid.

$^1$H NMR (400 MHz, CD$_3$OD) δ 7.02 (d, 1H), 6.49 (d, 1H), 4.36 (s, 1H), 4.24 (s, 1H), 3.84-3.71 (m, 5H), 3.45-3.31 (3, 2H), 3.13 (s, 1H), 2.87-2.76 (m, 2H).
MS calcd for (C$_{15}$H$_{19}$BN$_2$O$_6$S): 366.
MS (ESI, positive) found: (M+1): 367.
MS (ESI, negative) found: (M−1): 365.

Example 27: (R)-3-(3-amino-3-oxopropanamido)-2-hydroxy-7-methoxy-3,4-dihydro-2H-benzo[e][1,2]oxaborinine-8-carboxylic acid (27)

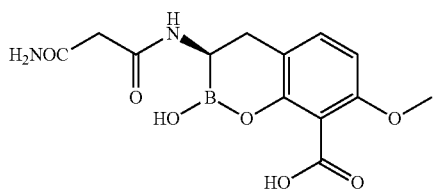

27

Compound 27 was prepared following the procedure described in Example 12 except replacing the 2-(methylthio)acetic acid in step 6 with 3-amino-3-oxopropanoic acid.

$^1$H NMR (400 MHz, CD$_3$OD) δ 10.08 (s, 1H), 6.99 (d, 1H), 6.46 (d, 1H), 3.77 (s, 3H), 3.13 (s, 1H), 2.75 (s, 2H).
MS calcd for (C$_{13}$H$_{15}$BN$_2$O$_7$): 322.
MS (ESI, positive) found: (M+1): 323.
MS (ESI, negative) found: (M−1): 321.

Example 28: (R)-3-(5-amino-1,3,4-thiadiazole-2-carboxamido)-2-hydroxy-7-methoxy-3,4-dihydro-2H-benzo[e][1,2]oxaborinine-8-carboxylic acid (28)

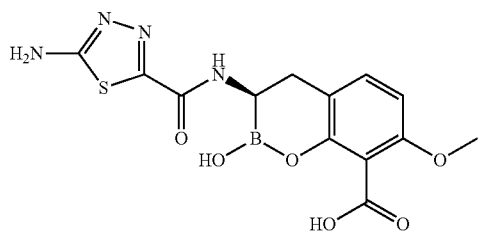

28

Compound 28 was prepared following the procedure described in Example 12 except replacing the 2-(methylthio)acetic acid in step 6 with 5-amino-1,3,4-thiadiazole-2-carboxylic acid.

$^1$H NMR (400 MHz, CD$_3$OD) δ 8.67 (s, 1H), 7.01 (d, 1H), 6.46 (d, 1H), 3.95 (s, 1H), 3.75 (s, 3H), 3.19 (s, 1H), 2.86 (s, 2H).
MS calcd for (C$_{13}$H$_{13}$BN$_4$O$_6$S): 364.
MS (ESI, positive) found: (M+1): 365.
MS (ESI, negative) found: (M−1): 363.

Example 29: (R)-2-hydroxy-7-methoxy-3-(2-(thiophen-2-yl)acetamido)-3,4-dihydro-2H-benzo[e][1,2]oxaborinine-8-carboxylic acid (29)

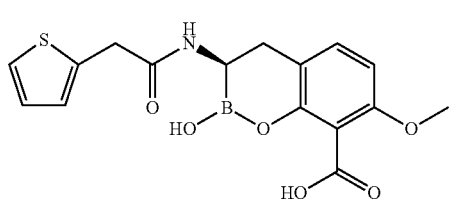

29

Compound 29 was prepared following the procedure described in Example 12 except replacing the 2-(methylthio)acetic acid in step 6 with 2-thiophenacetic acid.

$^1$H NMR (300 MHz, CD$_3$OD) δ 10.0 (s, 1H), 7.24 (dd, 1H), 6.98 (d, 1H), 6.86 (dd, 1H), 6.72-6.71 (m, 1H), 6.45 (d, 1H), 3.84 (s, 2H), 3.78 (s, 3H), 3.08 (s, 1H), 2.79-2.74 (m, 2H).
MS calcd for (C$_{16}$H$_{16}$BNO$_6$S): 361.
MS (ESI, positive) found: (M+1): 362.
MS (ESI, negative) found: (M−1): 360.

Example 30: (R)-7-fluoro-2-hydroxy-3-(2-(thiophen-2-yl)acetamido)-3,4-dihydro-2H-benzo[e][1,2]oxaborinine-8-carboxylic acid (30)

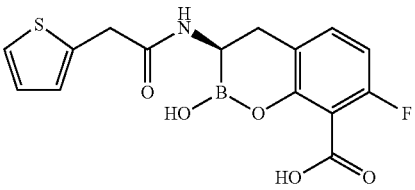

30

Compound 30 was prepared following the procedure described in Example 1 except replacing the 2-(methylthio)acetic acid in step 7 with 2-thiophenacetic acid.

$^1$H NMR (300 MHz, CD$_3$OD) δ 10.1 (s, 1H), 7.22 (dd, 1H), 7.08-7.03 (m, 1H), 6.85 (dd, 1H), 6.71-6.69 (dd, 1H), 6.6-6.54 (m, 1H), 3.84-3.92 (m, 2H), 3.15 (s, 1H), 2.83-2.81 (m, 2H).
MS calcd for (C$_{15}$H$_{13}$BFNO$_5$S): 349.
MS (ESI, positive) found: (M+1): 350.
MS (ESI, negative) found: (M−1): 348.

Example 31: (S)-7-fluoro-2-hydroxy-3-(2-(methylthio)acetamido)-3,4-dihydro-2H-benzo[e][1,2]oxaborinine-8-carboxylic acid (31)

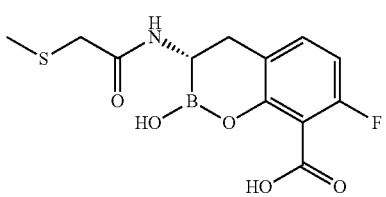

Compound 31 was prepared following the procedure described in Example 1 except replacing the compound 1E in step 4 with corresponding enantiomer made from (−)-pananediol (WO2013/56163).

$^1$H NMR (400 MHz, CD$_3$OD) δ 10.16 (s, 1H), 7.11 (t, 1H), 6.61 (t, 1H), 3.20 (s, 2H), 3.14 (s, 1H), 2.93 (s, 2H), 1.89 (s, 3H).

MS calcd for (C$_{12}$H$_{13}$BFNO$_5$S): 313.
MS (ESI, positive) found: (M+1): 314.
MS (ESI, negative) found: (M−1): 312.

Example 32: (R)-5,7-difluoro-2-hydroxy-3-(2-(methylthio)acetamido)-3,4-dihydro-2H-benzo[e][1,2]oxaborinine-8-carboxylic acid (32)

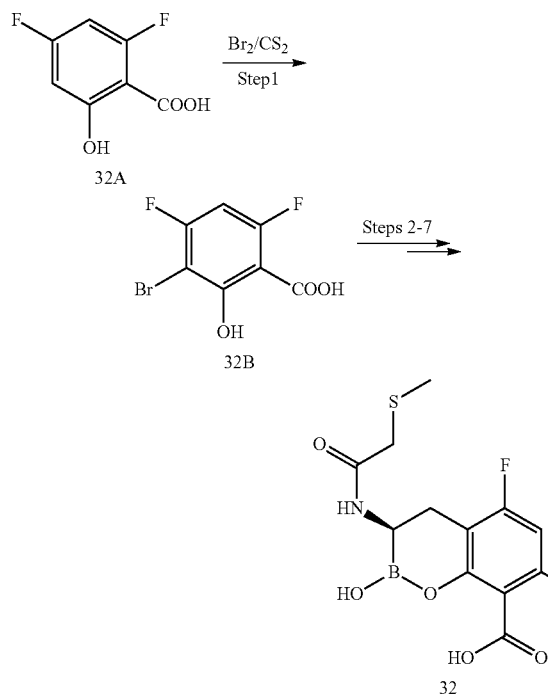

Step 1:

To a solution of 4,6-Difluoro-2-hydroxy benzoic acid (*J. Fluorine Chem.*, 2003, 121, 97-99) 32A (700 mg, 4 mmol) in CS$_2$ (5 mL) at 0° C. under N$_2$ was added bromine (644 mg, 4 mmol) dropwise in CS$_2$ (5 mL), and the mixture was stirred at room temperature overnight. The reaction was then treated with Na$_2$S$_2$O$_3$ (aq.), extracted with ethyl acetate (100 mL). The organic layer was washed with water and brine, dried and concentrated to get 32B (1.2 g, 75%). The crude was used directly to the next step without further purification.

Step 2:

Crude 3-bromo-4,6-difluoro-2-hydroxy benzoic acid was transformed to tert-butyl 3-bromo-2-{[(tert-butoxy)carbonyl]oxy}-4,6-difluorobenzoate by following procedure described in step 4 of example 10.

Steps 3-7:

tert-Butyl 3-bromo-2-{[(tert-butoxy)carbonyl]oxy}-4,6-difluorobenzoate was transformed to 32 in steps 3-7 following procedures described in steps 4-8 of example 1.

$^1$H NMR (400 MHz, CD$_3$OD) δ 10.40 (s, 1H), 6.51 (t, 1H), 3.30 (s, 2H), 3.18-3.15 (m, 2H), 2.56 (dd, 1H), 1.91 (s, 3H).

MS calcd for (C$_{12}$H$_{12}$BF$_2$NO$_5$S): 331.
MS (ESI, positive) found: (M+1): 332.
MS (ESI, negative) found: (M−1): 330.

Example 33: (R)-7-(carboxymethoxy)-2-hydroxy-3-(2-(methylthio)acetamido)-3,4-dihydro-2H-benzo[e][1,2]oxaborinine-8-carboxylic acid (33)

Compound 33 was prepared following the procedure described in Example 20 except replacing the (2-bromoethoxy)(tert-butyl)dimethylsilane in step 8 with 2-bromoacetamide

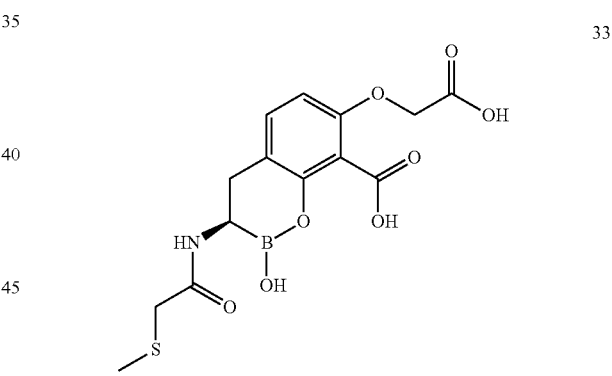

$^1$H NMR (400 MHz, CD$_3$OD) δ 10.07 (s, 1H), 7.00 (d, 1H), 6.40 (d, 1H), 4.68 (s, 2H), 3.23 (s, 2H), 3.12 (s, 1H), 2.86-2.76 (m, 2H), 1.82 (s, 3H).

MS calcd for (C$_{14}$H$_{16}$BNO$_8$S): 369.
MS (ESI, positive) found: (M+1): 370.
MS (ESI, negative) found: (M−1): 368.

Example 34: (R)-2,7-dihydroxy-3-(2-(methylthio)acetamido)-3,4-dihydro-2H-benzo[e][1,2]oxaborinine-8-carboxylic acid (34)

Compound 34 was prepared from intermediate 20H following hydrolysis procedure described in step 9 of example 20.

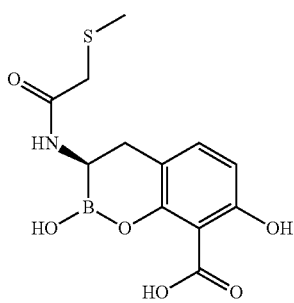

34

¹H NMR (400 MHz, CD₃OD) δ 10.44 (s, 1H), 7.16 (d, 1H), 6.48 (d, 1H), 2.91-2.79 (m, 2H), 1.78 (s, 3H).
MS calcd for ($C_{12}H_{14}BNO_6S$): 311.
MS (ESI, positive) found: (M+1): 312.
MS (ESI, negative) found: (M−1): 310.

Example 35: (R)-2-hydroxy-7-(4-methyl-4H-1,2,4-triazol-3-ylthio)-3-(2-(methylthio)acetamido)-3,4-dihydro-2H-benzo[e][1,2]oxaborinine-8-carboxylic acid (35)

Compound 35 was prepared following steps described for example 21 except replacing 5-amino-1,3,4-thiadiazole-2-thiol with 4-methyl-4H-1,2,4-triazole-3-thiol in step 2.

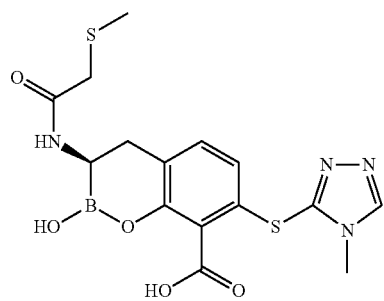

35

¹H NMR (400 MHz, CD₃OD) δ 8.73 (s, 1H), 7.09 (d, 1H), 6.28 (d, 1H), 3.62 (s, 3H), 3.20 (s, 2H), 2.89-2.82 (m, 3H), 1.81 (s, 3H).
MS calcd for ($C_{15}H_{17}BN_4O_5S_2$): 408.
MS (ESI, positive) found: (M+1): 409.
MS (ESI, negative) found: (M−1): 407.

Example 36: (R)-6,7-difluoro-2-hydroxy-3-(2-(methylthio)acetamido)-3,4-dihydro-2H-benzo[e][1,2]oxaborinine-8-carboxylic acid (36)

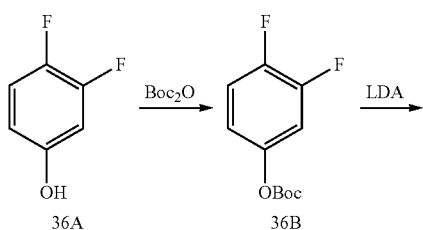

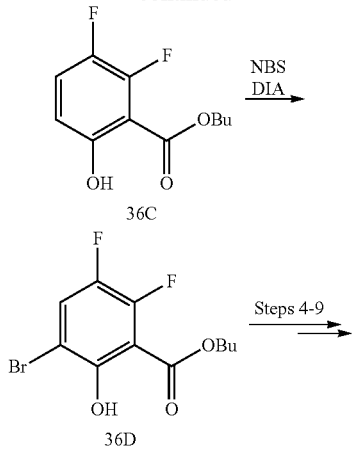

36C

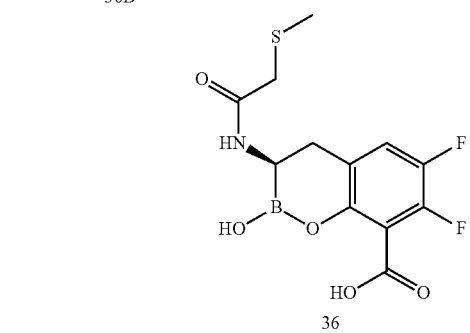

36D

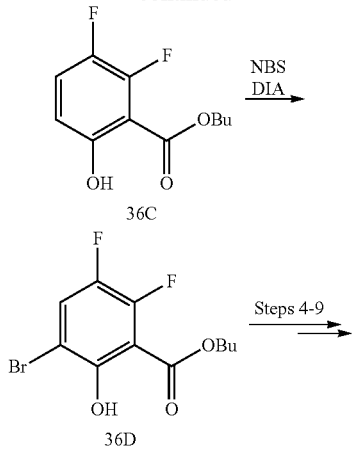

36

Step 1:
To a solution of compound 36A (4.8 g, 36.9 mmol) and Boc₂O (10.12 g, 48 mmol) in DCM (40 mL) was added DMAP (225 mg, 1.8 mmol). The resulting reaction mixture was stirred at room temperature for 16 hours before it was concentrated to dryness. The residue was purified by column chromatography (ethyl acetate/hexanes, v/v, 1/200~1/10 to afford compound 36B (9.03 g, 95%) as a white solid.

Step 2:
To a solution of compound 36B (500 mg, 2.17 mmol) in THF (15 mL) at −78° C. under N₂ was added dropwise freshly prepared LDA (2.39 mmol) in THF (10 mL). The mixture was stirred at −78° C. for 30 min, then warmed up to room temperature slowly. The reaction was then treated with 1 N HCl, extracted with ethylacetate, washed with brine and dried. The organic extract was concentrated to get 36C (480 mg, 95%), which was used directly in the next step without further purification.

Step 3:
To a solution of compound 36C (480 mg, 2.09 mmol) in DCM (20 mL) was added NBS (390 mg, 2.19 mmol) and DIA (42 mg, 0.42 mmol). The mixture was stirred at room temperature for 16 hours. The reaction was then concentrated, suspended in PE/EA solution (20/1, 20 mL), and stirred at rt for 3 h. The mixture was filtered and the filtrate was concentrated to dryness to get compound 36D (740 mg, 95%) as a white solid.

Steps 4-9:
Compound 36D was transformed to 36 in steps 4 to 9 following procedures described in steps 3-8 of example 1.

¹H NMR (400 MHz, CD₃OD) δ 10.25 (s, 1H), 7.05 (t, 1H), 3.30 (s, 2H), 3.18-3.15 (m, 2H), 2.75 (dd, 1H), 1.91 (s, 3H).

MS calcd for ($C_{12}H_{12}BF_2NO_5S$): 331.
MS (ESI, positive) found: (M+1): 332.
MS (ESI, negative) found: (M−1): 330.

Example 37: (3R)-5,6,7-trifluoro-2-hydroxy-3-[(2-methylsulfanylacetyl)amino]-3,4-dihydro-1,2-benzoxaborinine-8-carboxylic acid (37)

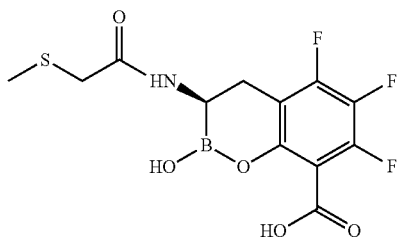

Compound 37 was prepared following the procedure described in Example 36 except replacing the starting material 3,4-difluorophenol with 3,4,5-trifluorophenol in step 1.

$^1$H NMR (400 MHz, $CD_3OD$) δ 3.30 (s, 2H), 3.18 (m, 2H), 2.61 (d, J=12 Hz, 1H), 1.96 (s, 3H).
MS calcd for ($C_{12}H_{11}BF_3NO_5S$): 349.
MS (ESI, positive) found: (M+1): 350.
MS (ESI, negative) found: (M−1): 348.

Example 38: 7-fluoro-2-hydroxy-3-[(2-methylsulfanylacetyl)amino]-3,4-dihydro-1,2-benzoxaborinine-8-carboxylic acid (38)

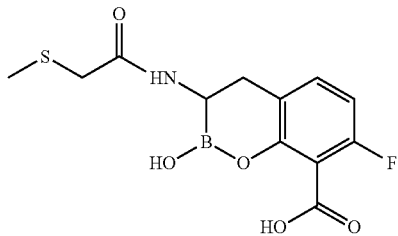

Compound 38 was prepared following the procedure described in Example 1 except replacing the compound 1E in step 4 with 2-(bromomethyl)-4,4,5,5-tetramethyl-1,3,2-dioxaborolane. Racemic mixture of 1G was made by transesterification of pinacol boronate derivative of 1G with (+)-pananediol. Racemic 1G was then converted to 38 as described in Example 1.

$^1$H NMR (400 MHz, $CD_3OD$) δ 7.12 (t, J=6.8 Hz, 1H), 6.61 (t, J=8.4 Hz, 1H), 3.30 (s, 2H), 3.29 (s, 1H), 3.24 (s, 2H), 1.83 (s, 3H).
MS calcd for ($C_{12}H_{13}BFNO_5S$): 313.
MS (ESI, positive) found: (M+1): 314.
MS (ESI, negative) found: (M−1): 312.

Example 39: (3R)-6-chloro-7-fluoro-2-hydroxy-3-[(2-methylsulfanylacetyl)amino]-3,4-dihydro-1,2-benzoxaborinine-8-carboxylic acid (39)

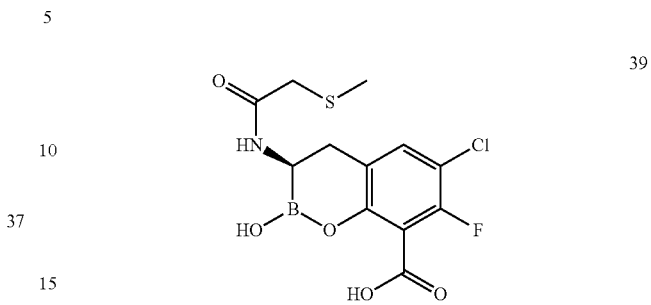

Compound 39 was prepared following the procedure described in Example 12 except replacing the starting material 2,6-dimethoxy benzoic acid with 5-bromo-3-chloro-2-fluoro-6-hydroxy-benzoic acid. 5-bromo-3-chloro-2-fluoro-6-hydroxy-benzoic acid was made from 1D by chlorination with sulfuryl chloride.

$^1$H NMR (300 MHz, $CD_3OD$) δ 7.18 (d, 1H), 3.26 (m, 2H), 3.12 (t, 1H), 2.83 (m, 2H), 1.89 (s, 3H).
MS calcd for ($C_{12}H_{12}BClFNO_5S$): 347.
MS (ESI, positive) found: (M+1): 348.
MS (ESI, negative) found: (M−1): 346.

Example 40: isopropoxycarbonyloxymethyl(3R)-2-hydroxy-7-methoxy-3-[(2-methylsulfanylacetyl)amino]-3,4-dihydro-1,2-benzoxaborinine-8-carboxylate (40)

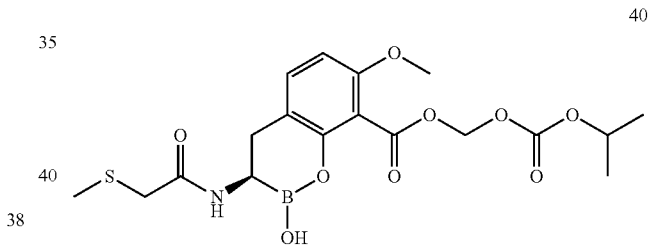

Compound 40 was prepared from compound 12 following the same procedure described in example 15.

$^1$H NMR (400 MHz, $CD_3OD$) δ 6.99 (d, J=7.6 Hz, 1H), 6.43 (d, J=8.4 Hz, 1H), 5.85 (m, 2H), 4.85 (m, 1H), 3.72 (s, 3H), 3.20 (d, J=3.9 Hz, 2H), 3.05 (s, 1H), 2.76 (m, 2H), 1.77 (s, 3H), 1.28 (d, J=6.0 Hz, 6H).
MS calcd for ($C_{18}H_{24}BNO_9S$): 441.
MS (ESI, negative) found: (M−1): 440.

Example 41: ethoxycarbonyloxymethyl(3R)-2-hydroxy-7-methoxy-3-[(2-methylsulfanylacetyl)amino]-3,4-dihydro-1,2-benzoxaborinine-8-carboxylate (41)

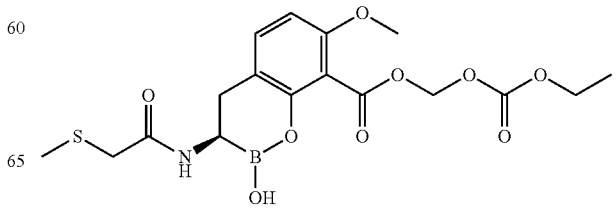

Compound 41 was prepared from compound 12 following the same procedure described in example 15 except for replacing the chloromethyl isopropyl carbonate with chloromethyl ethyl carbonate.

$^1$H NMR (300 MHz, CD$_3$OD) δ 7.05 (d, 1H), 6.43 (d, 1H), 5.85 (d, 2H), 4.21 (q, 2H), 3.65 (s, 3H), 3.21 (s, 2H), 3.05 (s, 1H), 2.78 (q, 2H), 1.79 (s, 3H), 1.25 (t, 3H).

MS calcd for (C$_{17}$H$_{22}$BNO$_9$S): 427.
MS (ESI, positive) found: (M+1): 428.
MS (ESI, negative) found: (M−1): 426.

Example 42: 2-methylpropanoyloxymethyl(3R)-2-hydroxy-7-methoxy-3-[(2-methylsulfanylacetyl)amino]-3,4-dihydro-1,2-benzoxaborinine-8-carboxylate (42)

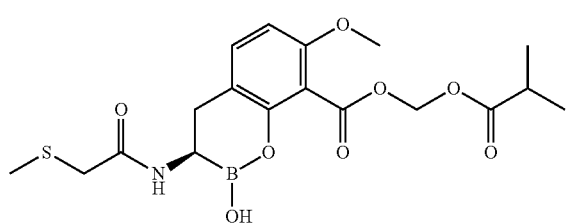

42

Compound 42 was prepared from compound 12 following the same procedure described in example 15 except for replacing the chloromethyl isopropyl carbonate with chloromethyl isobutyrate.

$^1$H NMR (400 MHz, CD$_3$OD) δ 6.97 (d, 1H), 6.42 (d, 1H), 5.85 (m, 2H), 3.76 (s, 3H), 3.19 (s, 2H), 3.08 (s, 1H), 2.79 (m, 2H), 2.61 (m, 1H), 1.77 (s, 3H), 1.18 (d, J=7.2 Hz, 6H).

MS calcd for (C$_{18}$H$_{24}$BNO$_8$S): 425.
MS (ESI, positive) found: (M+1): 426.
MS (ESI, negative) found: (M−1): 424.

Example 43: benzoyloxymethyl(3R)-7-fluoro-2-hydroxy-3-[(2-methylsulfanylacetyl)amino]-3,4-dihydro-1,2-benzoxaborinine-8-carboxylate (43)

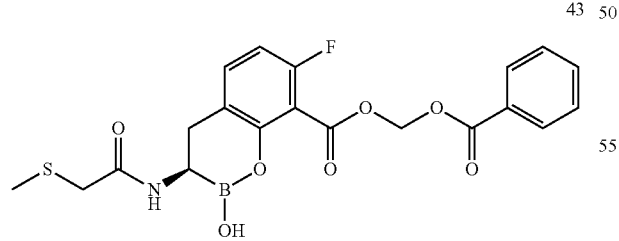

43

Compound 43 was prepared following the same procedure described in example 15 except for replacing the chloromethyl isopropyl carbonate with chloromethyl benzoate.

$^1$H NMR (300 MHz, CD$_3$OD) δ 8.10 (m, 2H), 7.64 (m, 1H), 7.50 (m, 2H), 7.08 (t, J=7.2 Hz, 1H), 6.56 (t, J=8.1 Hz, 1H), 6.18 (s, 2H), 3.15 (m, 3H), 2.82 (d, 2H), 1.78 (s, 3H).

MS calcd for (C$_{20}$H$_{19}$BFNO$_7$S): 447.
MS (ESI, negative) found: (M−1): 446.

Example 44: 2-methylpropanoyloxymethyl(3R)-2-hydroxy-7-methylsulfanyl-3-[(2-methylsulfanylacetyl)amino]-3,4-dihydro-1,2-benzoxaborinine-8-carboxylate (44)

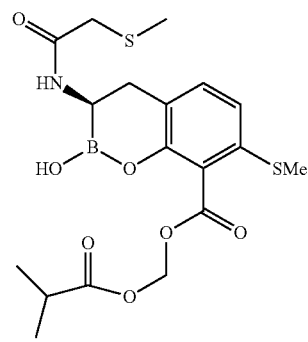

44

Compound 44 was prepared from compound 10 following the same procedure described in example 15 except for replacing the chloromethyl isopropyl carbonate with chloromethyl isobutyrate.

$^1$H NMR (300 MHz, CD$_3$OD) δ 7.06 (d, 1H), 6.86 (d, 1H), 5.92 (m, 2H), 3.21 (m, 2H), 3.12 (t, 1H), 2.84 (m, 2H), 2.63 (m, 1H), 2.37 (s, 3H), 1.77 (s, 3H), 1.20 (d, J=6.9 Hz, 6H).

MS calcd for (C$_{18}$H$_{24}$BNO$_7$S$_2$): 441.
MS (ESI, negative) found: (M−1): 440.

Example 45: 2-methylpropanoyloxymethyl(3R)-6,7-difluoro-2-hydroxy-3-[(2-methylsulfanylacetyl)amino]-3,4-dihydro-1,2-benzoxaborinine-8-carboxylate (45)

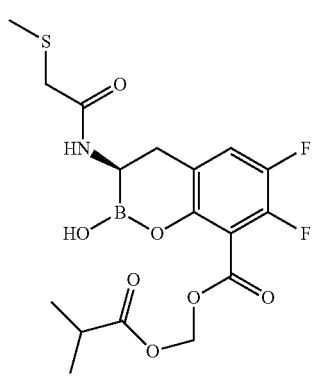

45

Compound 45 was prepared from compound 36 following the same procedure described in example 15 except for replacing the chloromethyl isopropyl carbonate with chloromethyl isobutyrate.

$^1$H NMR (300 MHz, CD$_3$OD) δ 7.15 (t, 1H), 5.95 (s, 2H), 3.21 (s, 2H), 3.12 (t, 1H), 2.81 (m, 2H), 2.65 (m, 1H), 1.88 (s, 3H), 1.20 (d, J=7.2 Hz, 6H).

MS calcd for ($C_{17}H_{20}BF_2NO_7S$): 431.
MS (ESI, negative) found: (M−1): 430.

Example 46: 2-methylpropanoyloxymethyl(3R)-6-chloro-7-fluoro-2-hydroxy-3-[(2-methylsulfanylacetyl)amino]-3,4-dihydro-1,2-benzoxaborinine-8-carboxylate (46)

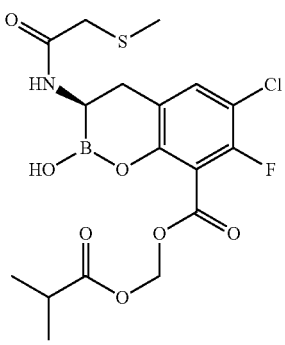

Compound 46 was prepared from compound 39 following the same procedure described in example 15 except for replacing the chloromethyl isopropyl carbonate with chloromethyl isobutyrate.

$^1$H NMR (300 MHz, $CD_3OD$) δ 7.20 (d, 1H), 5.93 (s, 2H), 3.21 (s, 2H), 3.12 (t, 1H), 2.82 (m, 2H), 2.65 (m, 1H), 1.87 (s, 3H), 1.20 (d, 6H).

MS calcd for ($C_{17}H_{20}BClFNO_7S$): 447.
MS (ESI, negative) found: (M−1): 446.

Example 47: Potentiation of Aztreonam

The potency and spectrum of β-lactamase inhibitors (BLIs) was determined by assessing their aztreonam potentiation activity in a dose titration potentiation assay using strains of various bacteria that are resistant to aztreonam due to expression of various β-lactamases. Aztreonam is a monobactam antibiotic and is hydrolyzed by the majority of beta-lactamases that belong to class A or C (but not class B or D). The potentiation effect was observed as the ability of BLI compounds to inhibit growth in the presence of sub-inhibitory concentration of aztreonam. MICs of test strains varied from 64 μg/mL to >128 μg/mL. Aztreonam was present in the test medium at 4 μg/mL. Compounds were tested at concentrations up to 40 μg/mL. In this assay potency of compounds was reported as the minimum concentration of BLI required to inhibit growth of bacteria in the presence of 4 μg/mL of aztreonam ($MPC_{@4}$). Table 1B summarizes the BLI potency of aztreonam potentiation ($MPC_{@4}$) for various strains overexpressing class A (ESBL and KPC), and class C beta-lactamases. Aztreonam MIC for each strain is also shown. In some cases the results were compared to comparative un-substituted compounds A, B, C, D, E, F, G, H shown below in Table 1A.

TABLE 1A

Comparative Compounds A, B, C, D, E, F, G, H, and I and their corresponding compounds of formula (Ia) with $R^4$ substitution.

| Comparative compound structure | $R^4$ substituted variants |
|---|---|
| A | Compounds 1, 10, 11, 12, 20, 21, 22, 23, 24, 31, 32, 33, 34, 35, 36 |
| B | Compounds 2 and 26 |
| C | Compounds 3 and 25 |
| D | Compound 4 |
| E | Compounds 5 and 27 |
| F | Compound 6 |

TABLE 1A-continued

Comparative Compounds A, B, C, D, E, F, G, H, and I and their corresponding compounds of formula (Ia) with R⁴ substitution.

| Comparative compound structure | R⁴ substituted variants |
|---|---|
| 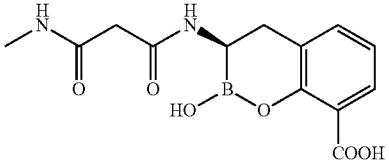 [SMILES: CNC(=O)CC(=O)N[C@H]1Cc2cccc(C(=O)O)c2OB1O] | Compound 7 |
| G 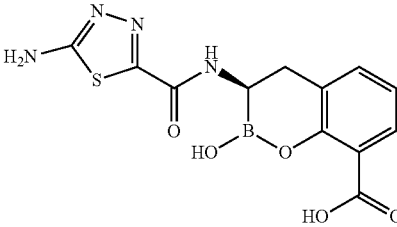 | Compounds 8, 9 and 28 |
| H 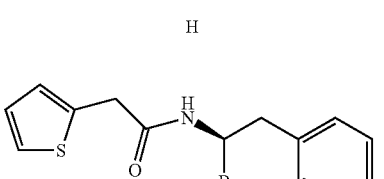 | Compounds 29 and 30 |

I

TABLE 1B

Activity of BLIs to potentiate aztreonam against strains expressing class A and class C enzymes.

| MIC (μg/mL) | AZT MPC4 CTX-M-14 KP1005 | AZT MPC4 CTX-M-15 KP1009 | AZT MPC4 SHV-5 ec308 | AZT MPC4 SHV-12 KP1010 | AZT MPC4 TEM-10 ec302 | AZT MPC4 KPC-2 KP1004 | AZT MPC4 ECL1002 | AZT MPC4 CMY-6 EC1010 |
|---|---|---|---|---|---|---|---|---|
| Aztreonam | Z | Z | Z | Z | Z | Z | Z | Z |
| A | X | X | X | X | Y | X | X | X |
| 1 | X | X | X | X | Y | X | Y | X |
| 10 | X | X | X | X | Y | X | Y | Y |
| 11 | X | X | X | X | Y | Y | Y | Y |
| 12 | X | X | X | X | X | X | X | X |
| 20 | X | Y | X | X | Y | Y | Y | Y |
| 21 | Y | Y | X | X | Y | Y | Y | Y |
| 22 | X | X | X | X | Y | Y | Y | Y |
| 23 | X | Y | X | X | Y | Y | Y | Y |
| 24 | Y | Y | X | X | Y | Y | Y | Y |
| 31 | Y | Y | X | X | Y | Y | Y | Y |
| 32 | Y | Y | Y | X | Y | Y | Y | Y |
| 33 | Y | Y | X | X | Y | Y | Y | Y |
| 34 | X | Y | X | X | Y | Y | Y | Y |
| 35 | Y | Y | X | X | Y | Y | Y | Y |
| 36 | X | X | X | X | Y | Y | Y | Y |
| B | X | X | X | X | Y | X | X | X |
| 2 | X | X | X | X | Y | X | Y | Y |
| 26 | X | X | X | X | Y | X | Y | Y |
| C | X | X | X | X | Y | X | Y | X |
| 3 | Y | X | X | X | X | Y | Y | Y |
| 25 | X | X | X | X | X | X | Y | Y |
| D | Y | Y | Y | Y | Z | Y | Y | X |
| 4 | Y | X | X | X | Y | Y | Y | Y |
| E | X | X | X | X | Y | X | X | X |
| 5 | X | X | X | X | Y | X | Y | Y |
| 27 | X | X | X | X | Y | X | Y | Y |
| F | Y | Y | Y | Y | Z | X | Y | Y |
| 6 | Y | Y | Y | X | Y | X | Y | Y |
| G | Y | X | X | X | Y | X | X | Y |
| 7 | X | X | X | X | Y | X | Y | Y |
| H | Y | X | X | X | X | Y | X | X |
| 8 | Y | Y | X | X | Y | Y | Y | Y |
| 9 | Y | Y | X | X | Y | Y | Y | Y |
| 28 | Y | Y | X | X | Y | Y | Y | X |
| I | X | Y | X | X | Y | Y | X | Y |

TABLE 1B-continued

Activity of BLIs to potentiate aztreonam against strains expressing class A and class C enzymes.

| MIC (µg/mL) | AZT MPC4 CTX-M-14 KP1005 | AZT MPC4 CTX-M-15 KP1009 | AZT MPC4 SHV-5 ec308 | AZT MPC4 SHV-12 KP1010 | AZT MPC4 TEM-10 ec302 | AZT MPC4 KPC-2 KP1004 | AZT MPC4 ECL1002 | AZT MPC4 CMY-6 EC1010 |
|---|---|---|---|---|---|---|---|---|
| 29 | X | X | X | X | X | Y | X | X |
| 30 | X | X | X | X | Y | X | Y | Y |

X = MIC of less than 1 ng/mL
Y = MIC of 1 µg/mL to 10 µg/mL
Z = MIC of greater than 10 µg/mL

Example 48: Potentiation of Tigemonam

Selected β-lactamase inhibitors were also tested for their ability to potentiate the monobactam tigemonam. The potentiation effect was observed as the ability of BLI compounds to inhibit growth in the presence of sub-inhibitory concentration of tigemonam. MICs of test strains varied from 16 µg/mL to >64 µg/mL. Tigemonam was present in the test medium at 4 µg/mL. Compounds were tested at concentrations up to 40 µg/mL. In this assay potency of compounds was reported as the minimum concentration of BLI required to inhibit growth of bacteria in the presence of 4 µg/mL of aztreonam ($MPC_{@4}$). Table 2 summarizes the BLI potency of tigemonam potentiation ($MPC_{@4}$) for various strains overexpressing class A (ESBL) and class C beta-lactamases. Tigemonam MIC for each strain is also shown. In some cases the results were compared to comparative un-substituted compounds A, B, C, D, E, F, G, H, I as shown in Table 1A.

TABLE 2

Activity of BLIs to potentiate tigemonam against strains expressing class A and class C enzymes.

| MIC (µg/mL) | TIG MPC$_4$ CTX-M-14 KP1005 | TIG MPC$_4$ CTX-M-15 KP1009 | TIG MPC$_4$ SHV-5 ec308 | TIG MPC$_4$ SHV-12 KP1010 | TIG MPC$_4$ TEM-10 ec302 | TIG MPC4 ECL1002 | TIG MPC4 CMY-6 EC1010 |
|---|---|---|---|---|---|---|---|
| Tigemonam | Z | Z | Z | Z | Z | Z | Z |
| A | Y | X | X | X | Y | X | X |
| 1 | X | X | X | X | Y | X | X |
| 10 | Y | X | X | X | Y | X | X |
| 11 | X | Y | X | X | Z | X | X |
| 12 | X | X | X | X | Y | X | X |
| 20 | Y | X | X | X | Z | X | X |
| 21 | Y | Y | X | X | Y | Y | Y |
| 22 | X | X | X | X | Y | Y | X |
| 23 | X | Y | X | X | Y | X | Y |
| 24 | Y | Y | Y | X | Z | Y | Y |
| 31 | Y | Y | X | X | Z | X | Y |
| 32 | Y | Y | Y | X | Z | Y | Y |
| 33 | Y | Y | Y | X | Z | Y | Y |
| 34 | X | Y | X | X | Y | X | X |
| 35 | Y | Y | X | X | Y | Y | Y |
| 36 | X | X | X | X | Y | X | X |
| B | Y | X | Y | X | Z | X | X |
| 2 | X | X | X | X | Y | X | X |
| 26 | X | X | X | X | Y | X | X |
| C | X | X | X | X | Y | Y | X |
| 3 | X | X | X | X | Y | Y | X |
| 25 | X | X | X | X | Y | X | X |
| D | Z | Y | Y | Y | Z | X | X |
| 4 | Y | X | Y | Y | Z | X | X |
| E | Y | Y | Y | X | Z | X | X |
| 5 | Y | X | X | X | Z | X | X |
| 27 | Y | X | X | X | Z | X | X |
| F | Y | Y | Y | Y | Z | X | X |
| 6 | Y | Y | Y | Y | Z | X | X |
| G | Y | Y | Y | X | Z | X | X |
| 7 | Y | X | X | X | Z | X | X |
| H | Y | X | X | X | Y | X | X |
| 8 | Y | X | X | X | Y | Y | X |
| 9 | Y | Y | X | X | Z | X | X |
| 28 | Y | Y | X | X | Y | Y | X |
| I | Y | Y | X | X | Z | X | X |

TABLE 2-continued

Activity of BLIs to potentiate tigemonam against strains expressing class A and class C enzymes.

| MIC (μg/mL) | TIG MPC$_4$ CTX-M-14 KP1005 | TIG MPC$_4$ CTX-M-15 KP1009 | TIG MPC$_4$ SHV-5 ec308 | TIG MPC$_4$ SHV-12 KP1010 | TIG MPC$_4$ TEM-10 ec302 | TIG MPC4 ECL1002 | TIG MPC4 CMY-6 EC1010 |
|---|---|---|---|---|---|---|---|
| 29 | X | X | X | X | Y | X | X |
| 30 | Y | X | X | X | Y | X | X |

X = MIC of less than 1 μg/mL
Y = MIC of 1 μg/mL to 10 μg/mL
Z = MIC of greater than 10 μg/mL

Example 49: Potentiation of Biapenem

β-lactamase inhibitors were also tested for their ability to potentiate the carbapenem biapenem against strains producing class A (KPC) and class D (OXA-48) carbapenemases. The potentiation effect was observed as the ability of BLI compounds to inhibit growth in the presence of a sub-inhibitory concentration of biapenem. Biapenem MIC of test strains were 16-32 μg/mL. Biapenem was present in the test medium at 1 μg/mL. Compounds were tested at concentrations up to 40 μg/mL. In this assay potency of compounds was reported as the minimum concentration of BLI required to inhibit growth of bacteria in the presence of 1 μg/mL of biapenem (MPC$_1$). Table 3 summarizes the BLI potency of biapenem potentiation (MPC$_{@1}$) for two strains overexpressing class A (KPC) and class D (OXA-48) carbapenemases. Biapenem MIC for each strain is also shown.

TABLE 3

Activity of BLIs to potentiate biapenem against strains expressing class A (KPC) or class D (OXA-48) carbapenemases.

| MIC (μg/mL) | BPM MPC$_1$ KP1004 KPC-2 | BPM MPC$_1$ OXA-48 KP1086 |
|---|---|---|
| Biapenem | Z | Z |
| A | X | Y |
| 1 | X | Y |
| 10 | X | Z |
| 11 | X | Y |
| 12 | X | Y |
| 20 | X | Z |
| 21 | Y | Z |
| 22 | X | Z |
| 23 | X | Z |
| 24 | X | Z |
| 31 | X | Z |
| 32 | X | Y |
| 33 | X | Z |
| 34 | X | Y |
| 35 | X | Z |
| 36 | X | Y |
| B | X | Y |
| 2 | X | Y |
| 26 | X | Y |
| C | X | Y |
| 3 | X | Z |
| 25 | X | Z |
| D | X | Y |
| 4 | X | Z |
| E | X | Y |
| 5 | X | Y |
| 27 | X | Y |
| F | X | Y |
| 6 | X | Y |
| G | X | Y |
| 7 | X | Y |
| H | X | Y |
| 8 | X | Y |
| 9 | X | Z |
| 28 | Y | Z |
| I | X | Y |
| 29 | X | Y |
| 30 | X | Y |

X = MIC of less than 1 μg/mL
Y = MIC of 1 μg/mL to 10 μg/mL
Z = MIC of greater than 10 μg/mL

Example 50: Inhibitory Activity $K_i$ values of inhibition of purified class A, C and D enzymes were determined spectrophotometrically using nitrocefin as reporter substrate. Purified enzymes were mixed with various concentrations of inhibitors in reaction buffer and incubated for 10 min at room temperature. Nitrocefin was added and substrate cleavage profiles were recorded at 490 nm every 10 sec for 10 min. The results of these experiments are presented in Table 4. These experiments confirmed that the described compounds are inhibitors with a broad-spectrum of activity towards various β-lactamases. In some cases the results were compared to comparative un-substituted compounds A, B, C, D, E, F, G, H, and I as shown in Table 1A.

TABLE 4

Activity of BLIs (Ki, uM) to inhibit cleavage of nitrocefin by purified class A, C and D enzymes

| | Ki (CTX-M-14, NCF), uM | Ki (SHV-12, NCF), uM | Ki (TEM-10, NCF), uM | Ki (KPC-2, NCF), uM | Ki (P99, NCF), uM | Ki (Pa AmpC, NCF), uM | Ki (OXA-48, NCF), uM |
|---|---|---|---|---|---|---|---|
| A | X | Y | Y | Z | Y | Y | X |
| 1 | X | X | X | Z | Z | ND | Z |
| 10 | X | X | X | Z | Z | ND | Y |
| 11 | Y | Y | Y | Z | Z | Z | Y |
| 12 | X | X | X | Z | Z | Z | X |
| 20 | X | X | Y | Z | Z | Z | X |
| 21 | X | X | X | Z | Z | Z | X |
| 22 | X | X | X | Z | Z | Z | ND |
| 23 | X | X | X | Z | Z | Z | X |
| 24 | X | Y | Y | Z | Z | Z | X |
| 31 | Y | X | Y | Z | Z | Z | Y |
| 32 | Y | X | Y | Z | Z | Z | Y |
| 33 | X | X | X | Z | Z | Z | X |
| 34 | X | X | X | Z | Y | Z | X |
| 35 | X | X | Y | Z | Z | Z | X |
| 36 | X | X | X | Z | Z | Z | X |
| B | Y | X | Y | Z | Y | Y | Y |
| 2 | X | X | Z | Z | Z | Z | Z |
| 26 | X | X | Y | Z | Z | Z | Y |
| C | Y | X | Y | Z | Y | X | X |
| 3 | X | X | Y | Z | Z | Z | Y |
| 25 | X | X | X | Y | Y | Z | X |
| D | X | Y | Z | Z | Z | Z | X |
| 4 | X | X | Y | Z | Z | Z | X |
| E | X | X | Y | Z | Y | ND | X |
| 5 | X | X | Y | Z | Z | Z | X |
| 27 | X | X | Y | Z | Z | Z | X |
| F | Y | Y | Y | Y | Y | ND | X |
| 6 | X | X | Y | Z | Z | Z | Y |
| G | X | X | Y | Z | Y | ND | X |
| 7 | X | X | Y | Z | Z | Z | Y |
| H | Y | X | Y | Z | Y | X | Y |
| 8 | X | X | X | Z | Z | Z | X |
| 9 | Y | X | Y | Z | Z | Z | Z |
| 28 | X | X | Y | Z | Y | Y | X |
| I | X | X | Y | Z | Y | ND | X |
| 29 | X | X | X | Y | Y | Y | X |
| 30 | X | X | X | Y | Y | Y | X |

X = Less than 0.001 μM
Y = 0.001 μM to 0.01 μM
Z = Greater than 0.01 μM
ND = not determined

Example 51: MexAB-OprM Dependent Efflux of BLIs

Efflux of BLIs from *Pseudomonas aeruginosa* by the MexAB-OprM efflux pump was also evaluated. The plasmid expressing the gene encoding KPC-2 was introduced into two strains of *P. aeruginosa*, PAM1032 and PAM1154 that overexpressed or lacked MexAB-OprM, respectively. Due to expression of KPC-2 both strains became resistant to biapenem. Biapenem is not affected by efflux in *P. aeruginosa* and both strains had the same biapenem MIC of 32 μg/ml. Potency of BLIs to potentiate biapenem in these strains was determined. Potency was defined as the ability of BLI to decrease MIC of biapenem 64-fold, from 32 μg/ml to 0.5 μg/ml, or $MPC_{64}$. The ratio of $MPC_{64}$ values for each BLI in PAM1032/KPC-2 (efflux proficient) and PAM1154/KPC-2 (efflux deficient) was determined to generate the Efflux Index (EI). In some cases the results were compared to comparative un-substituted compounds A, B, C, D, E, F, G, H, I as shown in Table 1A. Table 5 shows $MPC_{64}$ and EIs values for selected BLIs.

TABLE 5

MexAB-OprM Dependent Efflux of BLIs from *P. aeruginosa*

| | PAM1032/ KPC-2 Biapenem MPC64 | PAM1154/ KPC-2 Biapenem MPC64 | EI |
|---|---|---|---|
| A | 80 | 5 | 8 |
| 1 | 20 | 5 | 4 |
| 10 | >40 | 20 | >2 |
| 11 | 20 | 10 | 2 |
| 12 | 10 | 5 | 2 |
| 20 | >40 | 20 | >2 |
| 21 | ND | ND | ND |
| 22 | 40 | 20 | 2 |
| 23 | 40 | 20 | 2 |
| 24 | 40 | 10 | 4 |
| 31 | >40 | 40 | >1 |
| 32 | 40 | 20 | 2 |
| 33 | >40 | >40 | ND |
| 34 | 40 | 2.5 | 16 |
| 35 | 40 | 20 | 2 |
| 36 | 40 | 10 | 4 |

TABLE 5-continued

MexAB-OprM Dependent Efflux of BLIs from *P. aeruginosa*

| | PAM1032/<br>KPC-2<br>Biapenem<br>MPC64 | PAM1154/<br>KPC-2<br>Biapenem<br>MPC64 | EI |
|---|---|---|---|
| B | 2.5 | 2.5 | 1 |
| 2 | 5 | 5 | 1 |
| 26 | 5 | 5 | 1 |
| C | 80 | 5 | 16 |
| 3 | >40 | 40 | >1 |
| 25 | 40 | 20 | 2 |
| D | >40 | 10 | >4 |
| 4 | 10 | 10 | 1 |
| E | 80 | 20 | 4 |
| 5 | 10 | 10 | 1 |
| 27 | 10 | 10 | 1 |
| F | 5 | 1.25 | 4 |
| 6 | 5 | 2.5 | 2 |
| G | 40 | 5 | 8 |
| 7 | 20 | 10 | 2 |
| H | 80 | 2.5 | 32 |
| 8 | 40 | 10 | 4 |
| 9 | 40 | 20 | 2 |
| 28 | 40 | 20 | 2 |
| I | 80 | 2.5 | 32 |
| 29 | 40 | 5 | 8 |
| 30 | 40 | 10 | 4 |

In all cases, substitutions at the $R^4$ position resulted in compounds that were less susceptible to efflux in *P. aeruginosa* as compared to un-substituted analogs.

Example 52: Serum Stability of Prodrugs

Prodrug strategy is one of the ways to achieve or increase oral bioavailability for therapeutic drugs. Compounds 1, 10, 12, 36 and 39 were used as templates for various ester prodrugs. After a prodrug molecule is absorbed into systemic circulation, it should be hydrolyzed in the blood in order to release the active form. Hydrolysis of several prodrugs by rat and human serum were evaluated.

For all stability experiments the test compounds were treated with rat or human serum in Eppendorf tubes. Typically, 992 μl of serum was prewarmed at 37 degrees for 2 minutes and then 8 μl of a compound (at 5 mg/ml, 125×) was added to it to get a final concentration of 40 μg/ml and immediately mixed. Alternatively, serum stability might be tested at 1 mg/ml. The tube was placed back in a 37 degree water bath and 100 μl-samples were taken at designated times and transferred directly into Eppendorf tubes containing 400 μl of precipitant solution (a 4.00 μg/mL solution of a standard compound, RPX7015, in 10% water, 45% methanol and 45% acetonitrile). After vortexing for 30 seconds, the tube was centrifuged in a microcentrifuge for 10 minutes at 15K rpm. Next, 100 μl of the supernatant was combined with 600 μl of water and injected on LC-MS using 0.1% formic acid in water for mobile phase A and 0.1% formic acid in methanol for mobile phase B on an ACE 5 C18 2.1×100 mm column with a 10 μL injection. The flow rate and gradient were adjusted as needed to give the desired resolution and run time. The pH of the mobile phase was adjusted if needed to improve the chromatography.

The time course of both the disappearance of a prodrug and the appearance of the active form of that prodrug is presented in Table 6 and Table 7. The active metabolites for all of the listed prodrugs are corresponding parent drugs

TABLE 6

Time-course of prodrug hydrolysis by human serum

| Compound | Theoretical Initial Conc. in Serum (ug/mL) | Measured Initial Conc. in Serum (ug/mL) | Conc. at t = 1 hr (ug/mL) | Conc. at t = 3 hr (ug/mL) | Active Metabolite Initial Conc. in Serum (ug/mL) | Active Metabolite Conc. at t = 1 hr (ug/mL) | Active Metabolite Conc. at t = 3 hr (ug/mL) |
|---|---|---|---|---|---|---|---|
| 13 | 40 | 30.6 | 1.56<br>(t = 2 h) | BQL<br>(t = 4 h) | 9.2 | 29.3<br>(t = 2 h) | 30.4<br>(t = 4 h) |
| 14 | 40 | 36.8 | 5.00<br>(t = 2 h) | 1.13<br>(t = 4 h) | ND | ND | ND |
| 15 | 40 | 33.2 | 12.8<br>(t = 2 h) | 5.32<br>(t = 4 h) | ND | ND | ND |
| 16 | 20 | 20.7 | 2.29 | 0.27 | 5.60 | 12.1 | 13.4 |
| 17 | 20 | 9.74 | 1.18 | 0.16 | 2.96 | 14.0 | 16.2 |
| 18 | 20 | 16.3 | 11.6 | 6.27 | 0.278 | 1.53 | 3.13 |
| 19 | 20 | 20.3 | 6.11 | 1.17 | 1.87 | 9.43 | 13.2 |
| 40 | 20 | 24.8 | 23.6 | 19 | 0.45 | 0.5 | 0.63 |
| 41 | 20 | 24.4 | 20.80 | 20.9 | 0.55 | 0.95 | 1.58 |
| 42 | 20 | 23.4 | 19.5 | 16.5 | 0.93 | 1.74 | 3.14 |
| 43 | 20 | 18.9 | 8.94 | 3.16 | 0.42 | 6.26 | 10.1 |
| 44 | 20 | 18.6 | 18.1 | 12.5 | 0.25 | 1.22 | 2.55 |
| 45 | 20 | 18.4 | 4.83 | 0.58 | 0.43 | 7.75 | 9.18 |
| 46 | 20 | 19.1 | 6.22 | 1.01 | 0.45 | 5.09 | 6.16 |

TABLE 7

The Time-course of hydrolysis of prodrugs by rat serum

| Compound | Theoretical Initial Conc. in Serum (ug/mL) | Measured Initial Conc. in Serum (ug/mL) | Conc. at t = 1 hr (ug/mL) | Conc. at t = 3 hr (ug/mL) | Active Metabolite Initial Conc. in Serum (ug/mL) | Active Metabolite Conc. at t = 1 hr (ug/mL) | Active Metabolite Conc. at t = 3 hr (ug/mL) |
|---|---|---|---|---|---|---|---|
| 13 | 40 | 28.1 | 9.81 (t = 2 h) | BQL (t = 4 h) | 8.9 | 27.6 (t = 2 h) | 35.1 (t = 4 h) |
| 14 | 40 | 39.6 | BQL (t = 2 h) | BQL (t = 4 h) | ND | ND | ND |
| 15 | 40 | 30.6 | BQL (t = 2 h) | BQL (t = 4 h) | ND | ND | ND |
| 16 | 20 | 20.2 | 0.40 | 0 | 3.59 | 14.4 | 13.9 |
| 17 | 20 | 9.22 | 1.35 | | 1.82 | 15.0 | 16.5 |
| 18 | 20 | 14.6 | 9.39 | 3.29 | 0.28 | 4.31 | 9.75 |
| 19 | 20 | 17.4 | 0 | 0 | 2.96 | 15.7 | 15.1 |
| 40 | 20 | 25.9 | 2.71 | 0.74 | 1.11 | 10.1 | 11.7 |
| 41 | 20 | 20.6 | 0.40 | 0 | 1.23 | 7.17 | 7.00 |
| 42 | 20 | 24.2 | 14.1 | 5.58 | 1.23 | 4.58 | 8.76 |
| 43 | 20 | 18.0 | 11.7 | 4.58 | 0.65 | 5.62 | 9.49 |
| 44 | 20 | 18.4 | 16.0 | 5.21 | 0.44 | 3.28 | 6.99 |
| 45 | 20 | 18.6 | 8.85 | 0.42 | 0.68 | 8.04 | 10.4 |
| 46 | 20 | 18.7 | 8.29 | 0.41 | 0.81 | 7.29 | 9.35 |

BQL signifies below the quantifiable limit for this assay.
ND means not determined The data showed that different prodrugs differ significantly in serum stability. Compound 13 appeared to be completely converted to active metabolite over the course of 4 hour experiment.

Example 53: Comparison of Intravenous Pharmacokinetics of Selected Compounds Compounds 1, 2, 3, 29, and 30 and the comparative compounds A, B, C, and I were tested for their intravenous pharmacokinetics. Rats (n=3 per compound) were administered by a single infusion. Intravenous doses were infused over 0.5 hours via an indwelling femoral vein cannula. Plasma (~0.3 mL) samples were collected from each rat at designated time points up to 24 hours. Blood samples were centrifuged within 5 min of collection at 12000 g for 5 min to obtain plasma. The plasma samples were stored at −80° C. until analyzed. Data were analyzed using WinNonlin. The doses of all compounds tested were 20 mg/kg.

TABLE 8

Free Cl (l/hr/kg) of Unsubstituted vs. Fluorine-substituted Compounds

| Unsubstituted Compound | Free Cl (l/hr/kg) | $R^4$-substituted compound | Free Cl (l/hr/kg) |
|---|---|---|---|
| A | 2.47 | 1 | 0.85 |
| B | 0.57 | 2 | 0.61 |
| C | 2.45 | 3 | 0.78 |
| I | 8.17 | 29 | 0.67 |
| I | 8.17 | 30 | 1.38 |

As shown in Table 8, substitutions at the $R^4$ position provided compounds with approximately the same or better or intravenous pharmacokinetics than the corresponding unsubstituted compounds with $R^4$ being hydrogen.

Example 54: Oral Pharmacokinetics of Prodrugs of Compounds 1 and 12

The prodrugs of compound 1, including compounds 13, 14, 15, 16, 17, 19 and prodrugs of compound 12 including compounds 40, 41, 42 were tested for their oral pharmacokinetics. Rats (n=3 per compound) were administered a single oral dose. Oral doses were administered as a bolus. Plasma (~0.3 mL) samples were collected from each rat at designated time points up to 24 hours. Blood samples were centrifuged within 5 min of collection at 12000 g for 5 min to obtain plasma. The plasma samples were stored at −80° C. until analyzed. Data were analyzed using WinNonlin and the results are presented in Table 9.

TABLE 9

Bioavailability of Pro-Drugs of Compound 1 and 12

| $R^4$-substituted compound | Dose of Compound 1 or 12 from Prodrug (mg/kg) | Range of % Oral Bioavailability (Average) |
|---|---|---|
| 13 | 30 | 40-44 (41.7) |
| 14 | 53 | 30-31 (30.3) |
| 15 | 52 | 67-73 (69.5) |
| 16 | 50 | 47-57 (51.6) |
| 17 | 51 | 41-82 (67.2) |
| 19 | 52 | 65-87 (73.4) |
| 40 | 30 | 16-37(17.3) |
| 41 | 30 | 14-22(16.7) |
| 42 | 30 | 25-30(28.1) |

Example 55: Comparison of Monomer Content of Selected Compounds

Boronic acid containing compounds are known to undergo oligomerization. The presence of oligomers can greatly complicate drug development, as they represent new chemical species whose content must be controlled and qualified by testing in toxoicology studies. The monomer content of compounds was evaluated by adjusting aqueous solutions to physiological pH at various concentrations. The monomer content of pH adjusted solutions was measured using LC-UV.

Test compounds were weighed out into a 1.5 mL Eppendorf tube. A solution of water was prepared in 1.00 mg/mL, 10.0 mg/mL or 100 mg/mL concentrations of the compound based on active fraction. A volume 20 uL was subtracted to allow room for addition of acid or base to adjust pH. The solution pH was measured. The pH was then adjusted through addition of acid or base as necessary until the reading was in the 7.6 to 8 range. A final pH measurement was made after ensuring all the compound was in solution. The solution was injected onto LC-UV in 0.1 uL to 5 uL volume within less than half an hour after the time the sample was prepared. Elution was done using 0.1% TFA in water for mobile phase A and 0.085% TFA in methanol for mobile phase B on an Excel ACE 5 Super C18 2.1×100 mm column at 0.6 ml/min flow rate with 9 min gradient, 3.9 minute hold at 90% B and 18 minute run time. The absorption was measured at 220, 254 and 300 nm with a 4 nm bandwidth.

As shown in Table 10, compounds with substitution at $R^4$ position had the higher monomer content and reduced tendency to undergo Oligomerization, while the comparative compounds without $R^4$ substitution readily underwent oligomerization at physiological pH and had low monomer content. The monomer content of $R^4$ substituted compounds remained less or unaffected even at high concentrations.

TABLE 10

Monomer content and measured pH at 1, 10 and 100 mg/mL concentration

| Compound | % Monomer in 1 mg/mL salt solution | pH of 1 mg/mL salt solution | % Monomer in 10 mg/mL salt solution | pH of 10 mg/mL salt solution | % Monomer in 100 mg/mL salt solution | pH of 100 mg/mL salt solution |
|---|---|---|---|---|---|---|
| Unsubstituted Compound A | 72.1 | 7.6 | 43.0 | 7.7 | 14.9 | 7.8 |
| 1 | 98.0 | 7.8 | 97.5 | 7.8 | 96.4 | 7.7 |
| 12 | 98.2 | 7.7 | 95.5 | 7.6 | 96.5 | 7.9 |
| 10 | 87.5 | 7.6 | ND | ND | ND | ND |
| 11 | 88.0 | 7.8 | ND | ND | ND | ND |
| 21 | 98.1 | 7.9 | ND | ND | ND | ND |
| 24 | 98.3 | 7.9 | ND | ND | ND | ND |
| 31 | 99.7 | 7.9 | ND | ND | ND | ND |
| 32 | 95.8 | 8.0 | ND | ND | ND | ND |
| Unsubstituted Compound I | 80.0 | 7.8 | 37.0 | 7.9 | 8.3 | 7.9 |
| 29 | 99.4 | 7.7 | 98.6 | 7.8 | 67.0 | 7.9 |
| 30 | 94.6 | 7.6 | 93.5 | 7.6 | 87.6 | 7.9 |
| 3 | 99.8 | 7.6 | ND | ND | ND | ND |
| 5 | 98.5 | 7.7 | ND | ND | ND | ND |
| 7 | 97.1 | 7.6 | ND | ND | ND | ND |

ND means not determined

What is claimed is:

1. A compound having the structure of Formula I or II:

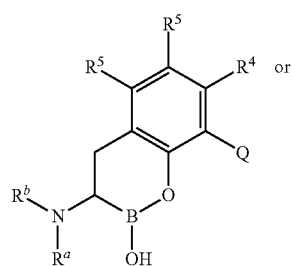

(I)

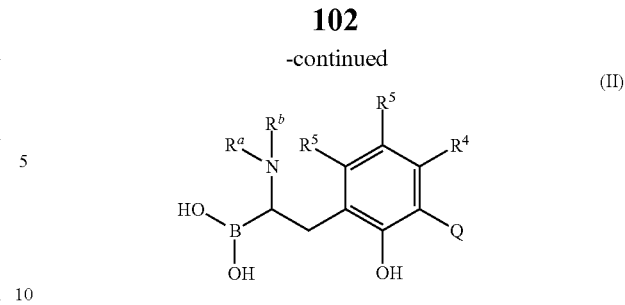

(II)

or pharmaceutically acceptable salts thereof, wherein:

$R^a$ is independently selected from the group consisting of hydrogen; $C_1$-$C_6$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_{3-7}$cycloalkyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; 5-10 membered heteroaryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 3-10 membered heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and $R^b$ is independently selected from the group consisting of hydrogen; —OH; —C(O)G; —C(O)OG; —S(O)$_2$G; —C(=NR$^1$R$^2$)G; —C(=NOR$^3$)G; $C_1$-$C_6$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; —O—$C_1$-$C_6$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; —S—$C_1$-$C_6$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido; and halogen; $C_3$-$C_8$ cycloalkyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$ aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; 5-10 membered heteroaryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 3-10 membered heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; or $R^a$ and $R^b$ together with the nitrogen to which they are attached form a 5-8 membered heterocyclic or heteroaryl ring, optionally comprising additional 1-3 heteroatoms selected from O, S or N;

G is selected from the group consisting of hydrogen; —N$R^1R^2$; —CH$_2$N$_3$; —CH$_2$CN; —C(O)N$R^1R^2$; —CH(=CH—$R^6$)$R^7$; —CH$_2$C(O)N$R^1R^2$; —CH$_2$S(O)$_2$ N$R^1R^2$; —(CH$_2$)$_n$—Y—Z; —O—(CH$_2$)$_n$—C(O)N$R^1R^2$; —S$R^3$; —P(O)$R^1R^2$; —CH$_2$N$R^1$C(O)$R^6$; —C(=NO$R^3$)—Z; —C(O)O$R^3$; —C(O)—Z; —S(O)$_2R^3$; —C(O)N$R^1$O$R^3$; —N$R^1$(O$R^3$); —N$R^1$C(O)$R^6$; —N$R^1$C(O)N$R^2R^{1a}$; —N$R^1$C(O)O$R^3$; —N$R^1$S(O)$_2R^3$; —N$R^1$S(O)$_2$N$R^2R^{1a}$; —N$R^1$N$R^2R^{1a}$; —C(O)N$R^1$N$R^2R^{1a}$; —S(O)$_2$N$R^1$N$R^2R^{1a}$; —C(=N$R^1$)$R^6$; —C(=N$R^1$)N$R^2R^{1a}$; —N$R^1$C$R^6$(=N$R^2$); —N$R^1$C(=N$R^2$)N$R^{1a}R^{2a}$; $C_1$-$C_{10}$ alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_2$-$C_{10}$alkenyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_2$-$C_{10}$alkynyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_3$-$C_7$ carbocyclyl optionally substituted with one or more substituents selected from the group consisting of $C_1$-$C_6$alkyl, —O—$C_1$-$C_6$alkyl, —S—$C_1$-$C_6$alkyl amino, =C(O)-amino, =S(O)$_2$-amino, hydroxy, cyano, azido, and halogen; 5-10-membered heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 5-10 membered heteroaryl optionally substituted with one or more substituents selected from the group consisting of $C_1$-$C_6$alkyl, $C_6$-$C_{10}$aryl, 5-10 membered heteroaryl, —O—$C_1$-$C_6$alkyl, —S—$C_1$-$C_6$alkyl, amino, —C(O)-amino, —S(O)$_2$-amino, hydroxy, cyano, azido, and halogen;

n is 0 to 3;

Y is selected from a group consisting of —S—, —S(O)—, —S(O)$_2$—, —O—, —C(O)—, —C$R^6R^7$—, —O—C$R^6R^7$—, and —N$R^1$—;

Z is selected from the group consisting of hydrogen; CON$R^1R^2$; —COOH; $C_1$-$C_6$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, —COOH, and halogen; $C_2$-$C_{10}$ alkenyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, —COOH, and halogen; $C_2$-$C_{10}$ alkynyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, —COOH, and halogen; $C_3$-$C_7$ carbocyclyl optionally substituted with one or more substituents selected from the group consisting of $C_1$-$C_6$alkyl, —O—$C_1$-$C_6$alkyl, amino, —C(O)-amino, —S(O)$_2$-amino, hydroxy, cyano, azido, —COOH, and halogen; 3-10 membered heterocyclyl optionally substituted with one or more substituents selected from the group consisting of $C_1$-$C_6$alkyl, —O—$C_1$-$C_6$alkyl, amino, —C(O)-amino, —S(O)$_2$-amino, hydroxy, cyano, azido, —COOH, and halogen; $C_6$-$C_{10}$ aryl optionally substituted with one or more substituents selected from the group consisting of $C_1$-$C_6$alkyl, —O—$C_1$-$C_6$alkyl, amino, —C(O)-amino, —S(O)$_2$-amino, hydroxy, cyano, azido, —COOH, and halogen; and 5-10 membered heteroaryl optionally substituted with one or more substituents selected from the group consisting of $C_1$-$C_6$alkyl, —O—$C_1$-$C_6$alkyl, amino, —C(O)-amino, —S(O)$_2$-amino, hydroxy, cyano, azido, —COOH, and halogen;

Q is a carboxylic acid, carboxylic acid prodrug moiety, or carboxylic acid isostere;

$R^1$, $R^2$, $R^{1a}$ and $R^{2a}$ are independently selected from the group consisting of —H; hydroxy; $C_1$-$C_{10}$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; —$C_2$-$C_{10}$alkenyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_2$-$C_{10}$alkynyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_3$-$C_7$ carbocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; 3-8 membered heterocyclyl optionally substituted with one or more substituents selected from the group consisting of $C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 5-10 membered heteroaryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen;

$R^3$ is hydrogen; hydroxy; $C_1$-$C_{10}$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, 5-10 membered heteroaryl, and halogen; —$C_1$-$C_{10}$alkyl-COOH optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_3$-$C_7$ carbocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano,-azido, and halogen; 3-8 membered-heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 5-10 membered heteroaryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen;

$R^4$ is selected from the group consisting of hydroxy, —C(O)$R^6$, —C(O)$NR^1R^2$, —C(O)$NR^1OR^3$, —$NR^1$C(O)$R^6$, —$NR^1$C(O)$OR^3$, —$NR^1$S(O)$_2R^3$, —$NR^1$S(O)$_2NR^2R^{1a}$, —C(=$NR^1$)$R^6$, —C(=$NR^1$)$NR^2R^{1a}$, —$NR^1CR^6$(=$NR^2$), —$NR^1$C(=$NR^2$)$NR^{1a}R^{2a}$, halogen, —$CF_3$, $C_1$-$C_6$ alkenyl, $C_1$-$C_6$ alkynyl, $C_1$-$C_6$ heteroalkyl, $C_3$-$C_7$ carbocyclyl, 3-10 membered heterocyclyl, $C_6$-$C_{10}$ aryl, 5-10 membered heteroaryl, cyano, $C_1$-$C_6$ alkoxy($C_1$-$C_6$)alkyl, $C_6$-$C_{10}$ aryloxy, sulfhydryl (mercapto), and —(CH$_2$)$_m$—Y'—(CH$_2$)$_p$M';

m and p are independently 0 to 3;

Y' is selected from the group consisting of —S—, —S(O)—, —S(O)$_2$—, —P(O)$R^1$—, —O—, —$CR^6R^7$—, and —$NR^1$—;

M' is selected from the group consisting of hydrogen; hydroxy; —C(O)$NR^1R^2$; —C(O)$NR^1OR^3$; —$NR^1$C(O)$R^6$; —$NR^1$C(O)$NR^2R^{1a}$; —$NR^1$C(O)$OR^3$; —$NR^1$S(O)$_2R^3$; —$NR^1$S(O)$_2NR^2R^{1a}$; —C(=$NR^1$)$R^6$; —C(=$NR^1$)$NR^2R^{1a}$; —$NR^1CR^6$(=$NR^2$); —$NR^1$C(=$NR^2$)$NR^{1a}R^{2a}$; —COOH; $C_1$-$C_4$ alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_{3-10}$ cycloalkyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$ aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; 5 to 10 membered heteroaryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 4 to 10 membered heterocyclyl optionally substituted with one or more substituents selected from the group consisting of $C_1$-$C_6$alkyl, —O—$C_1$-$C_6$ alkyl, —S—$C_1$-$C_6$alkyl, amino, —C(O)-amino, —S(O)$_2$-amino, hydroxy, cyano, azido, and halogen;

each $R^5$ is independently hydrogen, $C_1$-$C_6$alkyl, $C_2$-$C_6$ alkenyl, $C_2$-$C_6$ alkynyl, hydroxy, $OR^3$, —$SR^3$, halogen, amino, —C(O)-amino, —S(O)$_2$-amino, $C_3$-$C_7$ cycloalkyl, 3-8 membered heterocyclyl, and —$CF_3$; and each $R^6$ and $R^7$ are independently selected from the group consisting of hydrogen; hydroxy; amino; —C(O)-amino; —S(O)$_2$-amino; —O—$C_1$-$C_6$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; —S—$C_1$-$C_6$alkyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_1$-$C_{10}$alkyl optionally substituted with one or more substituents selected from the group consisting of —O—$C_1$-$C_6$alkyl, —S—$C_1$-$C_6$alkyl, amino, —C(O)-amino, —S(O)$_2$ramino, hydroxy, cyano, azido, and halogen; $C_2$-$C_{10}$alkenyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_2$-$C_{10}$alkynyl optionally substituted with one or more substituents selected from the group consisting of —O—$C_1$-$C_6$alkyl, —S—$C_1$-$C_6$alkyl, amino, —C(O)-amino, —S(O)$_2$-amino, hydroxy, cyano, azido, and halogen; $C_3$-$C_7$ cycloalkyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; 3-8 membered heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; $C_6$-$C_{10}$aryl optionally substituted with, one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen; and 5-10 membered heteroaryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)$_2$-amino, hydroxy, cyano, azido, and halogen.

2. The compound of claim 1, wherein $R^b$ is —C(O)G, —C(O)OG, —S(O)$_2$G, —C(=NR$^1$R$^2$)G or —C(=NOR$^3$)G.

3. The compound of claim 1, having the structure of Formula Ia or IIa:

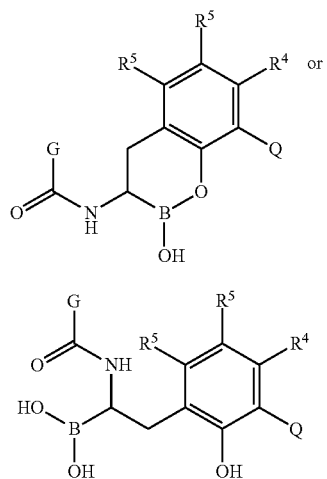

or pharmaceutically acceptable salts thereof, wherein:

G is selected from the group consisting of hydrogen; —NR$^1$R$^2$; —CH$_2$N$_3$; —CH$_2$CN; —C(O)NR$^1$R$^2$; —CH(=CH—R$^6$)R$^7$; —CH$_2$C(O)NR$^1$R$^2$; —CH$_2$S(O)$_2$ NR$^1$R$^2$; —CH$_2$C(O)OR$^3$; —CH$_2$—Y—Z; —SR$^3$; —P(O)R$^1$R$^2$; C$_1$-C$_{10}$alkyl optionally substituted with one or more substituents selected from the group consisting of —O—C$_1$-C$_6$alkyl, —S—C$_1$-C$_6$alkyl, amino, —C(O)-amino, —S(O)$_2$-amino, hydroxy, cyano, azido, and halogen; C$_3$-C$_7$ carbocyclyl optionally substituted with one or more substituents selected from the group consisting of C$_1$-C$_6$alkyl, —O—C$_1$-C$_6$alkyl, —S—C$_1$-C$_6$alkyl, amino, —C(O)-amino, —S(O)$_2$-amino, hydroxy, cyano, azido, and halogen; 5-10 membered heterocyclyl optionally substituted with one or more substituents selected from the group consisting of C$_1$-C$_6$alkyl, —O—C$_1$-C$_6$alkyl, —S—C$_1$-C$_6$alkyl, amino, —C(O)-amino, —S(O)$_2$-amino, hydroxy, cyano, azido, and halogen; C$_6$-C$_{10}$aryl optionally substituted with one or more substituents selected from the group consisting of C$_1$-C$_6$alkyl, —O—C$_1$-C$_6$alkyl, —S—C$_1$-C$_6$alkyl, amino, —C(O)-amino, —S(O)$_2$-amino, hydroxy, cyano, azido, and halogen; and 5-10 membered heteroaryl optionally substituted with one or more substituents selected from the group consisting of C$_1$-C$_6$alkyl, C$_6$-C$_{10}$aryl, 5-10 membered heteroaryl, —O—C$_1$-C$_6$alkyl, —S—C$_1$-C$_6$alkyl, amino, —C(O)-amino, —S(O)$_2$-amino, hydroxy, cyano, azido, and halogen;

R$^1$, R$^2$, R$^{1a}$, R$^{2a}$, R$^6$, and R$^7$ are each independently selected from the group consisting of hydrogen, hydroxy, and C$_1$-C$_4$alkyl; and R$^3$ is selected from the group consisting of hydrogen, hydroxy, C$_1$-C$_6$alkyl, C$_1$-C$_6$ cycloalkyl, and C$_1$-C$_6$heterocycle.

4. The compound of claim 1, having the structure of (Ia):

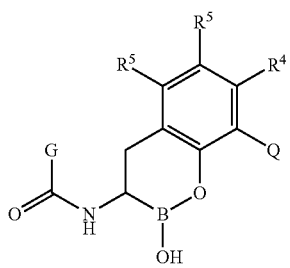

or pharmaceutically acceptable salts thereof.

5. The compound of claim 1, having the structure of (Ia-1) or (Ia-2):

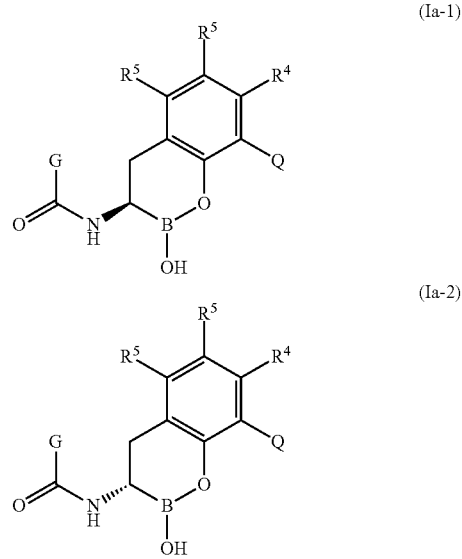

or pharmaceutically acceptable salts thereof.

6. The compound of claim 1, wherein R$^5$ is hydrogen.

7. The compound of claim 1, wherein at least one R$^5$ is a halogen.

8. The compound of claim 7, wherein at least one R$^5$ is —F or Cl.

9. The compound of claim 1, wherein R$^4$ is selected from the group consisting of C$_1$-C$_6$alkyl, C$_2$-C$_6$ alkenyl, C$_2$-C$_6$ alkynyl, C$_3$-C$_7$ carbocyclyl, C$_1$-C$_6$ heteroalkyl, 5-10 membered heterocyclyl, C$_6$-C$_{10}$ aryl, 5-10 membered heteroaryl, cyano, hydroxy, —OR$^3$, —SR$^3$, —S(O)$_2$M', —P(O)R$^1$M', and halogen.

10. The compound of claim 9, wherein R$^4$ is —SO$_3$H, —PO$_3$H$_2$, F, Cl, Me, —CF$_3$, or —(CH$_2$)$_m$—Y'—(CH$_2$)$_p$M' wherein m and p are 0.

11. The compound of claim 1, wherein R$^4$ is —(CH$_2$)m-Y'—(CH$_2$)pM' wherein:
m is 0;
p is 0 to 3;
Y' is O or S; and
M' is hydrogen; hydroxyl; —C(O)NR$^1$R$^2$; COOH; C$_1$-C$_4$ alkyl optionally substituted with one or more substituents selected from the group consisting of —O—C$_1$-C$_6$alkyl, —S—C$_1$-C$_6$alkyl, amino, —C(O)-amino, —S(O)₂-amino, hydroxy, cyano, azido, and halogen; C₃₋₁₀ cycloalkyl optionally substituted with one or more substituents selected from the group consisting of C₁-C₆alkyl, —O—C₁-C₆alkyl, —S—C₁-C₆alkyl, amino, —C(O)-amino, —S(O)₂-amino, hydroxy, cyano, azido, and halogen; C₆-C₁₀ aryl optionally substituted with one or more substituents selected from the group consisting of C₁-C₆alkyl, —O—C₁-C₆alkyl, —S—C₁-C₆alkyl, amino, —C(O)-amino, —S(O)₂-amino, hydroxy, cyano, azido, and halogen; 5 to 10 membered heteroaryl optionally substituted with one or more substituents selected from the group consisting of C₁-C₆alkyl, —O—C₁-C₆alkyl, —S—C₁-C₆alkyl, amino, —C(O)-amino, —S(O)₂-amino, hydroxy, cyano, azido, and halogen; and 4 to 10 membered heterocyclyl optionally substituted with one or more substituents selected from the group consisting of C₁-C₆alkyl, —O—C₁-C₆alkyl, —S—C₁-C₆alkyl, amino, —C(O)-amino, —S(O)₂-amino, hydroxy, cyano, azido, and halogen.

12. The compound of claim 11, wherein R⁴ is —O—C(O)NR¹R², —S—C₁-C₆alkyl, —S—C₁-C₆ cycloalkyl, —S—C₁-C₆heterocycle, or —O—C₁-C₆alkyl, and R¹ and R² in R⁴ are each independently selected from hydrogen and hydroxy.

13. The compound of claim 11, wherein R⁴ is —S—CH₃,

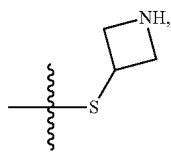 [SMILES: *SC1CNC1]

—OCH₃,

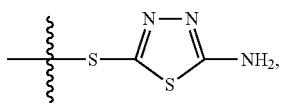 [SMILES: *Sc1nnc(N)s1]

—S—CH₂—C(O)—NH₂, —S—CH₂—CH₂—OH,

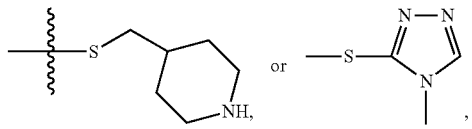

—O—C(O)NH₂, —O—C(O)NHOH.

14. The compound of claim 1, wherein R⁶ and R⁷ are independently selected from the group consisting of hydrogen, hydroxy, and —C₁-C₄alkyl.

15. The compound of claim 1, wherein Q is —COOR, and R is selected from the group consisting of hydrogen, C₁₋₉alkyl, —CR⁶R⁷OC(O)C₁₋₉alkyl, —CR⁶R⁷OC(O)OC₁₋₉alkyl, CR⁶R⁷OC(O)C₆₋₁₀aryl, CR⁶R⁷OC(O)OC₆₋₁₀aryl, and

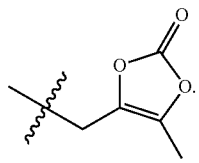 [SMILES: *Cc1oc(=O)oc1C]

16. The compound of claim 15, wherein R is —CH₂OC(O)CH₃, —CH₂OC(O)CH₂CH₃, —CH₂OC(O)CH₂CH₂CH₃, —CH₂OC(O)CH(CH₃)₂, —CH₂OC(O)C(CH₃)₃, —CH₂OC(O)OCH(CH₃)₂, —CH₂OC(O)OCH₂CH₃, or —CH₂OC(O)OC₆H₅.

17. The compound of claim 1, wherein G is H, —SO₃H, —PO₃H₂,

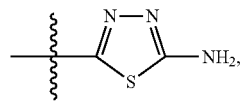 [SMILES: *c1nnc(N)s1]

—NH₂, CON(CH₃)₂, —CH₂OC(O)H, —CH₂OC(O)H(OH), —CH₂C(O)NH(CH₃), —CH₂C(O)N(CH₃)₂, —CH₂C(O)OH, or —S—CH₃.

18. The compound of claim 1, wherein G is selected from the group consisting of C₁-C₁₀ alkyl optionally substituted with one or more substituents selected from the group consisting of —O—C₁-C₆alkyl, —S—C₁-C₆alkyl, amino, —C(O)-amino, —S(O)₂-amino, hydroxy, cyano, azido, and halogen; C₃₋₇ carbocyclyl optionally substituted with one or more substituents selected from the group consisting of C₁-C₆alkyl, —O—C₁-C₆alkyl, —S—C₁-C₆alkyl, amino, —C(O)-amino, —S(O)₂-amino, hydroxy, cyano, azido, and halogen; 5-10 membered heterocyclyl optionally substituted with one or more substituents selected from the group consisting of C₁-C₆alkyl, —O—C₁-C₆alkyl, —S—C₁-C₆alkyl, amino, —C(O)-amino, —S(O)₂-amino, hydroxy, cyano, azido, and halogen; C₆₋₁₀aryl optionally substituted with one or more substituents selected from the group consisting of C₁-C₆alkyl, —O—C₁-C₆alkyl, —S—C₁-C₆alkyl, amino, —C(O)-amino, —S(O)₂-amino, hydroxy, cyano, azido, and halogen; and 5-10 membered heteroaryl optionally substituted with one or more substituents selected from the group consisting of C₁-C₆alkyl, —C₆-C₁₀aryl, 5-10 membered heteroaryl, —O—C₁-C₆alkyl, —S—C₁-C₆alkyl, amino, —C(O)-amino, —S(O)₂-amino, hydroxy, cyano, azido, and halogen.

19. The compound of claim 1, wherein G is —C(O)NR¹R² and R¹ and R² are each independently selected from hydrogen and C₁-C₆alkyl; —CH₂OC(O) R¹R² and R¹ and R² are each independently selected from hydrogen and hydroxy; —CH₂C(O)NR¹R² and R¹ and R² are each independently selected from hydrogen and C₁-C₄alkyl; or —CH₂C(O)OR³ and R³ is hydrogen or C₁-C₆alkyl.

20. The compound of claim 1, wherein:

G is —CH₂—Y—Z; and

Y is —S—; —S(O)₂—, or —CH₂—.

21. The compound of claim 20, wherein Z is —CH₃,

[structure: azetidine-NH]

—CH₂CN, —CH₂N₃, —CH₂F, —CHF₂, or —CF₃.

22. The compound of claim 20, wherein Z is selected from the group consisting of thiophene, imidazole, N-methylimidazole, aminoimidazole, triazole, N-methyltriazole, aminotriazole, tetrazole, N-methyltetrazole, aminotetrazole, thiazole, aminothiazole, thiadiazole, aminothiadiazole, oxazole, oxadiazole, pyridine, pyridazine, pyrimidine, pyrazine, azitidine and piperdine.

23. The compound of claim 22, wherein Z is selected from the group consisting of

[structures: thiophene, azetidine, pyridine, fluoropyridine, pyrimidine, thiazole, aminothiadiazole, aminooxadiazole, aminotriazole, N-methyl-aminotriazole, aminooxadiazole, aminotriazole, N-aminotriazole, triazole, and thiazole]

24. The compound of claim 1, having the structure selected from the group consisting of:

[boronic acid compound structures with various substituents]

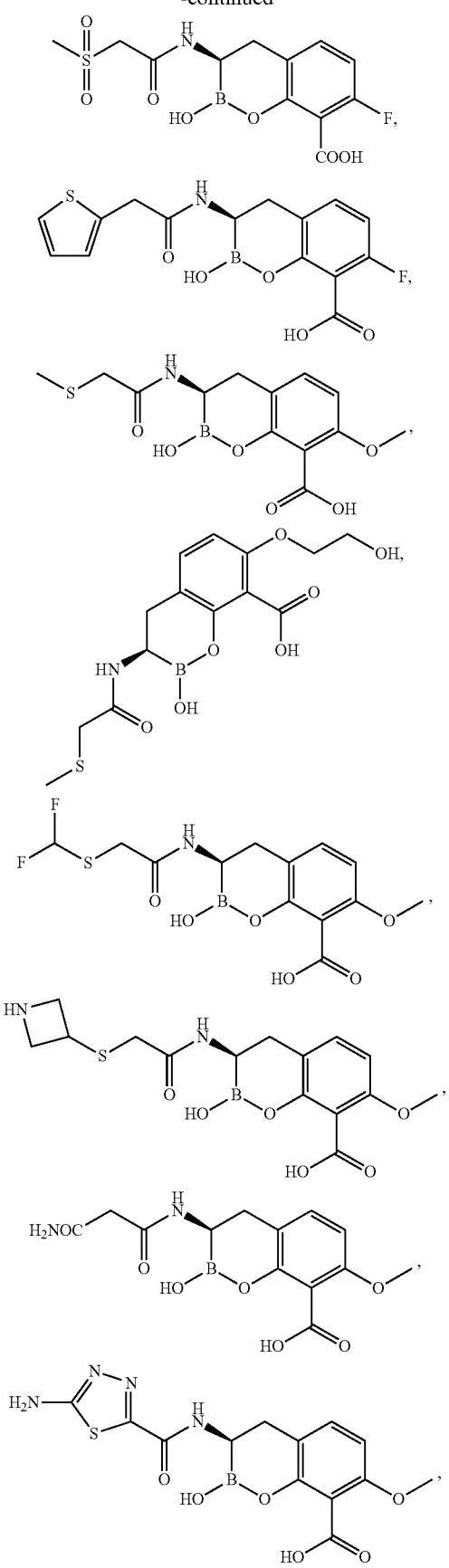
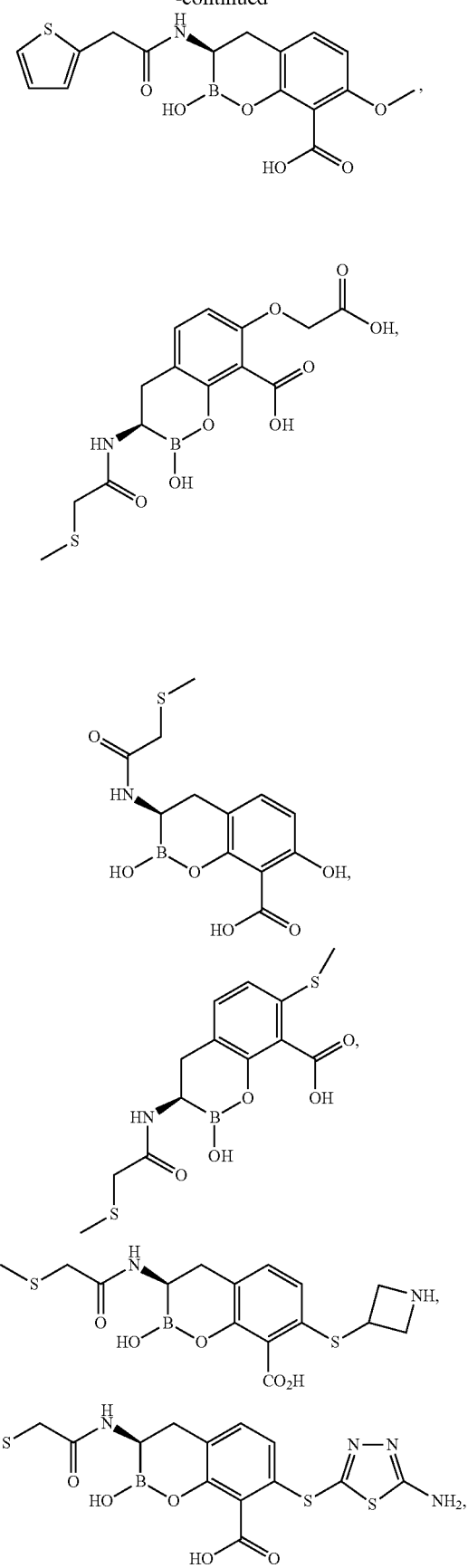

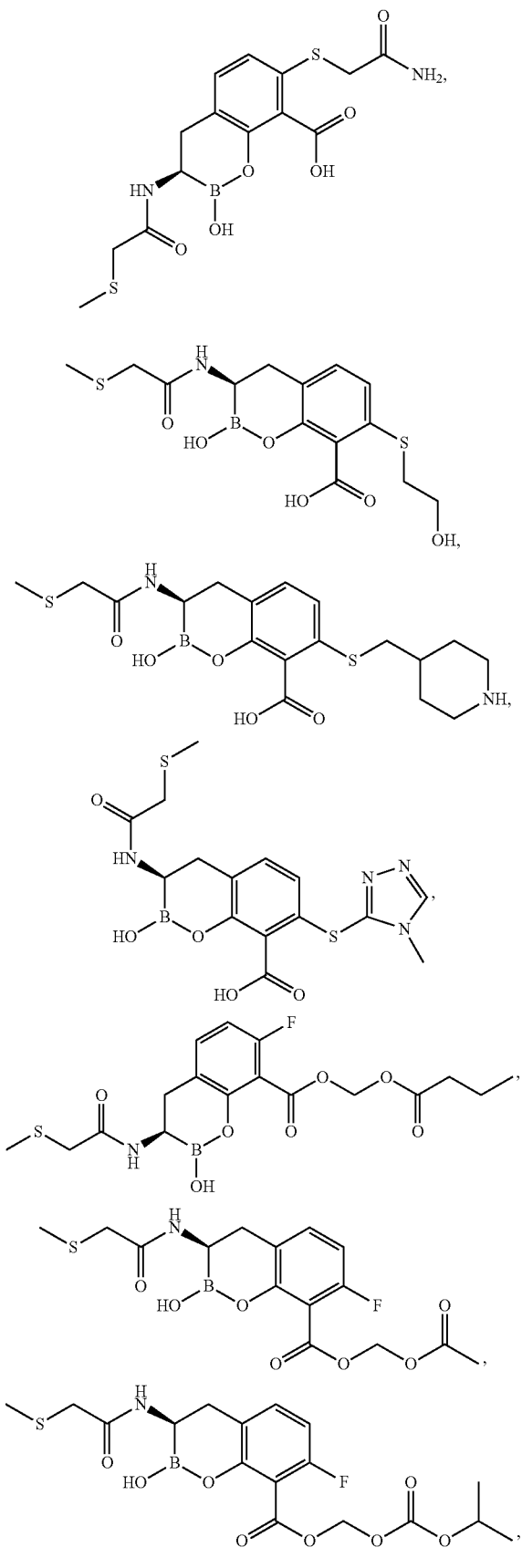
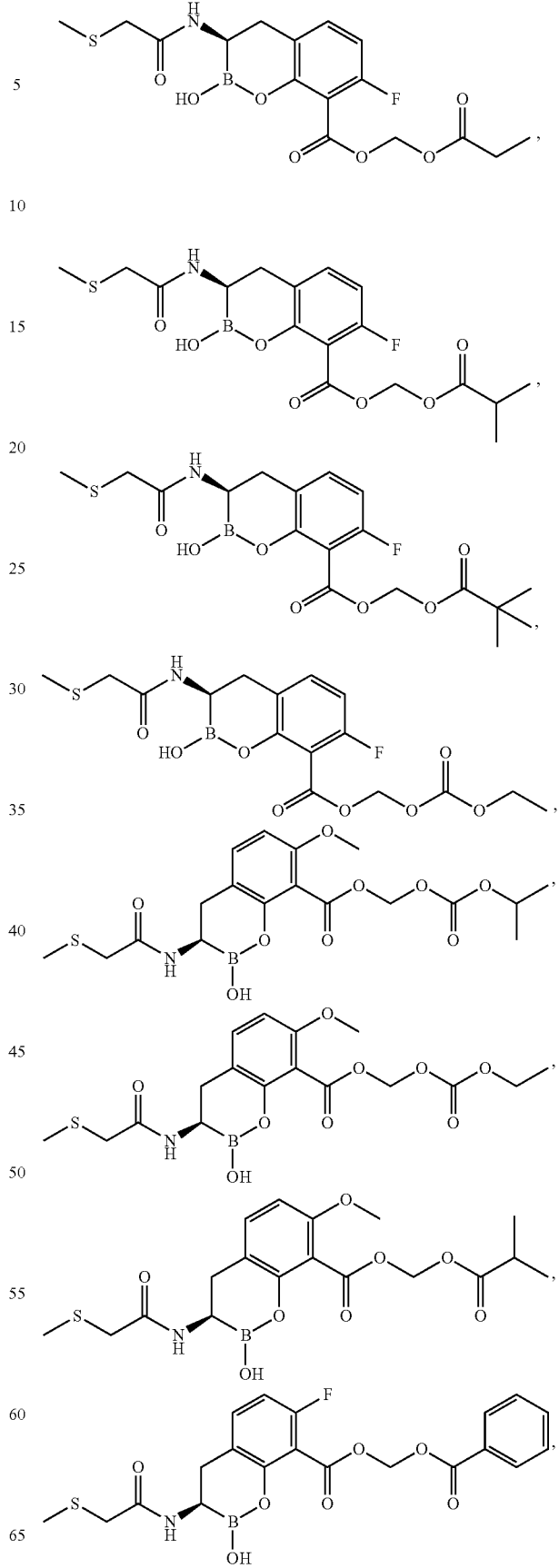

-continued

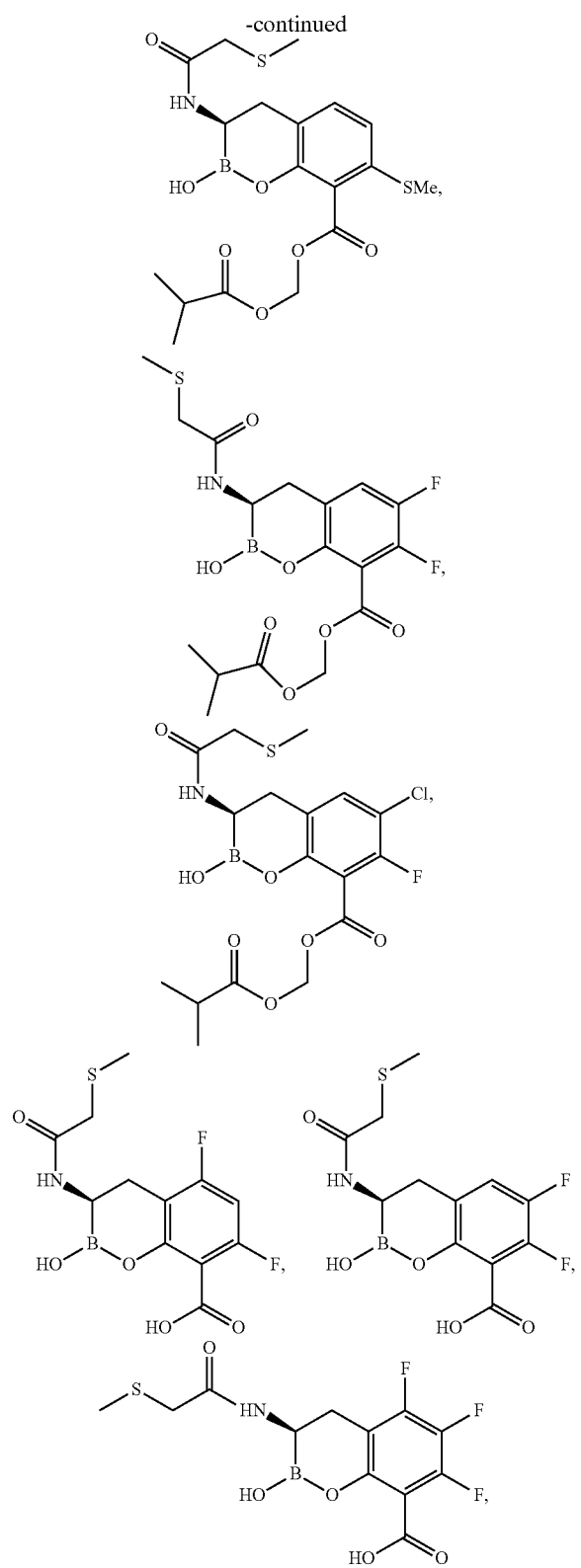

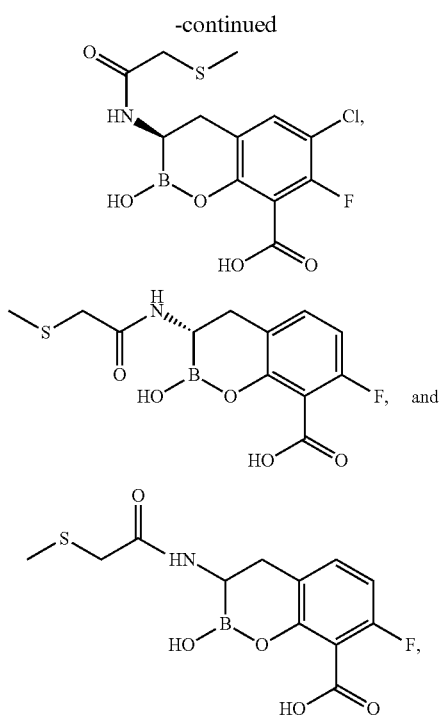

or pharmaceutically acceptable salts thereof.

25. A pharmaceutical composition comprising a therapeutically effective amount of a compound of claim 1 and a pharmaceutically acceptable excipient.

26. The pharmaceutical composition of claim 25, wherein the pharmaceutically acceptable excipient is meglumine.

27. The pharmaceutical composition of claim 25, further comprising an additional medicament selected from an antibacterial agent, an antifungal agent, an antiviral agent, an anti-inflammatory agent, or an anti-allergic agent.

28. The composition of claim 27, wherein the additional medicament is a β-lactam antibacterial agent selected from Ceftazidime, Biapenem, Doripenem, Ertapenem, Imipenem, Meropenem, Tebipenem, Ceftibuten, Panipenem, Aztreonam, Tigemonam, BAL30072, SYN 2416, or Carumonam.

29. A method of treating a bacterial infection, comprising administering to a subject in need thereof, a compound of claim 1.

30. The method of claim 29, further comprising administering to the subject an additional medicament selected from an antibacterial agent, an antifungal agent, an antiviral agent, an anti-inflammatory agent, or an anti-allergic agent.

31. The method of claim 30, wherein the additional medicament is a β-lactam antibacterial agent selected from Ceftazidime, Biapenem, Doripenem, Ertapenem, Imipenem, Meropenem, Tebipenem, Ceftibuten, Panipenem, Aztreonam, Tigemonam, BAL30072, SYN 2416, or Carumonam.

* * * * *